US007462639B2

(12) United States Patent  
Georges et al.

(10) Patent No.: US 7,462,639 B2  
(45) Date of Patent: Dec. 9, 2008

(54) AMINOPYRAZOLE DERIVATIVES

(75) Inventors: Guy Georges, Habach (DE); Bernhard Goller, Penzberg (DE); Klaus-Peter Kuenkele, Benediktbeuern (DE); Aude Lemarchand, Munich (DE); Anja Limberg, Penzberg (DE); Ulrike Reiff, Penzberg (DE); Petra Rueger, Penzberg (DE); Matthias Rueth, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 186 days.

(21) Appl. No.: 11/384,052

(22) Filed: Mar. 17, 2006

(65) Prior Publication Data  
US 2006/0235065 A1    Oct. 19, 2006

(30) Foreign Application Priority Data  
Apr. 14, 2005 (EP) .................................. 05008111  
Apr. 14, 2005 (EP) .................................. 05008224

(51) Int. Cl.  
*A61K 31/4155* (2006.01)  
*C07D 487/04* (2006.01)

(52) U.S. Cl. .................. 514/394; 548/429; 548/433  
(58) Field of Classification Search ................. 548/429, 548/433  
See application file for complete search history.

(56) References Cited  
U.S. PATENT DOCUMENTS

| | | | |
|---|---|---|---|
| 4,282,361 A | 8/1981 | Hecht et al. | |
| 4,666,923 A | 5/1987 | Hölck et al. | |
| 4,695,567 A | 9/1987 | Mertens et al. | |
| 4,824,975 A | 4/1989 | Fiege et al. | |
| 4,835,280 A | 5/1989 | Martens et al. | |
| 4,863,945 A | 9/1989 | Friebe et al. | |
| 4,954,498 A | 9/1990 | Mertens et al. | |
| 4,985,448 A | 1/1991 | Zilch et al. | |
| 5,212,186 A | 5/1993 | Paal et al. | |
| 6,207,401 B1 | 3/2001 | Plowman et al. | |
| 6,534,524 B1 | 3/2003 | Kania et al. | |
| 2001/0051620 A1 | 12/2001 | Berger et al. | |

FOREIGN PATENT DOCUMENTS

| | | |
|---|---|---|
| DE | 19 45 430 | 3/1970 |
| DE | 1 907 117 | 9/1970 |
| DE | 34 10 168 | 9/1985 |
| DE | 3 618 135 | 12/1987 |
| EP | 868 519 | 10/1998 |
| EP | 1 051 500 | 11/2000 |
| WO | WO 93/19059 | 9/1993 |
| WO | WO 93/23373 | 11/1993 |
| WO | WO 95/19169 | 7/1995 |
| WO | WO 95/23141 | 8/1995 |
| WO | WO 97/42187 | 11/1997 |
| WO | WO 99/06396 | 2/1999 |
| WO | WO 00/35920 | 6/2000 |
| WO | WO 00/38680 | 7/2000 |
| WO | WO 00/44728 | 8/2000 |
| WO | WO 00/47212 | 8/2000 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/55116 | 8/2001 |
| WO | WO 01/77085 | 10/2001 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/057259 | 7/2002 |
| WO | WO 02/059111 | 8/2002 |
| WO | WO 02/059112 | 8/2002 |
| WO | WO 02/062789 | 8/2002 |
| WO | WO 02/066461 | 8/2002 |
| WO | WO 02/068415 | 9/2002 |
| WO | WO 02/096905 | 12/2002 |
| WO | WO 03/035065 | 5/2003 |
| WO | WO 03/077921 | 9/2003 |
| WO | WO 03/078423 | 9/2003 |
| WO | WO 03/078426 | 9/2003 |
| WO | WO 03/078427 | 9/2003 |

(Continued)

OTHER PUBLICATIONS

Adams et al., Trends Cell Biol., 11, pp. 49-54 (2001).

(Continued)

*Primary Examiner*—Rita J Desai  
(74) *Attorney, Agent, or Firm*—George W. Johnston; Patricia S. Rocha-Tramaloni; Gene J. Yao

(57) ABSTRACT

The present invention relates to the compounds of formula I:

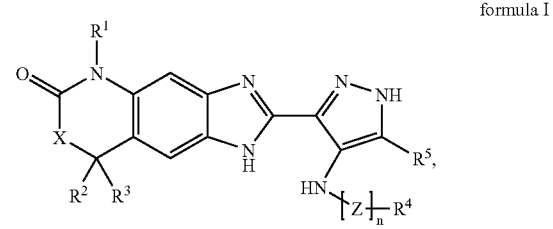

formula I their pharmaceutically acceptable salts or esters, enantiomeric forms, diastereoisomers and racemates, the preparation of the above-mentioned compounds, pharmaceutical compositions containing them and their manufacture, as well as the use of such compounds in the control or prevention of illnesses such as cancer.

17 Claims, No Drawings

FOREIGN PATENT DOCUMENTS

| WO | WO 04/000833 | 12/2003 |
| WO | WO 2004/005283 | 1/2004 |
| WO | WO 2005/002552 | 1/2005 |
| WO | WO 2005/111040 | 11/2005 |
| WO | WO 2006/032519 | 3/2006 |

OTHER PUBLICATIONS

Bastin et al., Organic Proc. Res. Deve., 4, pp. 427-439 (2000).
Bischoff et al., Trends Cell Biol., 9, pp. 454-459 (1999).
Giet et al., J. Cell Science, 112, pp. 3591-3601 (1999).
Harrington et al., Nat. Medicine, 10, pp. 262-267 (2004).
Hunter, T., Cell, 50, pp. 823-829 (1987).
Isola et al., Am. J. Pathology, 147, pp. 905-911 (1995).
Mertens et al., J. Med. Chem., 30, pp. 1279-1287 (1987).
Nigg, E.A., Nat. Rev. Mol. Cell Biol., 2, pp. 21-32 (2001).
Sen et al., J. Natl. Cancer Inst., 94, pp. 1320-1329 (2002).
Takei et al., Bull. Chem. Soc. Jpn., 52, pp. 208-211 (1979).
Von der Saal et al., J. Med. Chem., 32, pp. 1481-1491 (1989).

AMINOPYRAZOLE DERIVATIVES

PRIORITY TO RELATED APPLICATIONS

This application claims the benefit of European Application No. 05008111.6, filed Apr. 14, 2005 and European Application No. 05008224.7, filed Apr. 14, 2005. The entire contents of the above-identified applications are hereby incorporated by reference.

FIELD OF THE INVENTION

The present invention relates to novel tricyclic aminopyrazole derivatives, to a process for their manufacture, pharmaceutical compositions containing them and their manufacture as well as the use of these compounds as pharmaceutically active agents.

BACKGROUND OF THE INVENTION

Protein kinases regulate many different signaling processes by adding phosphate groups to proteins (Hunter, T., Cell 50 (1987) 823-829); particularly serine/threonine kinases phosphorylate proteins on the alcohol moiety of serine or threonine residues. The serine/threonine kinase family includes members that control cell growth, migration, differentiation, gene expression, muscle contraction, glucose metabolism, cellular protein synthesis, and regulation of the cell cycle.

Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The Aurora kinases are a family of serine/threonine kinases that are believed to play a key role in the protein phosphorylation events that are essential for the completion of essential mitotic events. The Aurora kinase family is made up of three key members: Aurora A, B and C (also known as Aurora-2, Aurora-1 and Aurora-3 respectively). Aurora-1 and Aurora-2 are described in U.S. Pat. No. 6,207,401 of Sugen and in related patents and patent applications, e.g. EP 0 868 519 and EP 1 051 500.

For Aurora A there is increasing evidence that it is a novel proto-oncogene. The Aurora A gene is amplified and the transcript/protein is highly expressed in a majority of human tumor cell lines and primary colorectal, breast and other tumors. It has been shown that Aurora A overexpression leads to genetic instability shown by amplified centrosomes and significant increase in aneuploidy and transforms Rat1 fibroblasts and mouse NIH3T3 cells in vitro. Aurora A-transformed NIH3T3 cells grow as tumors in nude mice (Bischoff, J. R., and Plowman, G. D., Trends Cell Biol. 9 (1999) 454-459; Giet, R., and Prigent, C., J. Cell Sci. 112 (1999) 3591-3601; Nigg, E. A., Nat. Rev. Mol. Cell Biol. 2 (2001) 21-32; Adams, R. R., et al., Trends Cell Biol. 11 (2001) 49-54). Moreover, amplification of Aurora A is associated with aneuploidy and aggressive clinical behavior (Sen, S., et al., J. Natl. Cancer Inst. 94 (2002) 1320-1329) and amplification of its locus correlates with poor prognosis for patients with node-negative breast cancer (Isola, J. J., et al., Am. J. Pathology 147 (1995) 905-911). For these reasons it is proposed that Aurora A overexpression contributes to cancer phenotype by being involved in chromosome segregation and mitotic checkpoint control.

Human tumor cell lines depleted of Aurora A transcripts arrest in mitosis. Accordingly, the specific inhibition of Aurora kinase by selective inhibitors is recognized to stop uncontrolled proliferation, re-establish mitotic checkpoint control and lead to apoptosis of tumor cells. In a xenograft model, an Aurora inhibitor therefore slows tumor growth and induces regression (Harrington, E. A., et al., Nat. Med. 10 (2004) 262-267).

Low molecular weight inhibitors for protein kinases are widely known in the state of the art. For Aurora inhibition such inhibitors are based on for example. quinazoline derivatives as disclosed in WO 00/44728; WO 00/47212; WO 01/21594; WO 01/21595; WO 01/21596; WO 01/21597; WO 01/77085; WO 01/55116; WO 95/19169; WO 95/23141; WO 97/42187; and WO 99/06396; pyrazole and triazole derivatives as disclosed in WO 02/22601; WO 02/22602; WO 02/22603; WO 02/22604; WO 02/22605; WO 02/22606; WO 02/22607; WO 02/22608; WO 02/50065; WO 02/50066; WO 02/057259; WO 02/059112; WO 02/059111; WO 02/062789; WO 02/066461; and WO 02/068415; pyrimidine derivatives as disclosed in WO 03/077921; WO 03/078423; WO 03/078426; WO 03/078427; and WO 04/000833; and imidazole, oxazole and thiazole derivatives as disclosed in WO 02/96905 and WO 04/005283.

WO 2005/002552 relates to pyrazole derivatives as inhibitors of cyclin dependent kinases (CDK), glycogen synthase kinase-3 (GSK-3) and Aurora kinase. WO 03/035065 relates to benzimidazole derivatives as kinase inhibitors, especially as inhibitors against kinase insert domain containing receptor (KDR) tyrosine kinase, spleen tyrosine kinase (SYK) and inducible T cell kinase (ITK). Some related tricyclic compounds are known as inhibitors of erythrocyte aggregation from U.S. Pat. Nos. 4,835,280A and 4,954,498A. Also Mertens, A., et al., J. Med. Chem. 30 (1987) 1279-1287; von der Saal, W., et al., J. Med. Chem. 32 (1989) 1481-1491; U.S. Pat. Nos. 4,666,923A; 4,695,567A and 4,863,945A describe related tricycles as erythrocyte aggregation inhibitors. U.S. Pat. No. 5,212,186A describes related tricycles for the treatment of cardiac insufficiency, hypertension and other diseases. WO 2005/111040 describes pyrrolobenzimidazolones with tubulin inhibitory activity as antiproliferative agents.

SUMMARY OF THE INVENTION

The present invention relates to tricyclic aminopyrazole derivatives of the general formula I, and all pharmaceutically acceptable salts or esters thereof wherein formula I is:

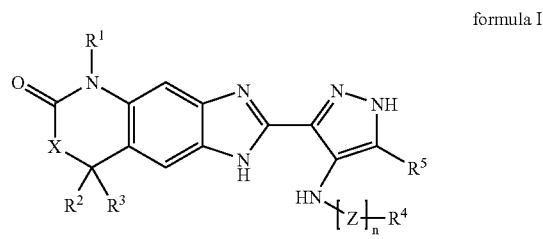

formula I wherein:
(a) $R^1$ is selected from the group consisting of:
  (1) hydrogen;
  (2) alkyl, which is optionally substituted one or more times with nitro, cyano or —Y—$R^6$;
  (3) alkenyl, which is optionally substituted one or more times with nitro, cyano or —Y—$R^6$; and (4) alkynyl, which is optionally substituted one or more times with nitro, cyano or —Y—$R^6$;
(b) Y is selected from the group consisting of:
  (1) a single bond;
  (2) —C(O)NH—;
  (3) —C(O)N(alkyl)-;
  (4) —N(alkyl)C(O)—;
  (5) —NHC(O)—;
  (6) —NHC(O)NH—;
  (7) —NHC(O)N(alkyl)-;
  (8) —NHS(O)$_2$—;
  (9) —S(O)$_2$NH—;
  (10) —S(O)$_2$N(alkyl)-;
  (11) —S(O)$_2$—;
  (12) —S(O)—;
  (13) —C(O)O—;
  (14) —OC(O)—;
  (15) —C(O)—;
  (16) —P(O)(alkyl)-;
  (17) —NH—;
  (18) —N(alkyl)-;
  (19) —O—; and
  (20) —S—;
(c) $R^6$ is selected from the group consisting of:
  (1) alkyl, which is optionally substituted one or more times by halogen, hydroxy, alkoxy, alkoxyalkoxy, amino, alkylamino, dialkylamino, —C(O)OH or —C(O)NH$_2$;
  (2) aryl, which is optionally substituted one or more times by halogen, cyano, nitro, amino, hydroxy, ($C_1$-$C_4$)alkyl, ($C_1$-$C_4$)alkoxy, halogenated ($C_1$-$C_4$)alkyl or halogenated ($C_1$-$C_4$)alkoxy;
  (3) heteroaryl, which is optionally substituted one or more times by alkyl;
  (4) cycloalkyl; and
  (5) heterocyclyl;
(d) $R^2$ and $R^3$ form together with the carbon atom to which they are attached a ($C_5$-$C_6$)cycloalkyl ring, or alternatively, $R^2$ and $R^3$ are independently selected from the group consisting of:
  (1) hydrogen; and
  (2) alkyl;
(e) Z is selected from the group consisting of:
  (1) —C(O)—,
  (2) —C(O)N$R^7$—,
  (3) —C(O)O—,
  (4) —S(O)$_2$—, and
  (5) —S(O)$_2$N$R^7$—;
(f) n is 0 or 1;
(g) $R^7$ is hydrogen or alkyl;
(h) $R^4$ is selected from the group consisting of:
  (1) hydrogen;
  (2) alkyl, which is optionally substituted one or more times by halogen, hydroxy, alkoxy, alkoxyalkoxy, amino, alkylamino or dialkylamino;
  (3) aryl-V—, wherein the aryl is optionally substituted one or more times by halogen, cyano, nitro, amino, alkylamino, dialkylamino, 2,4-dioxa-pentan-1,5-diyl, 2,5-dioxa-hexan-1,6-diyl, hydroxy, ($C_1$-$C_4$) alkyl, ($C_1$-$C_4$)alkoxy, halogenated ($C_1$-$C_4$)alkyl or halogenated ($C_1$-$C_4$)alkoxy;
  (4) heteroaryl-V—, wherein the heteroaryl is optionally substituted one or more times by alkyl;
  (5) cycloalkyl-V—; and
  (6) heterocyclyl-V—;
with the proviso that $R^4$ is not hydrogen, if n is 1 and Z is —C(O)O—;
(i) V is selected from the group consisting of:
  (1) a single bond,
  (2) alkylene,
  (3) —O-alkylene,
  (4) cycloalkylene, and
  (5) alkenylene;
(j) $R^5$ is selected from the group consisting of:
  (1) hydrogen,
  (2) alkyl,
  (3) fluorine, and
  (4) chlorine; and
(k) X is a single bond, —CH$_2$— or —C(alkyl)$_2$—.

The compounds of the present invention show activity as protein kinase inhibitors and therefore such compounds are useful for preventing or treating diseases associated with abnormal cellular responses triggered by protein kinase mediated events. In particular, the compounds of the present invention show activity as Aurora family kinase inhibitors, especially as Aurora A kinase inhibitors, and may therefore be useful for the treatment of diseases mediated by said kinase. Aurora A inhibition leads to cell cycle arrest in the G2 phase of the cell cycle and exerts an antiproliferative effect in tumor cell lines. This indicates that Aurora A inhibitors may be useful in the treatment of hyperproliferative diseases such as cancer and in particular colorectal cancer, breast cancer, lung cancer, prostate cancer, pancreatic cancer, gastric cancer, bladder cancer, ovarian cancer, melanoma, neuroblastoma, cervical cancer, kidney or renal cancer, leukemias and lymphomas. Auroa A inhibitors may also be useful for the treatment of acute-myelogenous leukemia (AML), acute lymphocytic leukemia (ALL) and gastrointestinal stromal tumor (GIST).

The present invention provides compounds of formula I and their tautomers, pharmaceutically acceptable salts or esters, enantiomeric forms, diastereoisomers and racemates, their use as Aurora kinase inhibitors, the preparation of the above-mentioned compounds, compositions containing them and their manufacture as well as the use of the above-mentioned compounds in treatment, control or prevention of illnesses, especially the illnesses and disorders mentioned above or in the manufacture of corresponding pharmaceutical compositions.

DETAILED DESCRIPTION OF THE INVENTION

The term "alkyl" as used herein means a saturated, straight-chain or branched-chain hydrocarbon containing from 1 to 6 carbon atoms, preferably 1 to 4 carbon atoms, such as methyl, ethyl, n-propyl, isopropyl, n-butyl, 2-butyl, t-butyl, n-pentyl, and n-hexyl.

The term "alkenyl" as used herein means an unsaturated straight-chain or branched aliphatic hydrocarbon group containing one double bond and having 2 to 6 carbon atoms, preferably 2 to 4 carbon atoms. Examples of such "alkenyl groups" are vinyl(ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6 carbon atoms, preferably 2 to 4 carbon atoms. Examples of such "alkynyl groups" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "alkoxy" as used herein means an alkyl-O-group wherein the alkyl is defined as above.

The term "alkoxyalkoxy" as used herein means an alkyl-O-alkoxy group wherein alkyl and alkoxy are defined as above.

The term "alkylamino" as used herein means an alkyl-NH— group wherein the alkyl is defined as above.

The term "dialkylamino" as used herein means an (alkyl)$_2$N— group wherein the alkyl is defined as above.

In a particular preferred embodiment, the alkyl, alkenyl, or alkynyl encompassed by the $R^1$ group in formula I which are "optionally substituted one or more times with nitro, cyano or —Y—$R^6$;" are optionally substituted one to three times, more preferably one to two times, and more preferably one time, by nitro, cyano or —Y—$R^6$.

In a particular preferred embodiment, the optionally substituted alkyl encompassed by the $R^4$ or $R^6$ group in formula I is optionally substituted one to six times and more preferably one to three times by halogen, preferably by fluorine or chlorine, more preferably by fluorine; or said optionally substituted alkyl encompassed by the $R^6$ group in formula I is preferably substituted one to three times, more preferably one to two times by hydroxy, alkoxy, alkoxyalkoxy, amino, alkylamino, dialkylamino, —C(O)OH or —C(O)NH$_2$. Examples of such optionally substituted alkyl groups are difluoromethyl, trifluoromethyl, 2,2,2-trifluoroethyl, perfluorethyl, 2-hydroxy-butyl, 2-hydroxy-ethyl, 2-hydroxy-propyl, 3-hydroxy-butyl, 2,3-dihydroxy-propyl, 2,3-dihydroxy-butyl, 1,2,3-trihydroxy-propyl, 2-hydroxy-pentyl, 2-methoxy-ethyl, 2-ethoxy-ethyl, 4-methoxy-butyl, 2-methoxy-butyl, 2-ethoxy-propyl, 3-propoxy-butyl, 2,3-dimethoxy-propyl, 2-ethoxy-3-methoxy-propyl, 2,3-diethoxy-butyl, 1,2,3-trimethoxy-propyl, 2-methoxy-pentyl, 2-(2-methoxy-ethoxy)-ethyl, 2-(2-ethoxyethoxy)-ethyl, 2-(2-propoxy-ethoxy)-ethyl, 3-(2-methoxy-ethoxy)-propyl, 3-(1-methoxyethoxy)-propyl, 4-(2-ethoxy-ethoxy)-butyl, 2-amino-butyl, 2-amino-ethyl, 2-amino-propyl, 3-amino-propyl, 3-amino-butyl, 2,3-diamino-propyl, 2-methylamino-butyl, 2-ethylaminoethyl, 2-dimethylamino-ethyl, 2-dimethylamino-propyl, 3-diethylamino-propyl, 3-amino-butyl, 2,3-diamino-propyl, preferably 2,3-dihydroxy-propyl, 2-methoxy-ethyl, 2-(2-methoxy-ethoxy)-ethyl, trifluoromethyl, and trifluoromethoxy.

In a particular preferred embodiment, the optionally substituted aryl encompassed by the $R^4$ or $R^6$ group in formula I is optionally substituted one to five times, more preferably one to three times, and more preferably one to two times.

In a particular preferred embodiment, the optionally substituted heteroaryl encompassed by the $R^4$ or $R^6$ group in formula I is optionally substituted one to two times and more preferably one time.

The term "halogenated alkyl" as used herein means an alkyl group as defined above which is substituted one or more times by halogen, preferably substituted one to six times by halogen, and more preferably substituted one to three times by halogen; preferably by fluorine or chlorine, more preferably by fluorine. Examples are difluoromethyl, trifluoromethyl, 2,2,2-trifluoroethyl, perfluorethyl, and the like, preferably trifluoromethyl.

The term "halogenated alkoxy" as used herein means an alkoxy group as defined above which is substituted one or more times by halogen, preferably by fluorine or chlorine, preferably fluorine. Examples are difluoromethoxy, trifluoromethoxy, 2,2,2-trifluoroethoxy, perfluoroethoxy and the like, especially trifluoromethoxy.

The term "alkylene" as used herein means a saturated, straight-chain or branched-chain hydrocarbon, preferably a straight-chain hydrocarbon containing from 1 to 5 carbon atoms, preferably from 1 to 3, carbon atoms, such as methylene, ethylene, trimethylene (1,3-propylene); tetramethylene (butylene), pentamethylene, methyl-methylene, ethyl-methylene, methyl-ethylene (1,2-propylene), ethyl-ethylene, propyl-ethylene, 1-methyl-trimethylene, 2-methyl-trimethylene, 1-ethyl-trimethylene, 2-ethyl-trimethylene and the like, preferably methylene, ethylene, methyl-methylene or ethyl-methylene.

The term "alkenylene" as used herein means an unsaturated, straight-chain or branched-chain hydrocarbon, preferably a straight-chain hydrocarbon, containing one double bond and containing from 2 to 5 carbon atoms, preferably from 2 to 3 carbon atoms. Examples of such "alkenylenes" are vinylene (ethenylene), allylene, isopropenylene, 1-propenylene, 2-methyl-1-propenylene, 1-butenylene, 2-butenylene, 3-butenylene, 2-ethyl-1-butenylene, 2-pentenylene, 3-pentenylene, 4-pentenylene, 4-methyl-3-pentenylene and the like, preferably vinylene or allylene and more preferably vinylene.

The term "—O-alkylene" as used herein means an alkylene as defined above which is attached via an oxygen atom (—O—) to $R^4$ at one side of the bivalent alkylene radical and which is attached to -[Z]$_n$-NH-pyrazole at the other side of such bivalent radical. Thus, such —O-alkylene-groups form together with $R^4$ and -[Z]$_n$-NH-pyrazole e.g an aryl-O-alkylene-[Z]$_n$-NH-pyrazole, a heteroaryl-O-alkylene-[Z]$_n$-NH-pyrazole, a cycloalkyl-O-alkylene-[Z]$_n$-NH-pyrazole, or a heterocyclyl-O-alkylene-[Z]$_n$-NH-pyrazole group.

The term "halogen" as used herein means fluorine, chlorine, bromine and iodine, preferably fluorine, chlorine or bromine and more preferably fluorine or chlorine.

The term "cycloalkyl" as used herein means a monocyclic saturated hydrocarbon ring with 3 to 7 ring atoms, preferably 3 to 6 ring atoms. Such saturated carbocyclic groups can be optionally substituted one or more times, preferably one to three times by alkyl, more preferably one to two times. Preferably such saturated carbocyclic groups are unsubstituted. Examples of such saturated carbocyclic groups are cyclopropyl, cyclobutyl, cyclopentyl, cyclohexyl, cycloheptyl, 3-methyl-cyclopentyl, 3,3-dimethyl-cyclohexyl, 3-methyl-cyclohexyl, 2-methyl-cyclohexyl, preferably cyclopentyl, cyclohexyl, cyclopropyl or methyl-cyclopropyl and more preferably cyclopropyl.

The cycloalkyl ring which is formed by $R^2$ and $R^3$ together with the carbon atom to which they are attached is preferably a cyclopentyl or cyclohexyl ring, and more preferably a cyclopentyl ring.

The term "cycloalkylene" as used herein means a monocyclic saturated hydrocarbon ring with 3 to 6 ring atoms, preferably 3 to 5 ring atoms. Such saturated cycloalkylene groups can be optionally substituted one to three times, preferably one or two times, by alkyl. Preferably such cycloalkylene groups are unsubstituted. Examples of such cycloalkylene groups are 1,2-cyclopropylene, 1,1-cyclopropylene, 1,3-cyclobutylene, 1,3-cyclopentylene and the like, preferably 1,2-cyclopropylene or 1,1-cyclopropylene.

The term "heterocyclyl" as used herein means a saturated, monocyclic ring with 4 to 7 ring atoms, preferably 5 to 7 ring atoms, which contains up to 3 heteroatoms, preferably 1 or 2 heteroatoms selected independently from the group consisting of N, O and S with the remaining ring atoms being carbon atoms. Preferably at least one heteroatom of the ring is nitrogen and the remaining heteroatoms are selected independently from the group consisting of nitrogen, oxygen and sulfur, and such heterocyclyl group is preferably attached via the ring nitrogen atom. Such saturated heterocyclic group can be optionally substituted one or more times, preferably one or two times by a substituent selected from the group consisting of: (a) alkyl, preferably methyl; (b) —C(O)-alkyl, preferably acetyl; (c) oxo; (d) —S(O)$_2$-alkyl; and (e) alkoxy. Preferred substituents are: (a) alkyl; (b) —C(O)-alkyl; (c) oxo; or (d) —S(O)$_2$-alkyl; and particularly preferred substituents are: (a) alkyl or (b) —C(O)-alkyl. Examples of such saturated heterocyclic groups include oxetanyl (preferably oxetan-3-yl), 3-methyl-oxetan-3-yl, pyrrolidinyl, morpholinyl, piperazinyl, N-methyl-piperazinyl, N-acetyl-piperazinyl, oxo-piperazinyl (preferably 3-oxo-piperazin-1-yl), piperidyl, oxazolidinyl, thiazolidinyl, azepanyl, methoxy-piperidinyl and the like, preferably pyrrolidinyl, morpholinyl, piperazinyl, N-methyl-piperazinyl, N-acetyl-piperazinyl, oxo-piperazinyl, piperidyl, azepanyl, and methoxy-piperidinyl.

The term "aryl" as used herein means a mono- or bicyclic aromatic ring with 6 to 10 ring carbon atoms. Examples of such aryl groups are phenyl and naphthyl, preferably phenyl.

In a particular preferred embodiment, the aryl that is "optionally substituted one or more times" is preferably optionally substituted one to five times, more preferably one to three times, and more preferably one or two times. If such aryl is substituted by 2,4-dioxa-pentan-1,5-diyl or 2,5-dioxa-hexan-1,6-diyl, such aryl is preferably a phenyl that is preferably substituted one time by 2,4-dioxa-pentan-1,5-diyl or 2,5-dioxa-hexan-1,6-diyl and forms together with the 2,4-dioxa-pentan-1,5-diyl or the 2,5-dioxa-hexan-1,6-diyl substituent a benzo[1,3]dioxolyl or a 2,3-dihydro-benzo[1,4]dioxinyl moiety.

In a particular preferred embodiment, the term "heteroaryl" means a mono- or bicyclic aromatic ring with 5 to 10 ring atoms, preferably 5 to 6 ring atoms, which contains up to 3, preferably 1 or 2 heteroatoms selected independently from the group consisting of N, O and S with the remaining ring atoms being carbon atoms. Examples of such heteroaryl groups include pyrrolyl, imidazolyl, pyrazolyl, triazolyl, tetrazolyl, furanyl, oxazolyl, isoxazolyl, thienyl, thiazolyl, pyridyl, pyrimidyl, pyridazinyl, pyrazinyl, indolyl, indazolyl, benzimidazolyl, benzothiophenyl, benzofuranyl, quinolyl, isoquinolyl, quinazolinyl, quinoxalinyl and the like, preferably pyrrolyl, imidazolyl, pyrazolyl, triazolyl, tetrazolyl, furanyl, oxazolyl, isoxazolyl, thienyl, thiazolyl, pyridyl, pyrimidyl, pyridazinyl, pyrazinyl, indolyl, indazolyl, benzimidazolyl, benzothiophenyl, benzofuranyl, quinolyl, isoquinolyl or quinazolinyl, more preferably furanyl, isoxazolyl, thienyl, pyridyl, pyrazinyl, benzofuranyl, or quinoxalinyl, and more preferably pyridyl.

If Y is —NH— or —N(alkyl)-, and R$^6$ is alkyl, then said alkyl is preferably substituted once with a substituent selected from the group consisting of halogen, hydroxy, alkoxy, alkoxyalkoxy, amino, alkylamino, dialkylamino, —C(O)OH and —C(O)NH$_2$.

If Y is —O—, and R$^6$ is alkyl, then said alkyl is preferably substituted once with a substituent selected from the group consisting of halogen, hydroxy, alkoxyalkoxy, amino, alkylamino, dialkylamino, —C(O)OH and —C(O)NH$_2$.

If Z is —C(O)NR$^7$ or —S(O)$_2$NR$^7$—, and R$^4$ is heteroaryl-V— or heterocyclyl-V— and V is a single bond, the heteroaryl or heterocyclyl group is preferably not connected via a ring heteroatom to Z, but via a carbon atom of the heteroaryl or heterocyclyl group.

In a particular preferred embodiment, R$^1$ is hydrogen or alkyl, preferably R$^1$ is alkyl.

In a particular preferred embodiment R$^2$ is hydrogen or alkyl, preferably alkyl.

In a particular preferred embodiment R$^3$ is hydrogen or alkyl, preferably alkyl.

In a particular preferred embodiment, R$^2$ and R$^3$ form together with the carbon atom to which they are attached a (C$_5$-C$_6$)cycloalkyl ring.

Preferably R$^2$ and R$^3$ are both alkyl.

Z is preferably —C(O)—, —C(O)NR$^7$—, —C(O)O— or —S(O)$_2$—.

n is preferably 1.

In a particular preferred embodiment R$^4$ is hydrogen or alkyl, wherein the alkyl is optionally substituted one or more times, preferably one to three times by halogen, or one or two times by hydroxy, alkoxy, alkoxyalkoxy, amino, alkylamino or dialkylamino; and more preferably substituted by halogen (preferably fluorine or chlorine), alkoxy or dialkylamino; with the proviso that R$^4$ is not hydrogen, if n is 1 and Z is —C(O)O—.

In a particular preferred embodiment R$^4$ is aryl-V—, wherein the aryl is optionally substituted one or several times by halogen, cyano, nitro, amino, alkylamino, dialkylamino, 2,4-dioxa-pentan-1,5-diyl, 2,5-dioxa-hexan-1,6-diyl, hydroxy, (C$_1$-C$_4$)alkyl, (C$_1$-C$_4$)alkoxy, halogenated (C$_1$-C$_4$) alkyl or halogenated (C$_1$-C$_4$)alkoxy.

In a particular preferred embodiment R$^4$ is heteroaryl-V—, wherein the heteroaryl is optionally substituted one or more times, preferably one or two times by alkyl.

In a particular preferred embodiment R$^4$ is cycloalkyl-V—.

In a particular preferred embodiment R$^4$ is heterocyclyl-V—; with the proviso that R$^4$ is not hydrogen, if n is 1 and Z is —C(O)O—.

V is preferably a single bond or alkylene.

R$^5$ is preferably hydrogen or alkyl and more preferably hydrogen.

X is preferably a single bond.

As used herein, in relation to mass spectrometry (MS) the term "API+" refers to positive atmospheric pressure ionization mode and the term "API−" refers to negative atmospheric pressure ionization mode.

As used herein, in relation to nuclear magnetic resonance (NMR) the term "D$_6$-DMSO" refers to deuterated dimethylsulfoxide and the term "CD$_3$CN" refers to deuterated acetonitrile.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Bastin, R. J., et al., Organic Proc. Res. Dev. 4 (2000) 427-435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases (HPLC: High Performance Liquid Chromatography) which are commercially available.

The compounds of formula I can exist in different tautomeric forms and in variable mixtures thereof. All tautomeric forms of the compounds of formula I and mixtures thereof are an objective of the invention. For example, the imidazole part of the tricyclic ring system of formula I can exist in two tautomeric forms as shown here below:

(c) aryl-V—, wherein the aryl is optionally substituted one or more times by halogen, cyano, nitro, amino, hydroxy, $(C_1-C_4)$alkyl, $(C_1-C_4)$alkoxy, halogenated $(C_1-C_4)$alkyl or halogenated $(C_1-C_4)$alkoxy;
(d) heteroaryl-V—, wherein the heteroaryl is optionally substituted one or more times by alkyl;
(e) cycloalkyl-V—; and
(f) heterocyclyl-V—;
with the proviso that $R^4$ is not hydrogen, if n is 1 and Z is —C(O)O—.

Another embodiment of the invention are the compounds according to formula I, wherein
(a) $R^1$ is hydrogen or alkyl;
(b) $R^2$ is alkyl;
(c) $R^3$ is alkyl;
(d) Z is —C(O)—, —C(O)NR$^7$—, —C(O)O— or —S(O)$_2$—;
(e) $R^4$ is selected from the group consisting of:
  (1) hydrogen;
  (2) alkyl, wherein the alkyl is optionally substituted one or more times by halogen, alkoxy or dialkylamino;
  (3) aryl-V—, wherein the aryl is optionally substituted one or more times by halogen, cyano, 2,4-dioxa-pentan-1,5-diyl, 2,5-dioxa-hexan-1,6-diyl, $(C_1-C_4)$alkyl, $(C_1-C_4)$alkoxy or halogenated $(C_1-C_4)$alkyl;
  (4) heteroaryl-V—, wherein the heteroaryl is optionally substituted one or more times by alkyl;
  (5) cycloalkyl-V—; and
  (6) heterocyclyl-V—;
with the proviso that $R^4$ is not hydrogen, if n is 1 and Z is —C(O)O—;
(f) $R^5$ is hydrogen or alkyl; and
(g) X is a single bond.

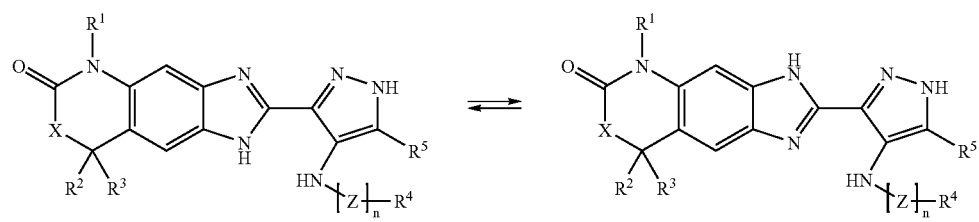

formula I

Also, e.g. the pyrazole ring of formula I can form two tautomeric forms as shown here below:

Another embodiment of the invention are the compounds according to formula I, wherein:

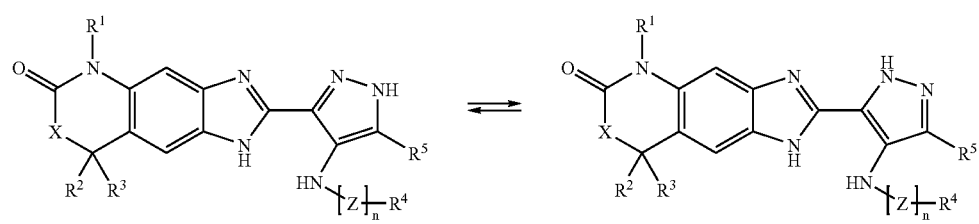

formula I

An embodiment of the invention are the compounds according to formula I, wherein V is a single bond or alkylene and $R^4$ is selected from the group consisting of:
(a) hydrogen;
(b) alkyl, which is optionally substituted one or more times by halogen, hydroxy, alkoxy, alkoxyalkoxy, amino, alkylamino, or dialkylamino;

(a) $R^1$, $R^2$ and $R^3$ are alkyl;
(b) Z is —C(O)—, —C(O)NR$^7$—, —C(O)O— or —S(O)$_2$—;
(c) n is 1;
(d) $R^4$ is selected from the group consisting of:
  (1) alkyl, wherein the alkyl is optionally substituted one or more times by halogen, alkoxy or dialkylamino;

(2) aryl-V—, wherein the aryl is optionally substituted one or more times by halogen, cyano, 2,4-dioxa-pentan-1,5-diyl, 2,5-dioxa-hexan-1,6-diyl, ($C_1$-$C_4$)alkyl, ($C_1$-$C_4$)alkoxy or halogenated ($C_1$-$C_4$)alkyl;

(3) heteroaryl-V—, wherein the heteroaryl is optionally substituted one or more times by alkyl;

(4) cycloalkyl-V—; and (5) heterocyclyl-V—;

(e) $R^5$ is hydrogen; and (f) X is a single bond.

Another embodiment of the invention are the compounds according to formula I, wherein n is 1.

Another embodiment of the invention are the compounds according to formula I, wherein Z is —C(O)— or —C(O)$NR^7$—; and n is 1.

Another embodiment of the invention are the compounds according to formula I, wherein Z is —C(O)O—, —S(O)$_2$— or —S(O)$_2$$NR^7$—; and n is 1.

Another embodiment of the invention are the compounds according to formula I, wherein Z is —C(O)—; and n is 1.

Another embodiment of the invention are the compounds according to formula I, wherein:

(a) $R^1$, $R^2$ and $R^3$ are alkyl;

(b) Z is —C(O)—;

(c) n is 1;

(d) $R^4$ is selected from the group consisting of:

(1) alkyl, which is optionally substituted one or more times by halogen or alkoxy;

(2) aryl-V—, wherein the aryl is optionally substituted one or more times by halogen, cyano, 2,4-dioxa-pentan-1,5-diyl, 2,5-dioxa-hexan-1,6-diyl, ($C_1$-$C_4$)alkyl, ($C_1$-$C_4$)alkoxy or halogenated ($C_1$-$C_4$)alkyl;

(3) heteroaryl-V—, wherein the heteroaryl is optionally substituted one or more times by alkyl;

(4) cycloalkyl-V—; and (5) heterocyclyl-V—;

(e) $R^5$ is hydrogen or alkyl; and (f) X is a single bond.

Another embodiment of the invention are the compounds according to formula I, wherein:

(a) $R^1$, $R^2$ and $R^3$ are alkyl;

(b) Z is —C(O)—;

(c) n is 1;

(d) $R^4$ is alkyl, which is optionally substituted one or more times by halogen or alkoxy;

(e) $R^5$ is hydrogen or alkyl; and (f) X is a single bond.

Such compounds, for example, may be selected from the group consisting of:

N-[3-(5-Ethyl-7,7-dimethyl-6-oxo-1,5,6,7-tetrahydro-imidazo[4,5-f]indol-2-yl)-1H-pyrazol-4-yl]-propionamide;

N-[3-(7,7-Dimethyl-6-oxo-1,5,6,7-tetrahydro-imidazo[4,5-f]indol-2-yl)-5-methyl-1H-pyrazol-4-yl]-acetamide;

N-[3-(7,7-Dimethyl-6-oxo-1,5,6,7-tetrahydro-imidazo[4,5-f]indol-2-yl)-1H-pyrazol-4-yl]-acetamide;

N-[3-(5-Ethyl-7,7-dimethyl-6-oxo-1,5,6,7-tetrahydro-imidazo[4,5-f]indol-2-yl)-1H-pyrazol-4-yl]-acetamide;

N-[3-(5-Ethyl-7,7-dimethyl-6-oxo-1,5,6,7-tetrahydro-imidazo[4,5-f]indol-2-yl)-1H-pyrazol-4-yl]-2,2,2-trifluoroacetamide;

N-[3-(5-Ethyl-7,7-dimethyl-6-oxo-1,5,6,7-tetrahydro-imidazo[4,5-f]indol-2-yl)-1H-pyrazol-4-yl]-3,3-dimethyl-butyramide;

N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-propionamide;

2-Ethyl-N-[3-(5-ethyl-7,7-dimethyl-6-oxo-1,5,6,7-tetrahydro-imidazo[4,5-f]indol-2-yl)-1H-pyrazol-4-yl]-butyramide;

N-[3-(5-Ethyl-7,7-dimethyl-6-oxo-1,5,6,7-tetrahydro-imidazo[4,5-f]indol-2-yl)-1H-pyrazol-4-yl]-3-methyl-butyramide;

3-Chloro-N-[3-(5-ethyl-7,7-dimethyl-6-oxo-1,5,6,7-tetrahydro-imidazo[4,5-f]indol-2-yl)-1H-pyrazol-4-yl]-2,2-dimethyl-propionamide;

N-[3-(5-Ethyl-7,7-dimethyl-6-oxo-1,5,6,7-tetrahydro-imidazo[4,5-f]indol-2-yl)-1H-pyrazol-4-yl]-2-methoxy-acetamide; and N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-butyramide.

Another embodiment of the invention are the compounds according to formula I, wherein:

(a) $R^1$, $R^2$ and $R^3$ are alkyl;

(b) Z is —C(O)—;

(c) n is 1;

(d) $R^4$ is aryl-V—, wherein the aryl is optionally substituted one or more times by halogen, cyano, 2,4-dioxapentan-1,5-diyl, 2,5-dioxa-hexan-1,6-diyl, ($C_1$-$C_4$) alkyl, ($C_1$-$C_4$)alkoxy or halogenated ($C_1$-$C_4$)alkyl;

(e) $R^5$ is hydrogen; and (f) X is a single bond.

Such compounds, for example, may be selected from the group consisting of:

N-[3-(5-Ethyl-7,7-dimethyl-6-oxo-1,5,6,7-tetrahydro-imidazo[4,5-f]indol-2-yl)-1H-pyrazol-4-yl]-2,6-difluoro-benzamide;

N-[3-(5-Ethyl-7,7-dimethyl-6-oxo-1,5,6,7-tetrahydro-imidazo[4,5-f]indol-2-yl)-1H-pyrazol-4-yl]-benzamide;

N-[3-(5-Ethyl-7,7-dimethyl-6-oxo-1,5,6,7-tetrahydro-imidazo[4,5-f]indol-2-yl)-1H-pyrazol-4-yl]-4-fluoro-benzamide;

N-[3-(5-Ethyl-7,7-dimethyl-6-oxo-1,5,6,7-tetrahydro-imidazo[4,5-f]indol-2-yl)-1H-pyrazol-4-yl]-2-phenyl-acetamide;

N-[3-(5-Ethyl-7,7-dimethyl-6-oxo-1,5,6,7-tetrahydro-imidazo[4,5-f]indol-2-yl)-1H-pyrazol-4-yl]-3-phenyl-propionamide;

N-[3-(5-Ethyl-7,7-dimethyl-6-oxo-1,5,6,7-tetrahydro-imidazo[4,5-f]indol-2-yl)-1H-pyrazol-4-yl]-2-phenyl-butyramide;

3-Cyano-N-[3-(5-ethyl-7,7-dimethyl-6-oxo-1,5,6,7-tetrahydro-imidazo[4,5-f]indol-2-yl)-1H-pyrazol-4-yl]-benzamide;

N-[3-(5-Ethyl-7,7-dimethyl-6-oxo-1,5,6,7-tetrahydro-imidazo[4,5-f]indol-2-yl)-1H-pyrazol-4-yl]-3-trifluoromethyl-benzamide;

N-[3-(5-Ethyl-7,7-dimethyl-6-oxo-1,5,6,7-tetrahydro-imidazo[4,5-f]indol-2-yl)-1H-pyrazol-4-yl]-2,6-dimethoxy-benzamide;

3-Chloro-N-[3-(5-ethyl-7,7-dimethyl-6-oxo-1,5,6,7-tetrahydro-imidazo[4,5-f]indol-2-yl)-1H-pyrazol-4-yl]-benzamide;

N-[3-(5-Ethyl-7,7-dimethyl-6-oxo-1,5,6,7-tetrahydro-imidazo[4,5-f]indol-2-yl)-1H-pyrazol-4-yl]-3-methyl-benzamide;

N-[3-(5-Ethyl-7,7-dimethyl-6-oxo-1,5,6,7-tetrahydro-imidazo[4,5-f]indol-2-yl)-1H-pyrazol-4-yl]-2-phenoxy-acetamide;

N-[3-(5-Ethyl-7,7-dimethyl-6-oxo-1,5,6,7-tetrahydro-imidazo[4,5-f]indol-2-yl)-1H-pyrazol-4-yl]-4-fluoro-3-methyl-benzamide;

N-[3-(5-Ethyl-7,7-dimethyl-6-oxo-1,5,6,7-tetrahydro-imidazo[4,5-f]indol-2-yl)-1H-pyrazol-4-yl]-3,4-difluoro-benzamide;
2-Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide;
N-[3-(5-Ethyl-7,7-dimethyl-6-oxo-1,5,6,7-tetrahydro-imidazo[4,5-f]indol-2-yl)-1H-pyrazol-4-yl]-3,4,5-trimethoxy-benzamide;
N-[3-(5-Ethyl-7,7-dimethyl-6-oxo-1,5,6,7-tetrahydro-imidazo[4,5-f]indol-2-yl)-1H-pyrazol-4-yl]-3,5-difluoro-benzamide;
(E)-N-[3-(5-Ethyl-7,7-dimethyl-6-oxo-1,5,6,7-tetrahydro-imidazo[4,5-f]indol-2-yl)-1H-pyrazol-4-yl]-3-phenyl-acrylamide;
N-[3-(5-Ethyl-7,7-dimethyl-6-oxo-1,5,6,7-tetrahydro-imidazo[4,5-f]indol-2-yl)-1H-pyrazol-4-yl]-2-phenoxy-propionamide;
N-[3-(5-Ethyl-7,7-dimethyl-6-oxo-1,5,6,7-tetrahydro-imidazo[4,5-f]indol-2-yl)-1H-pyrazol-4-yl]-2-(2-methoxy-phenoxy)-acetamide;
Benzo[1,3]dioxole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide;
2,3-Dihydro-benzo[1,4]dioxine-6-carboxylic acid[3-(5-ethyl-7,7-dimethyl-6-oxo-1,5,6,7-tetrahydro-imidazo[4,5-f]indol-2-yl)-1H-pyrazol-4-yl]-amide;
1-Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide;
3,5-Diethoxy-N-[3-(5-ethyl-7,7-dimethyl-6-oxo-1,5,6,7-tetrahydro-imidazo[4,5-f]indol-2-yl)-1H-pyrazol-4-yl]-benzamide;
[3-(5-Ethyl-7,7-dimethyl-6-oxo-1,5,6,7-tetrahydro-imidazo[4,5-f]indol-2-yl)-1H-pyrazol-4-yl]-carbamic acid benzyl ester;
N-[3-(5-Ethyl-7,7-dimethyl-6-oxo-1,5,6,7-tetrahydro-imidazo[4,5-f]indol-2-yl)-1H-pyrazol-4-yl]-3,4,5-trifluoro-benzamide; and
N-[3-(5-Ethyl-7,7-dimethyl-6-oxo-1,5,6,7-tetrahydro-imidazo[4,5-f]indol-2-yl)-1H-pyrazol-4-yl]-3,5-dimethoxy-benzamide.

Another embodiment of the invention are the compounds according to formula I, wherein:
(a) $R^1$, $R^2$ and $R^3$ are alkyl;
(b) Z is —C(O)—;
(c) n is 1;
(d) $R^4$ is heteroaryl-V—, wherein the heteroaryl is optionally substituted one or more times by alkyl;
(e) V is a single bond or alkylene;
(f) $R^5$ is hydrogen; and
(g) X is a single bond.

Such compounds, for example, may be selected from the group consisting of:
N-[3-(5-Ethyl-7,7-dimethyl-6-oxo-1,5,6,7-tetrahydro-imidazo[4,5-f]indol-2-yl)-1H-pyrazol-4-yl]-isonicotinamide;
N-[3-(5-Ethyl-7,7-dimethyl-6-oxo-1,5,6,7-tetrahydro-imidazo[4,5-f]indol-2-yl)-1H-pyrazol-4-yl]-nicotinamide;
N-[3-(5-Ethyl-7,7-dimethyl-6-oxo-1,5,6,7-tetrahydro-imidazo[4,5-f]indol-2-yl)-1H-pyrazol-4-yl]-2-thiophen-2-yl-acetamide;
Isoxazole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Furan-2-carboxylic acid[3-(5-ethyl-7,7-dimethyl-6-oxo-1,5,6,7-tetrahydro-imidazo[4,5-f]indol-2-yl)-1H-pyrazol-4-yl]-amide
Thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Quinoxaline-2-carboxylic acid[3-(5-ethyl-7,7-dimethyl-6-oxo-1,5,6,7-tetrahydro-imidazo[4,5-f]indol-2-yl)-1H-pyrazol-4-yl]-amide;
5-Methyl-thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Pyrazine-2-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Benzofuran-2-carboxylic acid[3-(5-ethyl-7,7-dimethyl-6-oxo-1,5,6,7-tetrahydro-imidazo[4,5-f]indol-2-yl)-1H-pyrazol-4-yl]-amide;
5-Methyl-1H-pyrazole-3-carboxylic acid[3-(5-ethyl-7,7-dimethyl-6-oxo-1,5,6,7-tetrahydro-imidazo[4,5-f]indol-2-yl)-1H-pyrazol-4-yl]-amide; and
Furan-2-carboxylic acid[3-(5-isopropyl-7,7-dimethyl-6-oxo-1,5,6,7-tetrahydro-imidazo[4,5-f]indol-2-yl)-1H-pyrazol-4-yl]-amide.

Another embodiment of the invention are the compounds according to formula I, wherein:
(a) $R^1$, $R^2$ and $R^3$ are alkyl;
(b) Z is —C(O)—;
(c) n is 1;
(d) $R^4$ is cycloalkyl-V—;
(e) V is a single bond or alkylene;
(f) $R^5$ is hydrogen; and
(g) X is a single bond.

Such compounds, for example, may be selected from the group consisting of:
Cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide;
Cyclohexanecarboxylic acid[3-(5-ethyl-7,7-dimethyl-6-oxo-1,5,6,7-tetrahydro-imidazo[4,5-f]indol-2-yl)-1H-pyrazol-4-yl]-amide;
Cyclopentanecarboxylic acid[3-(5-ethyl-7,7-dimethyl-6-oxo-1,5,6,7-tetrahydro-imidazo[4,5f]indol-2-yl)-1H-pyrazol-4-yl]-amide;
3-Cyclopentyl-N-[3-(5-ethyl-7,7-dimethyl-6-oxo-1,5,6,7-tetrahydro-imidazo[4,5-f]indol-2-yl)-1H-pyrazol-4-yl]-propionamide;
2-Cyclopentyl-N-[3-(5-ethyl-7,7-dimethyl-6-oxo-1,5,6,7-tetrahydro-imidazo[4,5-f]indol-2-yl)-1H-pyrazol-4-yl]-acetamide;
1-Methyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide;
Cyclopropanecarboxylic acid[3-(5-isopropyl-7,7-dimethyl-6-oxo-1,5,6,7-tetrahydro-imidazo[4,5-f]indol-2-yl)-1H-pyrazol-4-yl]-amide;
Cyclopropanecarboxylic acid[3-(5,7,7-triethyl-6-oxo-1,5,6,7-tetrahydro-imidazo[4,5-f]indol-2-yl)-1H-pyrazol-4-yl]-amide;
1-Methyl-cyclopropanecarboxylic acid[3-(5-isopropyl-7,7-dimethyl-6-oxo-3,5,6,7-tetrahydro-imidazo[4,5-f indol-2-yl)-1H-pyrazol-4-yl]-amide;
Cyclopropanecarboxylic acid[3-(7,7-diethyl-5-isopropyl-6-oxo-1,5,6,7-tetrahydro-imidazo[4,5-f]indol-2-yl)-1H-pyrazol-4-yl]-amide; and
1-Methyl-cyclopropanecarboxylic acid[3-(7,7-diethyl-5-isopropyl-6-oxo-1,5,6,7-tetrahydro-imidazo[4,5-f]indol-2-yl)-1H-pyrazol-4-yl]-amide.

Another embodiment of the invention are the compounds according to formula I, wherein:

(a) R¹, R² and R³ are alkyl;
(b) Z is —C(O)—;
(c) n is 1;
(d) R⁴ is heterocyclyl-V—;
(e) V is a single bond;
(f) R⁵ is hydrogen; and
(g) X is a single bond.

Such compounds, for example, may be selected from the group consisting of:

Morpholine-4-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Piperidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
4-Methyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
4-Acetyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Pyrrolidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
3-Oxo-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
Azepane-1-carboxylic acid[3-(5-ethyl-7,7-dimethyl-6-oxo-1,5,6,7-tetrahydro-imidazo[4,5-f]indol-2-yl)-1H-pyrazol-4-yl]-amide;
4-Methoxy-piperidine-1-carboxylic acid[3-(7,7-dimethyl-6-oxo-1,5,6,7-tetrahydro-imidazo[4,5-f]indol-2-yl)-1H-pyrazol-4-yl]-amide;
Piperidine-1-carboxylic acid[3-(5-isopropyl-7,7-dimethyl-6-oxo-3,5,6,7-tetrahydro-imidazo[4,5-f]indol-2-yl)-1H-pyrazol-4-yl]-amide;
Piperidine-1-carboxylic acid[3-(7,7-diethyl-5-isopropyl-6-oxo-1,5,6,7-tetrahydro-imidazo[4,5-f]indol-2-yl)-1H-pyrazol-4-yl]-amide;
Azepane-1-carboxylic acid[3-(5-isopropyl-7,7-dimethyl-6-oxo-3,5,6,7-tetrahydro-imidazo[4,5-f]indol-2-yl)-1H-pyrazol-4-yl]-amide; and
Azepane-1-carboxylic acid[3-(7,7-diethyl-5-isopropyl-6-oxo-1,5,6,7-tetrahydro-imidazo[4,5-f]indol-2-yl)-1H-pyrazol-4-yl]-amide.

Or such compounds, for example, may be selected from the group consisting of:

Oxetane-3-carboxylic acid[3-(5-isopropyl-7,7-dimethyl-6-oxo-1,5,6,7-tetrahydro-imidazo[4,5-f]indol-2-yl)-1H-pyrazol-4-yl]-amide;
Oxetane-3-carboxylic acid[3-(5-isopropyl-7,7-ethyl-6-oxo-1,5,6,7-tetrahydro-imidazo[4,5-f]indol-2-yl)-1H-pyrazol-4-yl]-amide; and
Oxetane-3-carboxylic acid[3-(5,7,7-triethyl-6-oxo-1,5,6,7-tetrahydro-imidazo[4,5-f]indol-2-yl)-1H-pyrazol-4-yl]-amide.

Another embodiment of the invention are the compounds according to formula I, wherein Z is —C(O)NR⁷—; and n is 1.

Another embodiment of the invention are the compounds according to formula I, wherein:
(a) R¹, R² and R³ are alkyl;
(b) Z is —C(O)NR⁷—;
(c) n is 1;
(d) R⁴ is selected from the group consisting of:
    (1) alkyl, which is optionally substituted one or more times by dialkylamino; and
    (2) aryl-V—;
(e) V is alkylene;
(f) R⁵ is hydrogen; and
(g) X is a single bond.

Such compounds, for example, may be selected from the group consisting of:

1-Benzyl-3-[3-(5-ethyl-7,7-dimethyl-6-oxo-1,5,6,7-tetrahydro-imidazo[4,5-f]indol-2-yl)-1H-pyrazol-4-yl]-urea;
1,1-Diethyl-3-[3-(5-ethyl-7,7-dimethyl-6-oxo-1,5,6,7-tetrahydro-imidazo[4,5-f]indol-2-yl)-1H-pyrazol-4-yl]-urea;
3-[3-(5-Ethyl-7,7-dimethyl-6-oxo-1,5,6,7-tetrahydro-imidazo[4,5-f]indol-2-yl)-1H-pyrazol-4-yl]-1,1-dimethyl-urea;
1-Benzyl-3-[3-(5-ethyl-7,7-dimethyl-6-oxo-1,5,6,7-tetrahydro-imidazo[4,5-f]indol-2-yl)-1H-pyrazol-4-yl]-1-isopropyl-urea;
1-(2-Dimethylamino-ethyl)-1-ethyl-3-[3-(5-ethyl-7,7-dimethyl-6-oxo-1,5,6,7-tetrahydro-imidazo[4,5-f]indol-2-yl)-1H-pyrazol-4-yl]-urea;
1-(2-Diethylamino-ethyl)-3-[3-(5-ethyl-7,7-dimethyl-6-oxo-1,5,6,7-tetrahydro-imidazo[4,5-f]indol-2-yl)-1H-pyrazol-4-yl]-1-methyl-urea;
1,1-Diethyl-3-[3-(5-isopropyl-7,7-dimethyl-6-oxo-1,5,6,7-tetrahydro-imidazo[4,5-f]indol-2-yl)-1H-pyrazol-4-yl]-urea;
3-[3-(5-Ethyl-7,7-dimethyl-6-oxo-1,5,6,7-tetrahydro-imidazo[4,5-f]indol-2-yl)-1H-pyrazol-4-yl]-1,1-diisopropyl-urea; and
3-[3-(7,7-Diethyl-5-isopropyl-6-oxo-1,5,6,7-tetrahydro-imidazo[4,5-f]indol-2-yl)-1H-pyrazol-4-yl]-1,1-diethyl-urea.

Another embodiment of the invention are the compounds according to formula I, wherein Z is —C(O)O—; and n is 1.

Another embodiment of the invention are the compounds according to formula I, wherein:
(a) R¹ is hydrogen or alkyl;
(b) R² is alkyl;
(c) R³ is alkyl;
(d) Z is —C(O)O—;
(e) R⁴ is selected from the group consisting of:
    (1) alkyl, which is optionally substituted one or more times by alkoxy;
    (2) aryl-V—, wherein the aryl is optionally substituted one or more times by halogen, preferably chlorine; and
    (3) cycloalkyl-V—;
(f) V is a single bond or alkylene;
(g) R⁵ is hydrogen; and
(h) X is a single bond.

Such compounds, for example, may be selected from the group consisting of:

3-(7,7-Dimethyl-6-oxo-1,5,6,7-tetrahydro-imidazo[4,5-f]indol-2-yl)-1H-pyrazol-4-yl]-carbamic acid benzyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid methyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid phenyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid ethyl ester;

[3-(5-Ethyl-7,7-dimethyl-6-oxo-1,5,6,7-tetrahydro-imidazo[4,5-f]indol-2-yl)-1H-pyrazol-4-yl]-carbamic acid 2,2-dimethyl-propyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid 2-chloro-benzyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid isobutyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid 2-methoxy-ethyl ester; and
[3-(5-Ethyl-7,7-dimethyl-6-oxo-1,5,6,7-tetrahydro-imidazo[4,5-f]indol-2-yl)-1H-pyrazol-4-yl]-carbamic acid isopropyl ester.

Another embodiment of the invention are the compounds according to formula I, wherein:
(a) $R^1$, $R^2$ and $R^3$ are alkyl;
(b) Z is —C(O)O—;
(c) $R^4$ is heterocyclyl-V—;
(d) V is a single bond;
(e) $R^5$ is hydrogen; and
(f) X is a single bond.

Such compounds, for example, may be selected from the group consisting of:
[3-(5-Isopropyl-7,7-dimethyl-6-oxo-1,5,6,7-tetrahydro-imidazo[4,5-f]indol-2-yl)-1H-pyrazol-4-yl]-carbamic acid oxetan-3-yl ester;
[3-(5-Isopropyl-7,7-ethyl-6-oxo-1,5,6,7-tetrahydro-imidazo[4,5-f]indol-2-yl)-1H-pyrazol-4-yl]-carbamic acid oxetan-3-yl ester; and
[3-(5,7,7-triethyl-6-oxo-1,5,6,7-tetrahydro-imidazo[4,5-f]indol-2-yl)-1H-pyrazol-4-yl]-carbamic acid oxetan-3-yl ester.

Another embodiment of the invention are the compounds according to formula I, wherein Z is —S(O)$_2$—; and n is 1.

Another embodiment of the invention are the compounds according to formula I, wherein:
(a) $R^1$ is hydrogen or alkyl;
(b) $R^2$ is alkyl;
(c) $R^3$ is alkyl;
(d) Z is —S(O)$_2$—;
(e) n is 1;
(f) $R^4$ is alkyl or aryl-V—;
(g) V is a single bond;
(h) $R^5$ is hydrogen; and
(i) X is a single bond.

Such compounds, for example, may be selected from the group consisting of:
N-[3-(7,7-Dimethyl-6-oxo-1,5,6,7-tetrahydro-imidazo[4,5-f]indol-2-yl)-1H-pyrazol-4-yl]-benzenesulfonamide; and
N-[3-(5-Ethyl-7,7-dimethyl-6-oxo-3,5,6,7-tetrahydro-imidazo[4,5-f]indol-2-yl)-1H-pyrazol-4-yl]-methanesulfonamide.

Another embodiment of the invention are the compounds according to formula I, wherein Z is —S(O)$_2$NR$^7$—; and n is 1.

Another embodiment of the invention are the compounds according to formula I, wherein:
(a) n is 0; and
(b) $R^4$ is alkyl, which is optionally substituted one or more times by halogen, hydroxy, alkoxy, alkoxyalkoxy, amino, alkylamino or dialkylamino.

Another embodiment of the invention are the compounds according to formula I, wherein:
(a) $R^1$ is hydrogen or alkyl;
(b) $R^2$ is alkyl;
(c) $R^3$ is alkyl;
(d) n is 0;
(e) $R^4$ is hydrogen, alkyl or aryl-V—;
(f) V is a single bond;
(g) $R^5$ is hydrogen or alkyl; and
(h) X is a single bond.

Such compounds, for example, may be selected from the group consisting of:
5-Ethyl-2-(4-ethylamino-1H-pyrazol-3-yl)-7,7-dimethyl-5,7-dihydro-1H-imidazo[4,5-f]indol-6-one;
2-(4-Benzylamino-5-methyl-1H-pyrazol-3-yl)-5-ethyl-7,7-dimethyl-5,7-dihydro-1H-imidazo[4,5-f]indol-6-one;
2-(4-Amino-5-methyl-1H-pyrazol-3-yl)-7,7-dimethyl-5,7-dihydro-1H-imidazo[4,5-f]indol-6-one;
2-(4-Amino-1H-pyrazol-3-yl)-5-ethyl-7,7-dimethyl-5,7-dihydro-1H-imidazo[4,5-f]indol-6-one;
2-(4-Amino-1H-pyrazol-3-yl)-7,7-dimethyl-5,7-dihydro-1H-imidazo[4,5-f]indol-6-one;
2-(4-Amino-1H-pyrazol-3-yl)-5-isopropyl-7,7-dimethyl-5,7-dihydro-1H-imidazo[4,5-f]indol-6-one;
2-(4-Amino-5-methyl-1H-pyrazol-3-yl)-5-ethyl-7,7-dimethyl-5,7-dihydro-1H-imidazo[4,5-f]indol-6-one;
2-(4-Amino-1H-pyrazol-3-yl)-5,7,7-triethyl-5,7-dihydro-1H-imidazo[4,5-f]indol-6-one; and
2-(4-Amino-1H-pyrazol-3-yl)-7,7-diethyl-5-isopropyl-5,7-dihydro-1H-imidazo[4,5-f]indol-6-one.

Another embodiment of the invention are the compounds according to formula I, wherein:
(a) n is 1; and
(b) $R^4$ is aryl-V—, wherein the aryl is optionally substituted one or more times by halogen, cyano, nitro, amino, hydroxy, ($C_1$-$C_4$)alkyl, ($C_1$-$C_4$)alkoxy, halogenated ($C_1$-$C_4$)alkyl or halogenated ($C_1$-$C_4$)alkoxy.

Another embodiment of the invention are the compounds according to formula I, wherein:
(a) Z is —C(O)— or —C(O)NR$^7$—;
(b) n is 1; and
(c) $R^4$ is aryl-V—, wherein the aryl is optionally substituted one or more times by halogen, cyano, nitro, amino, hydroxy, ($C_1$-$C_4$)alkyl, ($C_1$-$C_4$)alkoxy, halogenated ($C_1$-$C_4$)alkyl or halogenated ($C_1$-$C_4$)alkoxy.

Another embodiment of the invention are the compounds according to formula I, wherein:
(a) Z is —C(O)O—, —S(O)$_2$— or —S(O)$_2$NR$^7$—;
(b) n is 1; and
(c) $R^4$ is aryl-V—, wherein the aryl is optionally substituted one or more times by halogen, cyano, nitro, amino, hydroxy, ($C_1$-$C_4$)alkyl, ($C_1$-$C_4$)alkoxy, halogenated ($C_1$-$C_4$)alkyl or halogenated ($C_1$-$C_4$)alkoxy.

Another embodiment of the invention are the compounds according to formula I, wherein n is 1; and $R^4$ is heteroaryl-V—, wherein the heteroaryl is optionally substituted one or more times by alkyl.

Another embodiment of the invention are the compounds according to formula I, wherein:
(a) Z is —C(O)— or —C(O)NR$^7$—;
(b) n is 1; and
(c) $R^4$ is heteroaryl-V—, wherein the heteroaryl is optionally substituted one or more times by alkyl.

Another embodiment of the invention are the compounds according to formula I, wherein:
(a) Z is —C(O)O—, —S(O)$_2$— or —S(O)$_2$NR$^7$—;
(b) n is 1; and
(c) $R^4$ is heteroaryl-V—, wherein the heteroaryl is optionally substituted one or more times by alkyl Another embodiment of the invention are the compounds according to formula I, wherein n is 1; and $R^4$ is cycloalkyl-V—.

Another embodiment of the invention are the compounds according to formula I, wherein:
(a) Z is —C(O)— or —C(O)$NR^7$—;
(b) n is 1; and
(c) $R^4$ is cycloalkyl-V—.

Another embodiment of the invention are the compounds according to formula I, wherein:
(a) Z is —C(O)O—, —S(O)$_2$— or —S(O)$_2NR^7$—;
(b) n is 1; and
(c) $R^4$ is cycloalkyl-V—.

Another embodiment of the invention are the compounds according to formula I, wherein n is 1; and $R^4$ is heterocyclyl-V—.

Another embodiment of the invention are the compounds according to formula I, wherein:
(a) Z is —C(O)— or —C(O)$NR^7$—;
(b) n is 1; and
(c) $R^4$ is heterocyclyl-V—.

Another embodiment of the invention are the compounds according to formula I, wherein
(a) Z is —C(O)O—, —S(O)$_2$— or —S(O)$_2NR^7$—;
(b) n is 1; and
(c) $R^4$ is heterocyclyl-V—.

Another embodiment of the invention are the compounds according to formula I, wherein $R^5$ is hydrogen or alkyl; and X is a single bond.

Another embodiment of the invention are the compounds according to formula I, wherein
(a) n is 0;
(b) $R^4$ is alkyl, which is optionally substituted one or more times by halogen, hydroxy, alkoxy, alkoxyalkoxy, amino, alkylamino or dialkylamino;
(c) $R^5$ is hydrogen or alkyl; and
(d) X is a single bond.

Another embodiment of the invention are the compounds according to formula I, wherein $R^5$ is hydrogen; and X is a single bond.

Another embodiment of the invention are the compounds according to formula I, wherein:
(a) n is 0;
(b) $R^4$ is alkyl, which is optionally substituted one or more times by halogen, hydroxy, alkoxy, alkoxyalkoxy, amino, alkylamino or dialkylamino;
(c) $R^5$ is hydrogen; and
(d) X is a single bond.

Another embodiment of the invention is a process for the preparation of the compounds of formula I comprising the steps of:
a) reacting a compounds of formula II:

formula II wherein X, $R^1$, $R^2$ and $R^3$ have the significance given above for formula I, with a compound of formula III:

formula III wherein $R^5$ have the significance given above for formula I and A is —OH, —Cl, —H, —OMe or hydroxybenzotriazole,
to obtain the compounds of formula IV:

formula IV wherein X, $R^1$, $R^2$, $R^3$ and $R^5$ have the significance given above for formula I, b) converting the compounds of formula IV into the corresponding amino derivatives of formula I, wherein n is 0 and $R^4$ is hydrogen, and which are named compounds of formula V:

formula V wherein X, $R^1$, $R^2$, $R^3$ and $R^5$ have the significance given above for formula I, c) optionally isolating the compounds of formula V; and
d) optionally converting the compounds of formula V into their pharmaceutically acceptable salts or esters.

Another embodiment of the invention is a process for the preparation of the compounds of formula I comprising the steps of:
a) reacting a compounds of formula II:

formula II wherein X, $R^1$, $R^2$ and $R^3$ have the significance given above for formula I, with a compound of formula III:

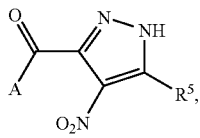

formula III wherein $R^5$ have the significance given above for formula I and A is —OH, —Cl, —H, —OMe or hydroxybenzotriazole,
to obtain the compounds of formula IV:

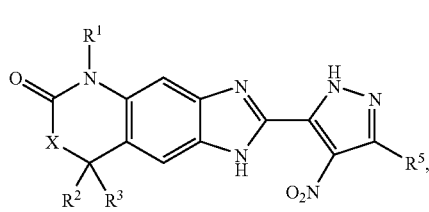

formula IV wherein X, $R^1$, $R^2$, $R^3$ and $R^5$ have the significance given above for formula I,
b) converting the compounds of formula IV into the corresponding amino derivatives of formula V:

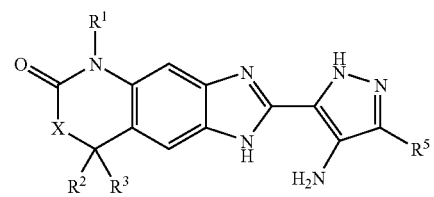

formula V wherein X, $R^1$, $R^2$, $R^3$ and $R^5$ have the significance given above for formula I,
c) converting the amino derivatives of formula V into the corresponding aminopyrazoles of formula I:

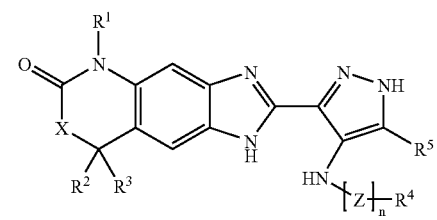

formula I wherein $R^4$ is not hydrogen if n is 0.
d) optionally isolating the compounds of formula I; and
e) optionally converting the compounds of formula I into their pharmaceutically acceptable salts or esters.

The tricyclic compounds of formula I, or a pharmaceutically acceptable salt or ester thereof, which are the subject of the present invention, may be prepared by any process known to be applicable to the preparation of chemically-related compounds. Such processes, when used to prepare a compound of the formula I, or a pharmaceutically-acceptable salt or ester thereof, are illustrated by the following representative schemes 1 to 8 and examples in which, unless otherwise stated, $R^1$, $R^2$, $R^3$, $R^4$, $R^5$, $R^6$, n, X, Y and Z have the definition previously given for formula I. Necessary starting materials are either commercially available or they may be obtained by standard procedures of organic chemistry. The preparation of such starting materials is described within the accompanying examples or in the literature cited below with respect to scheme 1 to 8. Alternatively necessary starting materials are obtainable by analogous procedures to those illustrated which are within the ordinary skill of an organic chemist.

One route for the preparation of compounds of formula I starts from the diamines of formula II:

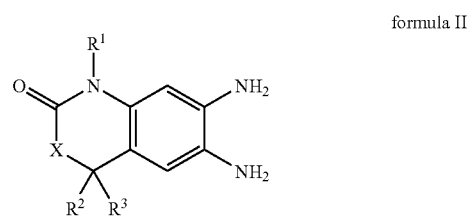

formula II

In formula II, $R^1$, $R^2$ and $R^3$ have the significance as given above for formula I.

The synthesis of diamines of formula II or precursors thereof is described in Mertens, A., et al., J. Med. Chem. 30 (1987) 1279-1287; von der Saal, W., et al., J. Med. Chem. 32 (1989) 1481-1491; U.S. Pat. Nos. 4,666,923A, 4,695,567A, 4,863,945A and 4,985,448A. For instance, the diamines of formula II, wherein A is a single bond are named IIa and can be synthesized according to U.S. Pat. No. 4,666,923A, DE 34 10 168 and Mertens, A., et al., J. Med. Chem. 30 (1987) 1279-1287 as shown in Scheme 1a:

Scheme 1a

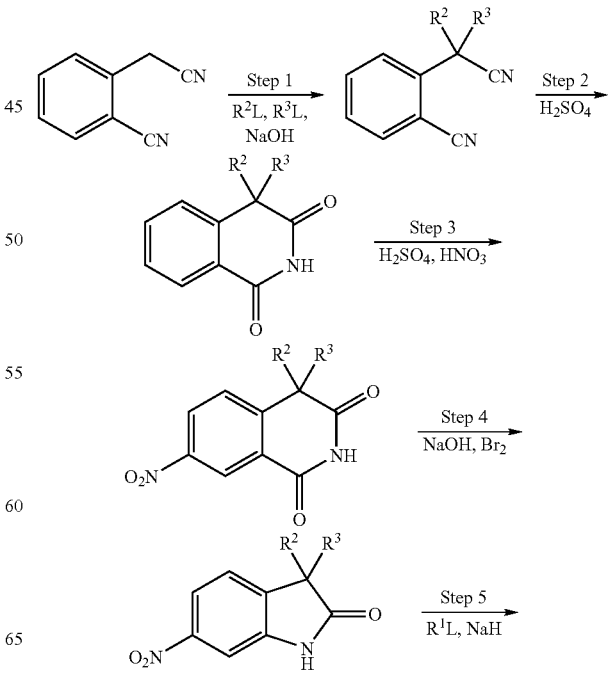

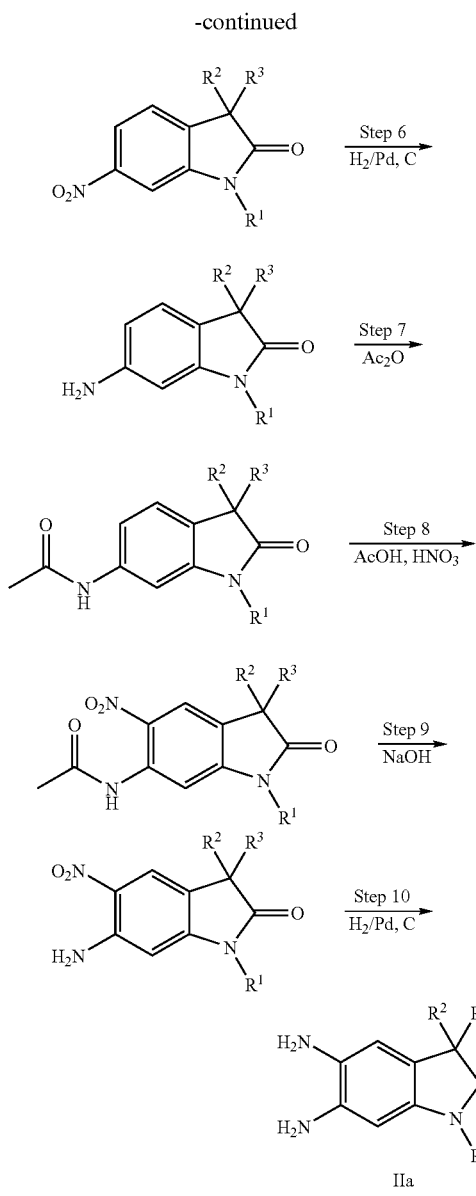

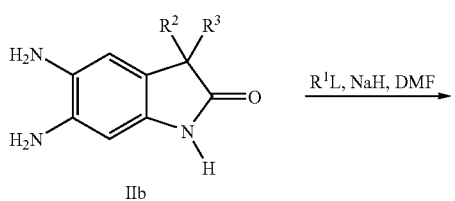

In scheme 1a, $R^1$, $R^2$ and $R^3$ have the significance as given above for formula I and L represents a leaving group such as iodine, bromine, chlorine, triflate and the like.

In an alternative procedure diamines of formula IIa can be obtained by an alkylation of diamines of formula IIb (compounds II wherein A is a single bond and $R^1$=H) as shown in scheme 1b:

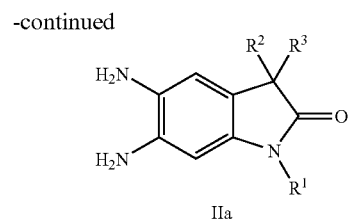

Diamines of formula IIb can be synthesized according to scheme 1 under omission of step 5.

Diamines of formula II are subsequently employed in the formation of the imidazole ring system of formula I. Different synthetic pathways for this cyclization are described in the literature (e.g. see Mertens, A., et al., J. Med. Chem. 30 (1987) 1279-1287 and U.S. Pat. No. 4,695,567A).

For example diamines of formula II (Scheme 2) can be reacted with carboxylic acids (compounds of formula III wherein A is —OH), acid chlorides (compounds of formula III wherein A is —Cl), aldehydes (compounds of formula III wherein A is —H), methyl carboxylates (compounds of formula III wherein A is —OMe) or activated esters (compounds of formula III wherein A is e.g. hydroxybenzotriazole). For detailed procedures see Mertens, A., et al., J. Med. Chem. 30 (1987) 1279-1287 and U.S. Pat. No. 4,695,567A.

Scheme 2

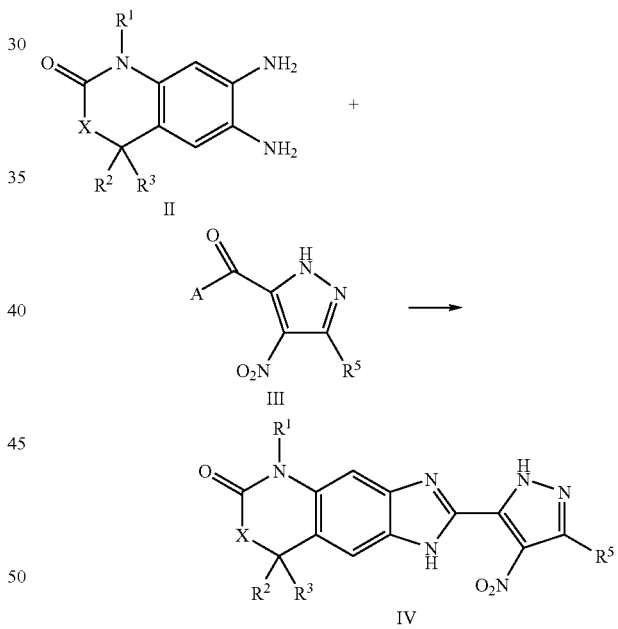

In scheme 2, $R^1$, $R^2$, $R^3$, $R^5$ and X have the significance as given above for formula I and A is —OH, —Cl, —H, —OMe or hydroxybenzotriazole.

Nitropyrazoles of formula III are either commercially available or can be prepared by different methods known to those skilled in the art. For example, if A is hydroxy the corresponding 4-nitro-3-pyrazolecarboxylic acids can be prepared by nitration of the corresponding 4-unsubstituted pyrazole carboxy compounds as described in U.S. Pat. No. 4,282,361A; DE 19 45 430; Musante, C., Gazz. Chim. Ital. 72 (1945) 121-136; and Takei, H., et al., Bull. Chem. Soc. Jpn. 52 (1979) 208-211.

Amines of the formula V (Scheme 3) can be prepared by reduction of the corresponding nitro compound of the formula IV under standard conditions, e.g. by catalytic hydrogenation in presence of usual catalyst such as palladium on activated carbon in solvents such as methanol, tetrahydrofuran or dimethylformamide at room temperature. Detailed procedures relative to reduction towards 4-aminopyrazoles and their functionalization are reported in WO 2005/002552 and WO 03/035065.

Scheme 3

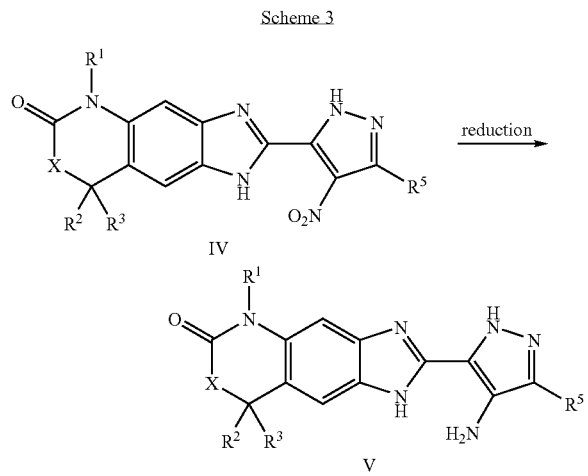

In scheme 3, $R^1$, $R^2$, $R^3$, $R^5$ and X have the significance as given above for formula I. Compounds of formula I in which n is 1 and Z is —C(O)— can be prepared using standard methods for the synthesis of amides (Scheme 4) and are named I-a. For example, such compounds can be prepared:

a) by reaction of an aminopyrazole of formula V with an acid anhydride (method A) in the presence of a base such as N,N-diisopropylethylamine, pyridine, triethyl amine and the like in an inert solvent like dichloromethane, dimethylformamide (DMF), tetrahydrofuran (THF) and the like;

b) by reaction of an aminopyrazole of formula V with an acid chloride (method B) in the presence of a base such as N,N-diisopropylethylamine, pyridine, triethyl amine and the like in an inert solvent like dichloromethane, dimethylformamide (DMF), tetrahydrofuran (THF) and the like; or c) by reaction of an aminopyrazole of formula V with every suitably activated acid (method C) in the presence of a base such as N,N-diisopropylethylamine, pyridine, triethyl amine and the like in an inert solvent like dichloromethane, dimethylformamide (DMF), tetrahydrofuran (THF) and the like.

Scheme 4

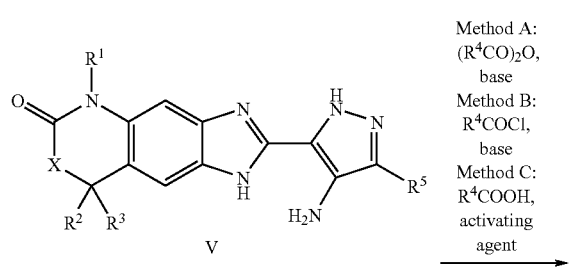

Method A: $(R^4CO)_2O$, base
Method B: $R^4COCl$, base
Method C: $R^4COOH$, activating agent -continued

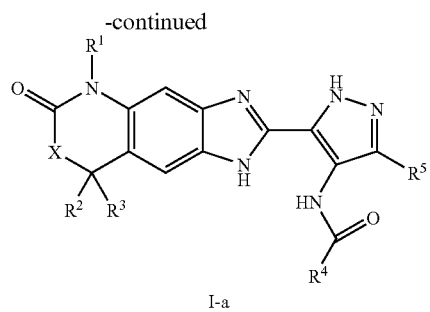

I-a

In scheme 4, $R^1$, $R^2$, $R^3$, $R^4$, $R^5$ and X have the significance as given above for formula I.

Acid anhydrides and acid chlorides used in the formation of compounds of formula I-a are either commercially available or can be prepared using standard methods well known to someone skilled in the art. Those reagents can be used in presence of base such as N,N-diisopropylethylamine, triethylamine or pyridine in inert solvent such as dichloromethane or dimethylformamide.

In scheme 4, activated acids (method C) can be prepared by different peptide coupling procedures known to those skilled in the art. Activation with those procedures can involve the use of an activating agents like 1-(3-dimethylaminopropyl)-3-ethylcarbodiimide (EDC) (or dicyclohexylcarbodiimide (DCC)), hydroxybenzotriazole (HOBt) with or without diisopropylethylamine (DIPEA) in an inert solvent such as dimethylformamide (DMF) or dichloromethane at temperatures between 0° C. and 60° C. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt) and triethylamine or di-isopropylethylamine in dimethylformamide or tetrahydrofuran.

Further nitrogens besides the amino group of compound V may be acylated under the reaction conditions shown in scheme 4. These undesired amides can be cleaved under basic conditions e.g. by treatment with a solution of ammonia in methanol and acetonitrile.

Compounds of formula I wherein n is 1 and Z is —C(O)NR$^7$— or —C(O)O— can be prepared using standard methods for the synthesis of ureas or carbamates (Scheme 5). Compounds wherein n is 1 and Z is —C(O)NR$^7$— are named I-b and compounds wherein n is 1 and —C(O)O— are named I-c. For example ureas of formula I-b can be synthesized by addition of amines of formula V to isocyanates (method D, scheme 5) in the presence of a base such as N,N-diisopropylethylamine, pyridine, triethylamine and the like in an inert solvent like dichloromethane, dimethylformamide (DMF), tetrahydrofuran (THF) and the like.

Ureas or carbamates can be obtained by reaction of the corresponding carbamoyl chlorides or chloroformates with amines of formula V (method E, scheme 5) in the presence of a base such as N,N-diisopropylethylamine, pyridine, triethyl amine and the like in an inert solvent like dichloromethane, dimethylformamide (DMF), tetrahydrofuran (THF) and the like.

In another procedure for the preparation of compounds of formula I-b or I-c an amine of formula V is reacted with carbonyldiimidazole (CDI) and then amines of formula $R^4$—NR$^7$—H (preparation I-b) or alcohols of formula $R^4$—O—H (preparation I-c) are added to the reactive intermediate to form urethanes I-b or carbamates I-c (method F, scheme 5).

Scheme 5

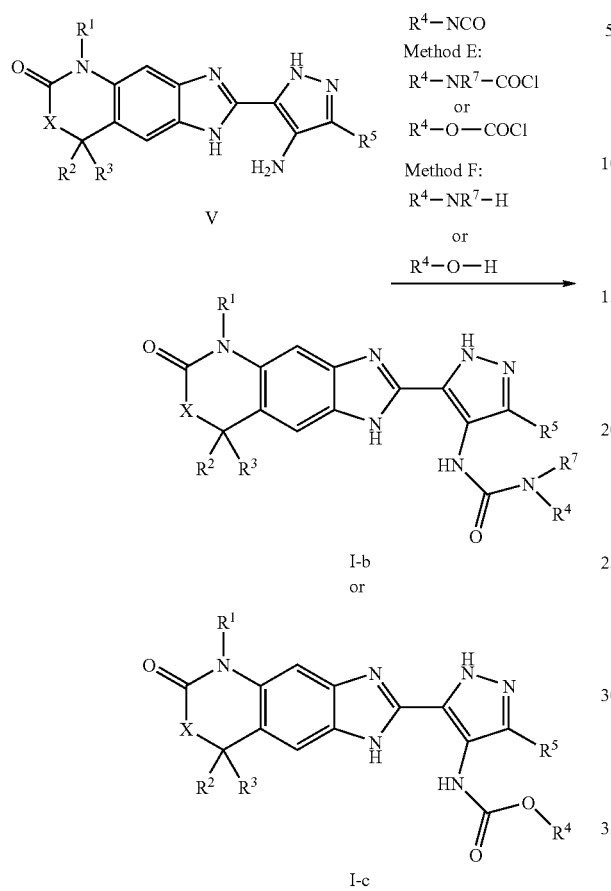

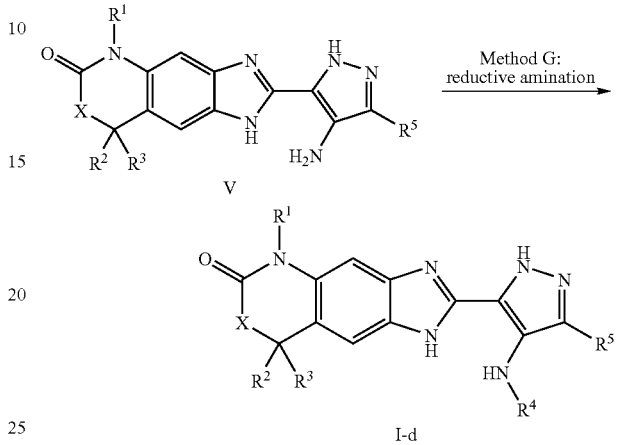

In scheme 5, $R^1$, $R^2$, $R^3$, $R^4$, $R^5$, $R^7$ and X have the significance as given above for formula I. Compounds of formula I in which n is 0 can be prepared using standard reductive amination methods for the synthesis of amines (Scheme 6) and are named I-d. For example, such compounds can be prepared by reaction of an aminopyrazole of formula V with an carbonyl compound and a suitable reducing agent e.g. $NaBH_4$, $NaBH(OAc)_3$, $NaBH_3CN$.

Scheme 6

In scheme 6, $R^1$, $R^2$, $R^3$, $R^4$, $R^5$ and X have the significance as given above for formula I when n is 0.

Compounds of formula I wherein n is 1 and Z is $-SO_2-$ or $-SO_2NR^7-$ can be prepared using standard methods for the synthesis of sulfonamides (Scheme 7). Compounds wherein n is 1 and Z is $-SO_2-$ are named I-e and compounds wherein n is 1 and $-SO_2NR^7-$ are named I-f. For example, such compounds can be prepared by reaction of an aminopyrazole of formula V with an appropriate sulfonyl chloride (method H) or aminosulfonyl chloride (method I) in the presence of a base such as N,N-diisopropylethylamine, pyridine, triethyl amine and the like in an inert solvent like dichloromethane, dimethylformamide (DMF), tetrahydrofuran (THF) and the like.

Scheme 7

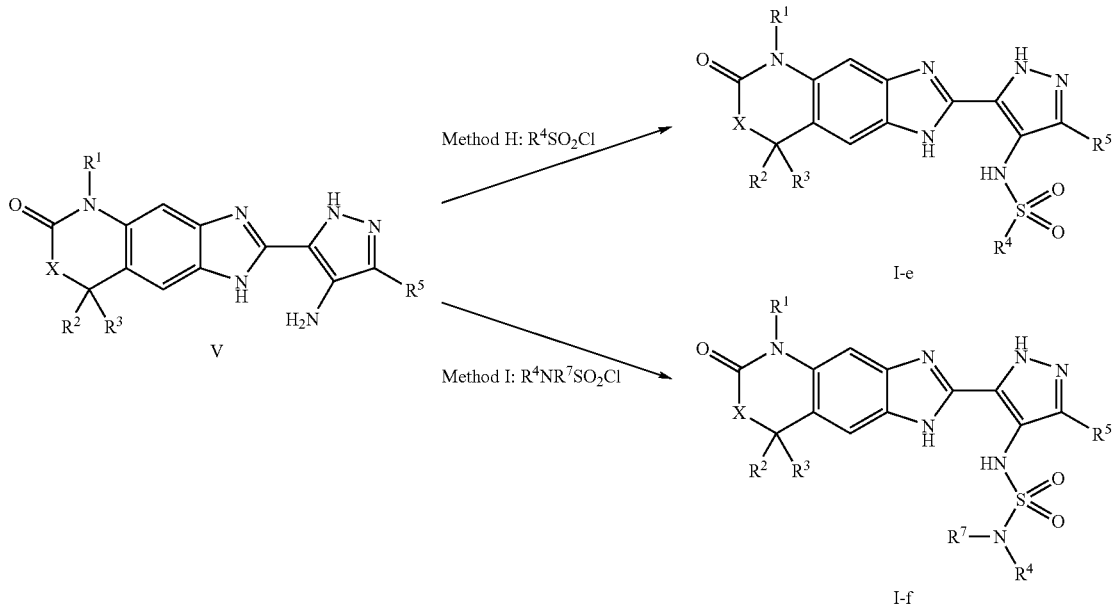

In many of the reactions described above towards compounds of formula I, it may be necessary to protect one or more groups to prevent reaction from taking place at an undesirable location. For example, heterocyclic N—H groups of compounds of formula IV can be reacted with a suitable protecting group (PG) prior to reduction of the nitro group (Scheme 8).

Compounds of formula VI can be prepared using standard methods well known to someone skilled in the art. For example an appropriate protecting group can be trimethylsilylethoxymethyl (SEM) group as described in U.S. Pat. No. 6,534,524B1. Compounds VI (where PG is SEM) can be synthesized using sodium hydride (NaH) as a base, trimethylsilylethoxymethyl chloride (SEM-Cl) in dimethylformamide (DMF) or tetrahydrofuran (THF) as a solvent or with any other detailed procedure relative to protection reported therein.

Detailed procedures relative to reduction towards 4-aminopyrazoles VII and their functionalization listed above and in WO 2005/002552 and WO 03/035065 may be used. Compounds of formula I can be finally obtained after standard methods of deprotection known to those skilled in the art.

a compound of formula I may be synthesized bearing a nitro-, an ethoxycarbonyl, a sulfonic acid substituent on the group $R^1$ and $R^4$, which substituents are finally converted to an amino-, alkylamino-, dialkylamino-, acylamino-, alkylsulfonylamino, arylsulfonylamino substituent, or to a carboxamide substituent, or to a sulfonamide substituent by standard procedures.

Pharmaceutical compositions containing a compound of the present invention or a pharmaceutically acceptable salt or ester thereof and a pharmaceutically acceptable carrier are an object of the present invention, as is a process for their production, which comprises bringing one or more compounds of the present invention and/or pharmaceutically acceptable salts or esters and, if desired, one or more other therapeutic substances into a galenical administration form together with one or more pharmaceutically acceptable carriers.

In accordance with the invention the compounds of the present invention as well as their pharmaceutically acceptable salts or esters are useful in the control or prevention of illnesses. Based on their Aurora tyrosine kinase inhibition and their antiproliferative activity, said compounds are useful for the treatment of diseases such as cancer in humans or animals

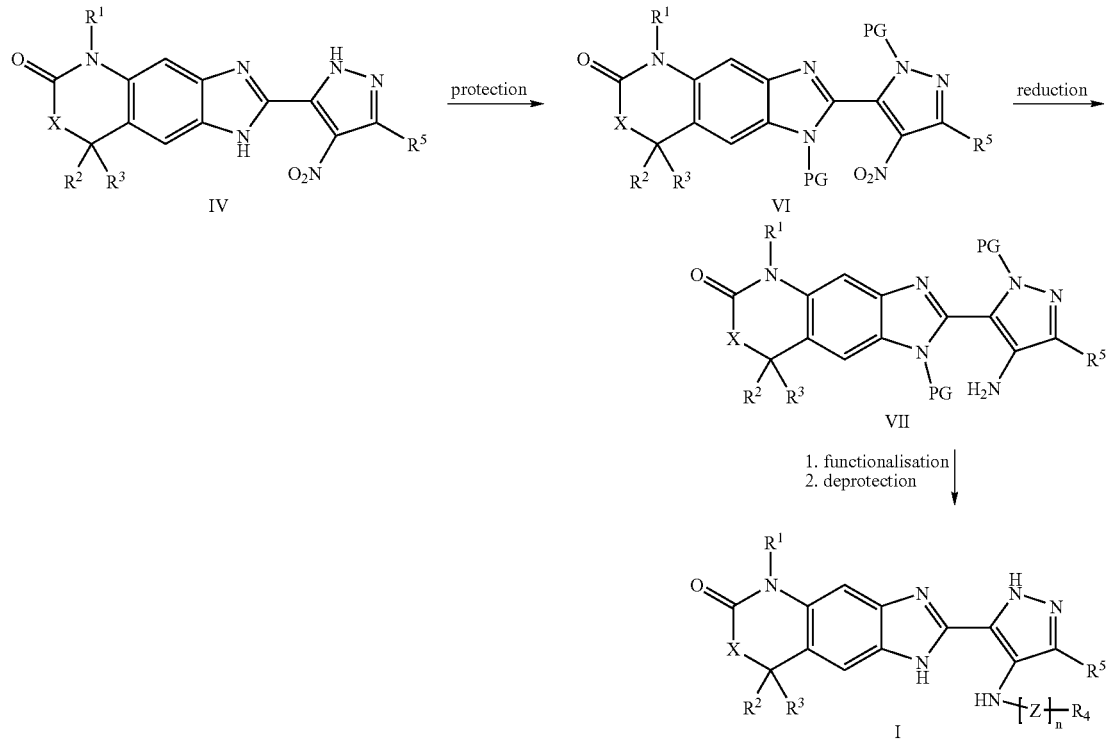

Scheme 8

In scheme 8, $R^1$, $R^2$, $R^3$ and $R^5$ have the significance as given above for formula I and PG means a Protecting Group as described above.

Certain substituents on the groups $R^1$ and $R^4$ may not be inert to the conditions of the synthesis sequences described above and may require protection by standard protecting groups known in the art. For instance, an amino or hydroxyl group may be protected as an acetyl or tert.-butoxycarbonyl derivative. Alternatively, some substituents may be derived from others at the end of the reaction sequence. For instance, and for the production of corresponding pharmaceutical compositions. The dosage depends on various factors such as the manner of administration, species, age and/or individual state of health.

An embodiment of the invention is a pharmaceutical composition, containing one or more compounds according to formula I, together with pharmaceutically acceptable excipients.

Another embodiment of the invention is a pharmaceutical composition containing one or more compounds of formula I as active ingredients together with pharmaceutically acceptable adjuvants for the treatment of diseases mediated by an inappropriate activation of Aurora family tyrosine kinases.

Another embodiment of the invention is a pharmaceutical composition, containing one or more compounds according to formula I, for the inhibition of tumor growth.

Another embodiment of the invention is a pharmaceutical composition containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a pharmaceutical composition containing one or more compounds of formula I as active ingredients together with pharmaceutically acceptable adjuvants for the treatment of acute-myelogenous leukemia (AML), acute lymphocytic leukemia (ALL) and gastrointestinal stromal tumor (GIST).

Another embodiment of the invention is the use of one or more compounds of formula I for the manufacture of pharmaceutical compositions for the treatment of diseases mediated by an inappropriate activation of Aurora family tyrosine kinases.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of pharmaceutical compositions for the treatment of acute-myelogenous leukemia (AML), acute lymphocytic leukemia (ALL) and gastrointestinal stromal tumor (GIST).

Another embodiment of the invention is the use of the compounds of formula I as Aurora A tyrosine kinase inhibitors.

Another embodiment of the invention is the use of the compounds of formula I as anti-proliferating agents.

Another embodiment of the invention is the use of one or more compounds of formula I for the treatment of cancer.

Pharmacological Activity

The compounds of formula I and their pharmaceutically acceptable salts or esters possess valuable pharmacological properties. It has been found that said compounds show activity as inhibitors of the Aurora kinase family and also show anti-proliferative activity. Consequently the compounds of the present invention are useful in the therapy and/or prevention of illnesses with known over-expression of kinases of the Aurora family preferably Aurora A, especially in the therapy and/or prevention of illnesses mentioned above. The activity of the present compounds as inhibitors of the Aurora kinase family is demonstrated by the following biological assay:

$IC_{50}$ Determination for Inhibitors of Aurora A

Assay Principle

Aurora A is a serine threonine kinase involved in spindle assembly and chromosome segregation. The assay is a typically ELISA-type assay where substrate (GST-Histone H3) is coupled to the assay-plate and is phosphorylated by the kinase. Phosphorylation is detected by a mouse anti-Phosphopeptid mAb and an HRP-labeled anti-mouse pAb. The assay is validated for $IC_{50}$-determination.

Kinase activities were measured by Enzyme-Linked Immunosorbent Assay (ELISA): Maxisorp 384-well plates (Nunc) were coated with recombinant fusion protein comprising residues 1-15 of HistoneH3 fused to the N-terminus of Glutathione-S-Transferase. Plates were then blocked with a solution of 1 mg/mL I-block (a highly purified form of casein, Tropix cat. no. T2015) in phosphate-buffered saline. Kinase reactions were carried out in the wells of the ELISA plate by combining an appropriate amount of mutant Aurora A kinase with test compound and 30 µM ATP. The reaction buffer was 10× Kinase Buffer (Cell Signaling cat. no. 9802) supplemented with 1 µg/mL I-block. Reactions were stopped after 40 minutes by addition of 25 mM EDTA. After washing, substrate phosphorylation was detected by addition of anti-phospho-Histone H3 (Ser 10) 6G3 mAb (Cell Signaling cat. no. 9706) and sheep anti-mouse pAb-HRP (Amersham cat# NA931V), followed by colorimetric development with TMB (3,3',5,5'-tetramethylbenzidine from Kirkegaard & Perry Laboratories). After readout of the adsorbance, $IC_{50}$ values were calculated using a non-linear curve fit (XLfit software (ID Business Solution Ltd., Guilford, Surrey, UK)). The results are shown in Table 1.

TABLE 1

Results:

| Example No. | IC50 Aurora A kinase inhibition [µM] |
|---|---|
| A-5 | 0.029 |
| B-2 | 0.010 |
| B-20 | 0.002 |
| C-11 | 0.003 |
| E-5 | 0.019 |
| E-8 | 0.001 |
| F-6 | 0.011 |
| G-2 | 0.032 |
| H-2 | 0.024 |
| B-2, B-5, B-6, B-8, B-9, B-10, B-11, B-13, B-15, B-16, B-22, B-23, B-26, B-30, B-31, C-3, C-5, C-6, C-7, C-10, C-14, C-15, C-16, C-19, C-20, E-2, E-4, E-6, E-7, E-10, E13, E-15, E-16, E-17, E-19, E-22, F-2, F-3, F-4, F-5, F-7, F-9, F-10 | 0.001-0.500 |

Antiproliferative Activity

The activity of the present compounds as antiproliferative agents is demonstrated by the following biological assay:

Viability Assay in HCT 116 Cells

A viability assay was performed using the CellTiter-Glo® Luminescent Cell Viability Assay (see Promega Corporation's Technical Bulletin No. 288, pp. 1-11 [revised 2/04] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HCT 116 cells (human colon carcinoma, ATCC-No. CCl-247) were cultivated in RPMI 1640 medium with GlutaMAX™ I (cell culture media that contains L-Alanyl-L-Glutamine [a stabilized a form/source of L-Glutamine] from Invitrogen, Cat-No. 61870-010), 2.5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the viability assay was done according to the instructions of the manufacturer. In brief: the cell-plate was equilibrated to room temperature for approximately 30 minutes and then reagent (containing luciferase, luciferan substrate, and buffer) was added. The contents were carefully mixed for 15 minutes to induce cell lysis. After 45 minutes the luminescent signal was measured in Victor 2, (scanning multiwell spectrophotometer, Wallac).

Details:

1st. Day:

Medium: RPMI 1640 with cell culture media containing L-Alanyl-L-Glutamine [GlutaMAX™ I (Invitrogen, Cat-No. 61870)], 5% FCS (Sigma Cat.-No. F4135), Pen/Strep (Invitrogen, Cat No. 15140).

HCT116 (ATCC-No. CCl-247): 1000 cells in 60 µl per well of 384 well plate (Greiner 781098, µClear-plate white)

After seeding incubate plates 24 h at 37° C., 5% $CO_2$

2nd. Day: Induction (Treatment with Compounds, 10 Concentrations):

In order to achieve a final concentration of 30 µM as highest concentration 3.5 µl of 10 mM compound stock solution were added directly to 163 µl media. Then step d) of the dilution procedure described below, was followed.

In order to achieve the second highest to the lowest concentrations, a serial dilution with dilution steps of 1:3 was followed according to the procedure (a-d) as described here below:

a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3.5 µl compound dilution to 163 µl media)
d) add 10 µl of every concentration to 60 µl media in the cell plate resulting in final concentration of DMSO: 0.3% in every well and resulting in 10 final concentration of compounds ranging from 30 µMM to 0.0015 µM.

Each compound is tested in triplicate.

Incubate 120 h (5 days) at 37° C., 5% $CO_2$

Analysis:

Add 30 µl of reagent containing luciferase, luciferan substrate, and buffer (lyophilized) per well, shake 15 minutes at room temperature incubate further 45 minutes at room temperature without shaking Measurement:

Victor 2 scanning multiwell spectrophotometer (Wallac), Luminescence mode (0.5 sec/read, 477 nm)

Determine IC50 using a non-linear curve fit (XLfit® software [ID Business Solution Ltd., Guilford, Surrey, UK])

With all compounds a significant inhibition of HCT 116 cell viability was detected, which is exemplified by the compounds shown in Table 2.

TABLE 2

Results:

| Example No. | IC50 HCT 116 [µM] |
|---|---|
| A-1 | 0.311 |
| B-3 | 0.057 |
| B-22 | 0.099 |
| C-13 | 0.063 |
| E-6 | 0.378 |
| E-10 | 0.061 |
| F-4 | 0.028 |
| A-3, B-2, B-5, B-6, B-8, B-9, B-10, B-11, B-13, B-15, B-16, B-21, B-23, B-24, B-26, B-30, B-31, C-3, C-5, C-6, C-7, C-10, C-14, C-15, C-16, C-19, C-20, E-2, E-4, E-7, E-13, E-15, E-16, E-17, E-19, E-21, E-22, F-2, F-3, F-5, F-7, F-9, F-10, G-2 | 0.001-1.500 |

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts or esters and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts or esters for varying the osmotic pressure, buffers, masking agents or antioxidants. They can also contain still other therapeutically valuable substances.

A pharmaceutical composition may comprise, for example, the following:

a) Tablet Formulation (Wet Granulation):

| Item | Ingredients | Mg/tablet | | | |
|---|---|---|---|---|---|
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads:gelatin solution=2:1) and vortex.
4. Cap and wrap in aluminum foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenize.

The following examples and references are provided to aid the understanding of the present invention, the true scope of which is set forth in the appended claims. It is understood that modifications can be made in the procedures set forth without departing from the spirit of the invention.

Experimental Procedures

STARTING MATERIAL EXAMPLES 1-1 to 1

Example 1-1

Preparation of 5,6-diamino-1-ethyl-3,3-dimethyl-1,3-dihydro-indol-2-one i) 1-Ethyl-3,3-dimethyl-6-nitro-1,3-dihydro-indol-2-one A solution of 3,3-dimethyl-6-nitro-1,3-dihydro-indol-2-one (6 g, 29.10 mmol) in anhydrous N,N-dimethylformamide (DMF) (35 ml) was treated with sodium hydride. The resulting suspension was stirred for 1 h at 60° C. A solution of bromo-ethane (2.17 mL, 3.17 g, 29.10 mmol) in DMF (10 ml) was added. The mixture was allowed to cool to room temperature and stirred for 1 h. After removal of the solvent the mixture was quenched with water (100 ml) and extracted with ethyl acetate (3×100 ml). The extract was dried over $Na_2SO_4$, evaporated and the crude product was purified by column chromatography on silica gel. Elution with ethyl acetate/n-heptane (1:3) yielded 5.94 g (87%) of a yellow solid.
MS: M=235.3 (ESI+)
$^1$H-NMR (400 MHz, DMSO): δ (ppm)=1.16 (t, 3H), 1.32 (s, 6H), 3.81 (q, 2H), 7.66 (d, 1H), 7.86 (s, 1H), 7.97 (d, 1H)

ii) 6-Amino-1-ethyl-3,3-dimethyl-1,3-dihydro-indol-2-one

To a solution of 1-ethyl-3,3-dimethyl-6-nitro-1,3-dihydro-indol-2-one (5.9 g, 25.19 mmol) in methanol/tetrahydrofuran (THF) palladium on charcoal (10%) was added and the mixture hydrogenated at room temperature. After filtration and evaporation of the solvents 5.05 g (98%) 6-amino-1-ethyl-3,3-dimethyl-1,3-dihydro-indol-2-one was isolated as white solid.
MS: M=205.0 (API+)
$^1$H-NMR (400 MHz, DMSO): δ (ppm)=1.11 (t, 3H), 1.17 (s, 6H), 3.58 (q, 2H), 5.12 (br, 2H), 6.21 (d, 1H), 6.25 (s, 1H), 6.92 (d, 1H)

iii) N-(1-Ethyl-3,3-dimethyl-2-oxo-2,3-dihydro-1H-indol-6-yl)-acetamide

A solution of 6-amino-1-ethyl-3,3-dimethyl-1,3-dihydro-indol-2-one (5.05 g, 24.72 mmol) in acetic anhydride (80 ml) was stirred at room temperature for 4 h. The mixture was poured onto ice water (150 ml), allowed to warm to room temperature and was stirred again for 2 h. After extraction with ethyl acetate (3×100 ml), the combined organic layers were washed with sat. $NaHCO_3$-solution (3×100 ml), brine (100 ml) and dried over sodium sulfate. After removal of the solvent the crude product was purified by column chromatography on silica gel (ethyl acetate/n-heptane 1:1) yielding 5.6 g (91%) N-(1-ethyl-3,3-dimethyl-2-oxo-2,3-dihydro-1H-indol-6-yl)-acetamide as light yellow solid.
MS: M=247.1 (API+)
$^1$H-NMR (400 MHz, DMSO): δ (ppm)=1.13 (t, 3H), 1.23 (s, 6H), 2.04 (s, 3H), 3.63 (q, 2H), 7.12 (d, 1H), 7.23 (d, 1H), 7.37 (s, 1H), 9.97 (br, 1H)

iv) N-(1-ethyl-3,3-dimethyl-5-nitro-2-oxo-2,3-dihydro-1H-indol-6-yl)-acetamide

To a solution of N-(1-ethyl-3,3-dimethyl-2-oxo-2,3-dihydro-1H-indol-6-yl)-acetamide (5.6 g, 22.73 mmol) in acetic anhydride (70 ml) nitric acid (100%, 1.96 g, 1.29 ml, 31.2 mmol) was added at 0° C. The mixture was stirred for 30 min, then poured onto ice water (150 ml). After stirring for 4 h the mixture was extracted with ethyl acetate (3×100 ml). The combined organic layers were washed with sodium hydroxide solution (1M, 100 ml) and water (100 ml), dried over sodium sulfate and concentrated. The crude product was purified by column chromatography on silica gel (ethyl acetate/n-heptane 1:1) to yield 5.2 g (78%) N-(1-ethyl-3,3-dimethyl-5-nitro-2-oxo-2,3-dihydro-1H-indol-6-yl)-acetamide as a yellow solid.

MS: M=292.0 (API+)
$^1$H-NMR (400 MHz, DMSO): δ (ppm)=1.16 (t, 3H), 1.31 (s, 6H), 2.13 (s, 3H), 3.71 (m, 2H), 7.54 (s, 1H), 8.12 (s, 1H), 10.39 (br, 1H)

v) 6-Amino-1-ethyl-3,3-dimethyl-5-nitro-1,3-dihydro-indol-2-one

N-(1-ethyl-3,3-dimethyl-5-nitro-2-oxo-2,3-dihydro-1H-indol-6-yl)-acetamide (5.2 g, 17.85 mmol) was dissolved in ethanol (40 ml). After addition of hydrochloric acid (25%, 8 ml, 81.44 mmol) the mixture was stirred under reflux for 3 h. The reaction mixture was allowed to cool down to room temperature and then quenched with water (80 ml). The yellow precipitate was isolated by suction and washed with ethanol/water (1:1). The solid was dissolved in ethyl acetate, dried over sodium sulfate and concentrated to yield 4.15 g (93%) 6-amino-1-ethyl-3,3-dimethyl-5-nitro-1,3-dihydro-indol-2-one as a orange solid.

MS: M=250.0 (API+)
$^1$H-NMR (400 MHz, DMSO): δ (ppm)=1.15 (t, 3H), 1.27 (s, 6H), 3.64 (m, 2H), 6.54 (s, 1H), 7.67 (br, 2H), 7.95 (s, 1H)

vi) 5,6-Diamino-1-ethyl-3,3-dimethyl-1,3-dihydro-indol-2-one

To a solution of 6-amino-1-ethyl-3,3-dimethyl-5-nitro-1,3-dihydro-indol-2-one (4.15 g, 16.65 mmol) in ethanol (80 ml) PtO$_2$ (0.4 g) was added and the mixture hydrogenated at room temperature for 3.5 h. After filtration and evaporation of the solvents 3.25 g (89%) 5,6-diamino-1-ethyl-3,3-dimethyl-1,3-dihydro-indol-2-one was isolated as orange solid.

MS: M=220.0 (API+)
$^1$H-NMR (400 MHz, DMSO): δ (ppm)=1.10 (t, 3H), 1.13 (s, 6H), 3.53 (m, 2H), 4.08 (br, 2H), 4.48 (br, 2H), 6.27 (s, 1H), 6.50 (s, 1H)

Example 1-2

Preparation of 5,6-Diamino-1-isopropyl-3,3-dimethyl-1,3-dihydro-indol-2-one 5,6-Diamino-1-isopropyl-3,3-dimethyl-1,3-dihydro-indol-2-one was prepared in an analogous 6-step-synthesis as described for 5,6-diamino-1-ethyl-3,3-dimethyl-1,3-dihydro-indol-2-one in Example 1-1.
MS: M=234.1 (ESI+)

Example 1-3

Preparation of 5,6-Diamino-3,3-diethyl-1-isopropyl-1,3-dihydro-indol-2-one i) 3,3-Diethyl-5-nitro-1,3-dihydro-indol-2-one To a solution of 3,3-diethyl-1,3-dihydro-indol-2-one (10.0 g, 52.84 mmol, A. Mertens et al., J. Med. Chem. 1987, 30, 1279-1287) in conc. sulfuric acid (50 ml) was added slowly a mixture of nitric acid (65%, 5.12 g, 3.63 ml, 52.84 mmol) and conc. sulfuric acid (10 ml) at 0° C. After 2 h at room temperature the mixture was poured into ice water. The precipitate was filtered off, washed with water and dried to yield 11.7 g 3,3-diethyl-5-nitro-1,3-dihydro-indol-2-one (49.95 mmol, 94%).
MS: M=235.1 (ESI+)

ii) 3,3-Diethyl-1-isopropyl-5-nitro-1,3-dihydro-indol-2-one

A solution of 3,3-diethyl-5-nitro-1,3-dihydro-indol-2-one (11.7 g, 49.95 mmol) in anhydrous N,N-dimethylformamide (DMF) (60 ml) was treated with sodium hydride (1.558 g, 64.93 mmol). The resulting suspension was stirred for 1 h at 60° C. A solution of 2-iodo-propane (4.99 ml, 8.49 g, 49.95 mmol) was added. The mixture was kept at 60° C. for further 3 h, allowed to cool to room temperature poured into ice water. The precipitate was filtered off, washed with water and dried to yield 12.6 g 3,3-diethyl-1-isopropyl-5-nitro-1,3-dihydro-indol-2-one (45.60 mmol, 91%)
MS: M=277.1 (ESI+)

iii) 5-Amino-3,3-diethyl-1-isopropyl-1,3-dihydro-indol-2-one

To a solution of 3,3-diethyl-1-isopropyl-5-nitro-1,3-dihydro-indol-2-one (12.6 g, 45.60 mmol) in methanol/tetrahydrofuran (THF) (1:1, 80 ml) palladium on charcoal (10%, 1.2 g) was added and the mixture hydrogenated at room temperature for 4 h. After filtration of the catalyst the solvent was evaporated and the residue triturated with iso-hexane to yield 9.7 g 5-amino-3,3-diethyl-1-isopropyl-1,3-dihydro-indol-2-one (39.37 mmol, 86%).
MS: M=247.1 (ESI+)

iv) N-(3,3-Diethyl-1-isopropyl-2-oxo-2,3-dihydro-1H-indol-5-yl)-acetamide

A solution of 5-amino-3,3-diethyl-1-isopropyl-1,3-dihydro-indol-2-one (9.7 g, 39.37 mmol) in acetic anhydride (57 ml) was stirred at room temperature for 4 h. The mixture was poured into ice water, allowed to warm to room temperature and was stirred again for 2 h. After extraction with ethyl acetate, the combined organic layers were washed with aqueous NaOH solution (1M) and brine and dried over sodium sulfate. After removal of the solvent the crude product was triturated with iso-hexane to yield 10.4 g N-(3,3-Diethyl-1-isopropyl-2-oxo-2,3-dihydro-1H-indol-5-yl)-acetamide (36.06 mmol, 91%)
MS: M=289.2 (ESI+)

v) N-(3,3-Diethyl-1-isopropyl-6-nitro-2-oxo-2,3-dihydro-1H-indol-5-yl)-acetamide To a solution of N-(3,3-diethyl-1-isopropyl-2-oxo-2,3-dihydro-1H-indol-5-yl)-acetamide (10.4 g, 36.06 mmol) in conc. sulfuric acid (50 ml) was added slowly a mixture of nitric acid (65%, 3.84 g, 2.72 ml, 39.67 mmol) and conc. sulfuric acid (10 ml) at 0° C. After 2 h at room temperature the mixture was poured into ice water. The precipitate was filtered off, washed with water and dried. The crude material was purified by silica gel chromatography (isohexane/ethyl acetate 1:1) to yield 2.2 g N-(3,3-diethyl-1-isopropyl-6-nitro-2-oxo-2,3-dihydro-1H-indol-5-yl)-acetamide (6.60 mmol, 18%) besides undesired N-(3,3-diethyl-1-isopropyl-7-nitro-2-oxo-2,3-dihydro-1H-indol-5-yl)-acetamide (5.5 g).
MS: M=332.2 (ESI–)

vi) 5-Amino-3,3-diethyl-1-isopropyl-6-nitro-1,3-dihydro-indol-2-one

N-(3,3-diethyl-1-isopropyl-6-nitro-2-oxo-2,3-dihydro-1H-indol-5-yl)-acetamide (2.2 g, 6.60 mmol) was dissolved in ethanol (50 ml). After addition of hydrochloric acid (25%, 3.2 ml, 33.0 mmol) the mixture was heated under reflux for 3 h. Most of the solvent was evaporated and water was added. The mixture was weakly alkalized by addition of aqueous NaOH solution. The mixture was extracted with ethyl acetate, the combined organic phases were dried over magnesium sulfate and the solvent was evaporated to yield 1.9 g 5-amino-3,3-diethyl-1-isopropyl-6-nitro-1,3-dihydro-indol-2-one (6.52 mmol, 99%).
MS: M=290.1 (ESI–)

vii) 5,6-Diamino-3,3-diethyl-1-isopropyl-1,3-dihydro-indol-2-one

To a solution of 5-amino-3,3-diethyl-1-isopropyl-6-nitro-1,3-dihydro-indol-2-one (1.9 g, 6.52 mmol) in methanol/tetrahydrofuran (THF) (1:1, 80 ml) palladium on charcoal (10%, 1.2 g) was added and the mixture hydrogenated at room temperature for 4 h. After filtration the solvent was evaporated and the residue triturated with iso-hexane to yield 1.7 g 5,6-diamino-3,3-diethyl-1-isopropyl-1,3-dihydro-indol-2-one (6.50 mmol, 99%).
MS: M=262.3 (ESI+)
$^1$H-NMR (400 MHz, DMSO): δ (ppm)=0.44 (t, 6H), 1.34 (d, 6H), 1.55 (q, 2H), 1.65 (q, 2H), 4.40 (br, 4H), 4.45 (m, 1H), 6.42 (s, 1H), 6.46 (s, 1H)

Example 1-4

Preparation of 5,6-Diamino-1,3,3-triethyl-1,3-dihydro-indol-2-one 5,6-Diamino-1,3,3-triethyl-1,3-dihydro-indol-2-one was prepared in an analogous 7-step-synthesis as described for 5,6-diamino-3,3-diethyl-1-isopropyl-1,3-dihydro-indol-2-one in Example 1-3.
MS: M=248.1 (API+)
$^1$H-NMR (400 MHz, DMSO): δ (ppm)=0.43 (t, 6H), 1.08 (t, 3H), 1.55 (q, 2H), 1.63 (q, 2H), 3.54 (q, 2H), 4.10 (br, 2H), 4.48 (br, 2H), 6.27 (s, 1H), 6.43 (s, 1H)

Example 1-5

Preparation of 2-(4-Amino-1H-pyrazol-3-yl)-5-ethyl-7,7-dimethyl-5,7-dihydro-1H-imidazo[4,5-f]indol-6-one i) 5-Ethyl-7,7-dimethyl-2-(4-nitro-1H-pyrazol-3-yl)-5,7-dihydro-1H-imidazo[4,5-f]indol-6-one 5,6-Diamino-1-ethyl-3,3-dimethyl-1,3-dihydro-indol-2-one (5.00 g, 22.80 mmol), and 4-nitro-pyrazole carboxylic acid (3.58 g, 22.80 mmol) were mixed with polyphosphoric acid (22.34 g, 228.0 mmol) and phosphorus pentoxide (1.63 g, 11.4 mmol) and stirred under nitrogen at 150° C. for 6 h. It was quenched with ice water (250 ml) and the resulting suspension was adjusted to pH 5 by adding aqueous ammonia. The crude microcrystalline solid was dissolved in ethyl acetate (400 mL). The organic layer was separated and the aqueous layer was further extracted with ethyl acetate (4×400 mL). After evaporation of the solvent, the crude product was purified by HPLC (High Performance Liquid Chromatography). 5-Ethyl-7,7-dimethyl-2-(4-nitro-1H-pyrazol-3-yl)-5,7-dihydro-1H-imidazo[4,5-f]indol-6-one was obtained as an orange solid (2.47 g, 32%).
MS: M=340.9 (API+)
$^1$H-NMR (400 MHz, DMSO): δ (ppm)=1.20 (t, 3H), 1.33 (s, 6H), 3.73 (q, 2H), 7.22 (s, 1H), 7.67 (s, 1H), 8.77 (s, 1H), 12.80 (br, 1H), 14.40 (br, 1H)

ii) 2-(4-Amino-1H-pyrazol-3-yl)-5-ethyl-7,7-dimethyl-5,7-dihydro-1H-imidazo[4,5-f]indol-6-one To a solution of 5-ethyl-7,7-dimethyl-2-(4-nitro-1H-pyrazol-3-yl)-5,7-dihydro-1H-imidazo[4,5-f]indol-6-one was obtained as an orange solid (755 mg, 2.21 mmol) in tetrahydrofuran (THF) (25 ml) palladium on charcoal (10%, 300 mg) was added and the mixture hydrogenated at room temperature for 4 h. After filtration and removal of the solvent, the product was used without any purification. 650 mg of 2-(4-Amino-1H-pyrazol-3-yl)-5-ethyl-7,7-dimethyl-5,7-dihydro-1H-imidazo[4,5-f]indol-6-one was isolated as purple powder (94%).
MS: M=311.1 (API+)
$^1$H-NMR (400 MHz, DMSO): δ (ppm)=1.17 (t, 3H), 1.31 (s, 6H), 3.76 (q, 2H), 7.11 (s, 1H), 7.29 (s, 1H), 7.50 (s, 1H), 12.60 (br, 1H)

Example 1-6

Preparation of 2-(4-Amino-1H-pyrazol-3-yl)-7,7-dimethyl-5,7-dihydro-1H-imidazo[4,5-f]indol-6-one 2-(4-amino-1H-pyrazol-3-yl)-7,7-dimethyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.
MS: M=281.1 (API–)
$^1$H-NMR (400 MHz, DMSO): δ (ppm)=1.31 (s, 6H), 4.88 (br, 2H), 6.93 and 7.03 (br, 1H, tautomeric forms), 7.23 (s, 1H), 7.32 and 7.53 (br, 1H, tautomeric forms), 10.27 (s, 1H), 12.39 (br, 1H), 12.59 (s, 1H)

Example 1-7

Preparation of 2-(4-Amino-5-methyl-1H-pyrazol-3-yl)-7,7-dimethyl-5,7-dihydro-1H-imidazo[4,5-f]indol-6-one 2-(4-Amino-5-methyl-1H-pyrazol-3-yl)-7,7-dimethyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.
MS: M=295.1 (API–)
$^1$H-NMR (400 MHz, DMSO): δ (ppm)=1.29 (s, 6H), 2.15 (s, 3H), 4.60 (br, 2H), 6.90 (s, 1H), 7.40 (br, 1H), 10.22 (s, 1H), 12.35 (s, 1H)

Example 1-8

Preparation of 2-(4-Amino-5-methyl-1H-pyrazol-3-yl)-5-ethyl-7,7-dimethyl-5,7-dihydro-1H-imidazo[4,5-f]indol-6-one 2-(4-Amino-5-methyl-1H-pyrazol-3-yl)-5-ethyl-7,7-dimethyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.

MS: M=325.1 (API+)

$^1$H-NMR (400 MHz, DMSO): δ (ppm)=1.18 (t, 3H), 1.30 (s, 6H), 2.16 (s, 3H), 3.75 (m, 2H), 4.65 (br, 2H), 6.95 and 7.25 (s, 1H, two tautomeric forms), 7.32 and 7.59 (s, 1H, two tautomeric forms), 12.35 and 12.39 (br, 1H, two tautomeric forms), 12.45 and 12.50 (br, 1H, two tautomeric forms)

Example 1-9

Preparation of 2-(4-Amino-1H-pyrazol-3-yl)-5-isopropyl-7,7-dimethyl-5,7-dihydro-1H-imidazo[4,5-f]indol-6-one 2-(4-Amino-1H-pyrazol-3-yl)-5-isopropyl-7,7-dimethyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.

MS: M=325.3 (ESI+)

$^1$H-NMR (400 MHz, DMSO): δ (ppm)=1.29 (s, 6H), 1.44 (d, 6H), 4.02 (m, 1H), 4.89 (br, 1H), 7.08 and 7.20 (d, 1H, tautomeric forms), 7.32 and 7.58 (d, 1H, tautomeric forms), 12.55 (br, 2H)

Example 1-10

Preparation of 2-(4-Amino-1H-pyrazol-3-yl)-5,7,7-triethyl-5,7-dihydro-1H-imidazo[4,5-f]indol-6-one 2-(4-Amino-1H-pyrazol-3-yl)-5,7,7-triethyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.

MS: M=339.3 (ESI+)

Example 1-11

Preparation of 2-(4-Amino-1H-pyrazol-3-yl)-7,7-diethyl-5-isopropyl-5,7-dihydro-1H-imidazo[4,5-f]indol-6-one 2-(4-Amino-1H-pyrazol-3-yl)-7,7-diethyl-5-isopropyl-5,7-dihydro-1H-imidazo[4,5-f]indol-6-one was prepared in an analogous 2-step-synthesis as described for 2-(4-amino-1H-pyrazol-3-yl)-5-ethyl-7,7-dimethyl-5,7-dihydro-1H-imidazo[4,5-f]indol-6-one in Example 1-5.

MS: M=353.4 (ESI+)

Final products

Examples A

General Procedure A

To a solution of appropriate aminopyrazole (0.97 mmol) in pyridine/dichloromethane (1:1, 6.0 ml), an appropriate acid anhydride or acyl halide (10.58 mmol) was added at room temperature. The mixture was stirred for 15 hours. The solvent was removed under diminished pressure. After evaporation, the mixture was stirred in acetonitrile/methanol (1:2, 15.0 ml) with aqueous ammonia (4.2 ml) for 3 hours. Water (50 ml) was added and the mixture was extracted three times with ethyl acetate (3×50 ml). The combined organic layers were washed with aqueous hydrochloric acid (1N), brine, dried and evaporated to afford a residue purified by HPLC.

The following compounds were made using general procedure A:

Example A-1

N-[3-(5-Ethyl-7,7-dimethyl-6-oxo-1,5,6,7-tetrahydro-imidazo[4,5-f]indol-2-yl)-1H-pyrazol-4-yl]-acetamide N-[3-(5-Ethyl-7,7-dimethyl-6-oxo-1,5,6,7-tetrahydro-imidazo[4,5-f]indol-2-yl)-1H-pyrazol-4-yl]-acetamide was prepared using 2-(4-amino-1H-pyrazol-3-yl)-5-ethyl-7,7-dimethyl-5,7-dihydro-1H-imidazo[4,5-f]indol-6-one (300 mg, 0.97 mmol) and acetic anhydride. The title compound was obtained as light brown powder (93 mg).

MS: M=353.1 (API+)

$^1$H-NMR (400 MHz, $D_6$-DMSO): δ (ppm)=1.19 (t, 3H), 1.32 (s, 6H), 2.20 (s, 3H), 3.78 (m, 2H), 7.05 and 7.35 (s, 1H, tautomeric forms), 7.45 and 7.75 (s, 1H, tautomeric forms), 8.22 (s, 1H), 10.26 (s, 1H), 13.00 (br, 1H), 13.15 (br, 1H)

Example A-2

N-[3-(7,7-Dimethyl-6-oxo-1,5,6,7-tetrahydro-imidazo[4,5-f]indol-2-yl)-1H-pyrazol-4-yl]-acetamide N-[3-(7,7-Dimethyl-6-oxo-1,5,6,7-tetrahydro-imidazo[4,5-f]indol-2-yl)-1H-pyrazol-4-yl]-acetamide was prepared using 2-(4-amino-1H-pyrazol-3-yl)-7,7-dimethyl-5,7-dihydro-1H-imidazo[4,5-f]indol-6-one (150 mg, 0.53 mmol) and acetic anhydride. The title compound was obtained as white powder (73 mg).

MS: M=325.1 (API+)

$^1$H-NMR (400 MHz, $D_6$-DMSO): δ (ppm)=1.31 (s, 6H), 2.20 (s, 3H), 6.96 (s, 1H), 7.60 (s, 1H), 8.22 (s, 1H), 10.25 (s, 1H), 10.32 (br, 1H), 12.95 (br, 2H)

Example A-3

N-[3-(5-Ethyl-7,7-dimethyl-6-oxo-1,5,6,7-tetrahydro-imidazo[4,5-f]indol-2-yl)-1H-pyrazol-4-yl]-benzamide N-[3-(5-Ethyl-7,7-dimethyl-6-oxo-1,5,6,7-tetrahydro-imidazo[4,5-f]indol-2-yl)-1H-pyrazol-4-yl]-benzamide was prepared using 2-(4-amino-1H-pyrazol-3-yl)-5-ethyl-7,7-dimethyl-5,7-dihydro-1H-imidazo[4,5-f]indol-6-one (100 mg, 0.32 mmol) and benzoic anhydride. The title compound was obtained as white powder (53 mg).

MS: M=415.1 (API+)

¹H-NMR (400 MHz, D₆-DMSO): δ (ppm)=1.20 (t, 3H), 1.34 (s, 6H), 3.78 (br, 2H), 7.04 and 7.36 (s, 1H, tautomeric forms), 7.46 and 7.77 (s, 1H, tautomeric forms), 7.70 (m, 3H), 8.07 (m, 2H), 8.40 (s, 1H), 11.47 (s, 1H), 13.23 (br, 2H)

Example A-4

N-[3-(7,7-Dimethyl-6-oxo-1,5,6,7-tetrahydro-imidazo[4,5-f]indol-2-yl)-5-methyl-1H-pyrazol-4-yl]-acetamide N-[3-(7,7-Dimethyl-6-oxo-1,5,6,7-tetrahydro-imidazo[4,5-f]indol-2-yl)-5-methyl-1H-pyrazol-4-yl]-acetamide was prepared using 2-(4-amino-5-methyl-1H-pyrazol-3-yl)-7,7-dimethyl-5,7-dihydro-1H-imidazo[4,5-f]indol-6-one (60 mg, 0.21 mmol) and acetyl chloride. The title compound was obtained as white powder (3.7 mg).

MS: M=339.1 (API+)

¹H-NMR (400 MHz, CD₃CN): δ (ppm)=1.39 (s, 6H), 2.18 (s, 3H), 2.34 (s, 3H), 7.08 (s, 1H), 7.50 (s, 1H), 8.42 (s, 1H), 8.86 (br, 1H)

Example A-5

N-[3-(5-Ethyl-7,7-dimethyl-6-oxo-1,5,6,7-tetrahydro-imidazo[4,5-f]indol-2-yl)-1H-pyrazol-4-yl]-2,2,2-trifluoro-acetamide N-[3-(5-Ethyl-7,7-dimethyl-6-oxo-1,5,6,7-tetrahydro-imidazo[4,5-f]indol-2-yl)-1H-pyrazol-4-yl]-2,2,2-trifluoro-acetamide was prepared using 2-(4-amino-1H-pyrazol-3-yl)-5-ethyl-7,7-dimethyl-5,7-dihydro-1H-imidazo[4,5-f]indol-6-one (250 mg, 0.80 mmol) and trifluoroacetic anhydride (125 ml, 0.88 mmol). The title compound was obtained as brown powder (59 mg, 18%).

MS: M=407.3 (ESI+)

¹H-NMR (400 MHz, D₆-DMSO): δ (ppm)=1.21 (m, 3H), 1.32 (s, 6H), 3.78 (m, 2H), 7.05 and 7.25 (s, 1H, tautomeric forms), 7.50 and 7.65 (s, 1H, tautomeric forms), 8.36 (s, 1H), 11.95 (br, 1H), 13.25 (br, 1H), 13.52 (br, 1H)

Examples B

Example B-1

N-[3-(5-Ethyl-7,7-dimethyl-6-oxo-1,5,6,7-tetrahydro-imidazo[4,5-f]indol-2-yl)-1H-pyrazol-4-yl]-propionamide To a solution of 2-(4-amino-1H-pyrazol-3-yl)-5-ethyl-7,7-dimethyl-5,7-dihydro-1H-imidazo[4,5-f]indol-6-one (150 mg, 0.48 mmol), triethylamine (0.20 ml, 14.50 mmol) in dichloromethane (8.0 ml), propionyl chloride (134 mg, 1.45 mmol) was added at room temperature. The mixture was stirred for 15 hours. The solvent was removed under diminished pressure. After evaporation, the mixture was stirred in acetonitrile/methanol (1:2, 9.0 ml) with aqueous ammonia (3.0 ml) for 3 hours. Water (50 ml) was added and the mixture was extracted three times with ethyl acetate (3×50 ml). The combined organic layers were washed with aqueous hydrochloric acid (1N), brine, dried and evaporated to afford a residue purified by HPLC. The title compound was obtained as white powder (19 mg).

MS: M=367.2 (API+)

¹H-NMR (400 MHz, D₆-DMSO): δ (ppm)=1.18-1.22 (m, 6H), 1.31 (s, 6H), 2.47 (m, 2H), 3.77 (q, J=6.99 Hz, 2H), 7.01, 7.31, 7.43, 7.67 (br, 2H, tautomeric forms), 8.24 (s, 1H), 10.34 (s, 1H), 13.06 (br, 2H)

Compounds B-2 to B-4 were prepared following the same method:

Example B-2

Cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide Cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and cyclopropanecarbonyl chloride (152 mg, 1.45 mmol). The title compound was obtained as white powder (23 mg).

MS: M=379.1 (API+)

¹H-NMR (400 MHz D₆-DMSO): δ (ppm)=0.88-0.90 (m, 4H), 1.20 (t, J=7.07 Hz, 3H), 1.32 (s, 6H), 1.84-1.90 (m, 1H), 3.77 (q, J=7.16 Hz, 2H), 7.02, 7.34, 7.44, 7.70 (br, 2H, tautomeric forms), 8.19 (s, 1H), 10.58 (s, 1H), 13.07 (br, 2H)

Example B-3

N-[3-(5-Ethyl-7,7-dimethyl-6-oxo-1,5,6,7-tetrahydro-imidazo[4,5-f]indol-2-yl)-1H-pyrazol-4-yl]-nicotinamide N-[3-(5-Ethyl-7,7-dimethyl-6-oxo-1,5,6,7-tetrahydro-imidazo[4,5-f]indol-2-yl)-1H-pyrazol-4-yl]-nicotinamide was prepared using 2-(4-amino-1H-pyrazol-3-yl)-5-ethyl-7,7-dimethyl-5,7-dihydro-1H-imidazo[4,5-f]indol-6-one (200 mg, 0.64 mmol) and nicotinoyl chloride hydrochloride (282 mg, 1.93 mmol). The title compound was obtained as pink powder (94 mg, 35%).

MS: M=416.2 (API+)

¹H-NMR (400 MHz, D₆-DMSO): δ (ppm)=1.21 (t, 3H), 1.34 (s, 6H), 3.79 (m, 2H), 7.04 and 7.33 (s, 1H, tautomeric forms), 7.46 and 7.72 (s, 1H, tautomeric forms), 7.75 (m, 1H), 8.40 (m, 2H), 8.85 (s, 1H), 9.23 (s, 1H), 9.50 (s, 1H), 13.2 (br, 1H)

Example B-4

Cyclohexanecarboxylic acid[3-(5-ethyl-7,7-dimethyl-6-oxo-1,5,6,7-tetrahydro-imidazo[4,5-f]indol-2-yl)-1H-pyrazol-4-yl]-amide Cyclohexanecarboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (200 mg, 0.64 mmol) and cyclohexanecarbonyl chloride (258 μl, 1.93 mmol). The title compound was obtained as light brown powder (64 mg, 23%).

MS: M=421.2 (API+)

¹H-NMR (400 MHz, D₆-DMSO): δ (ppm)=1.20 (m, 3H), 1.30 (s, 6H), 1.49 (m, 2H), 1.69 (d, 1H) 1.81 (d, 2H), 1.97 (m, 2H), 3.78 (m, 2H), 7.01 and 7.31 (s, 1H, tautomeric forms), 7.45 and 7.68 (s, 1H, tautomeric forms), 8.25 (s, 1H), 10.37 (s, 1H), 13.05 (br, 1H), 13.18 (br, 1H)

Example B-5

N-[3-(5-Ethyl-7,7-dimethyl-6-oxo-1,5,6,7-tetrahydro-imidazo[4,5-f]indol-2-yl)-1H-pyrazol-4-yl]-4-fluoro-benzamide To a solution of 2-(4-amino-1H-pyrazol-3-yl)-5-ethyl-7,7-dimethyl-5,7-dihydro-1H-imidazo[4,5-f]indol-6-one (250 mg, 0.81 mmol), diisopropylethylamine (0.36 ml, 2.01 mmol) in THF (0.8 ml), 4-fluorobenzoyl chloride (114 μL, 0.97 mmol) was slowly added at rt. The mixture was stirred overnight at rt. Aqueous NaOH (2 mL, 1M) was added and the solvent was evaporated. Water (25 ml) was added and the mixture was extracted three times with ethyl acetate (3×25 ml). The combined organic layers were washed with brine, dried and evaporated to afford a residue which precipitated after addition of methanol. The precipitate was suspended in MeOH/CH$_3$CN (1:1, 6 mL) and refluxed for 2 hours in aqueous KOH (0.50 mL, 5M). After evaporation of the solvent and addition of water, a white solid was isolated and dried under high vacuum. The title compound was obtained (77 mg).

MS: M=433.4 (ESI+)

$^1$H-NMR (400 MHz, D$_6$-DMSO): δ (ppm)=1.21 (m, 3H), 1.35 (s, 6H), 3.80 (m, 2H), 7.08 (br, 1H), 7.54 (m, 2H), 7.79 (br, 1H), 8.13 (m, 2H), 8.38 (s, 1H), 11.52 (s, 1H), 13.24 (br, 1H)

Example B-6

Cyclopentanecarboxylic acid[3-(5-ethyl-7,7-dimethyl-6-oxo-1,5,6,7-tetrahydro-imidazo[4,5f]indol-2-yl)-1H-pyrazol-4-yl]-amide To a solution of 2-(4-amino-1H-pyrazol-3-yl)-5-ethyl-7,7-dimethyl-5,7-dihydro-1H-imidazo[4,5-f]indol-6-one (200 mg, 0.64 mmol), diisopropylethylamine (0.28 ml, 1.61 mmol) in THF (0.5 ml), cyclopentanoyl chloride (86.1 μL, 0.71 mmol) was slowly added at rt. The mixture was stirred for 2 hours at rt. Aqueous NaOH (2 mL, 1M) was added and the solvent was evaporated. Water (25 ml) was added and the mixture was extracted three times with ethyl acetate (3×25 ml). The combined organic layers were washed with brine, dried and evaporated to afford a residue purified by flash chromatography (EE/HP 80/20). The title compound was obtained as yellow powder (129 mg).

MS: M=407.4 (ESI+)

$^1$H-NMR (400 MHz, D$_6$-DMSO): δ (ppm)=1.21 (m, 3H), 1.32 (s, 6H), 1.65 (m, 2H), 1.81 (m, 1H) 1.81 (m, 4H), 1.99 (m, 2H), 2.91 (m, 1H), 3.78 (m, 2H), 7.09 (br, 1H), 7.62 (br, 1H), 8.24 (s, 1H), 10.41 (s, 1H), 13.09 (br, 1H)

Compounds B-7 to B-35 were prepared following the same method:

Example B-7

N-[3-(5-Ethyl-7,7-dimethyl-6-oxo-1,5,6,7-tetrahydro-imidazo[4,5-f]indol-2-yl)-1H-pyrazol-4-yl]-2-phenyl-acetamide N-[3-(5-Ethyl-7,7-dimethyl-6-oxo-1,5,6,7-tetrahydro-imidazo[4,5-f]indol-2-yl)-1H-pyrazol-4-yl]-2-phenyl-acetamide was prepared using 2-(4-amino-1H-pyrazol-3-yl)-5-ethyl-7,7-dimethyl-5,7-dihydro-1H-imidazo[4,5-f]indol-6-one (100 mg, 0.32 mmol) and phenylacetyl chloride (51 μl, 0.38 mmol). The title compound was obtained as yellow powder (48 mg, 34%).

MS: M=429.3 (ESI+)

$^1$H-NMR (400 MHz, D$_6$-DMSO): δ (ppm)=1.19 (m, 3H), 1.32 (s, 6H), 3.82 (m, 4H), 7.40 (m, 1H), 7.45 (m, 5H), 7.79 (br, 1H), 8.13 (m, 2H), 8.24 (s, 1H), 10.35 (s, 1H), 13.01 (br, 1H)

Example B-8

N-[3-(5-Ethyl-7,7-dimethyl-6-oxo-1,5,6,7-tetrahydro-imidazo[4,5-f]indol-2-yl)-1H-pyrazol-4-yl]-3-phenyl-propionamide N-[3-(5-Ethyl-7,7-dimethyl-6-oxo-1,5,6,7-tetrahydro-imidazo[4,5-f]indol-2-yl)-1H-pyrazol-4-yl]-3-phenyl-propionamide was prepared using 2-(4-amino-1H-pyrazol-3-yl)-5-ethyl-7,7-dimethyl-5,7-dihydro-1H-imidazo[4,5-f]indol-6-one (300 mg, 0.96 mmol) and 3-phenyl-propionic acid chloride (157 μl, 1.06 mmol). The title compound was obtained as yellow powder (201 mg, 47%).

MS: M=443.2 (ESI+)

$^1$H-NMR (400 MHz, D$_6$-DMSO): δ (ppm)=1.18 (t, 3H), 1.31 (s, 6H), 2.80 (m, 2H), 3.01 (m, 2H), 3.77 (m, 2H), 7.09 (br, 1H), 7.17 (m, 1H), 7.31 (m, 6H), 8.24 (s, 1H), 10.34 (s, 1H)

Example B-9

N-[3-(5-Ethyl-7,7-dimethyl-6-oxo-1,5,6,7-tetrahydro-imidazo[4,5-f]indol-2-yl)-1H-pyrazol-4-yl]-2-phenyl-butyramide N-[3-(5-Ethyl-7,7-dimethyl-6-oxo-1,5,6,7-tetrahydro-imidazo[4,5-f]indol-2-yl)-1H-pyrazol-4-yl]-2-phenyl-butyramide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-phenylbutyryl chloride (148 μl, 0.88 mmol). The title compound was obtained as yellow powder (69 mg, 19%).

MS: M=457.4 (ESI+)

$^1$H-NMR (400 MHz, D$_6$-DMSO): δ (ppm)=0.88 (m, 3H), 1.10 (m, 3H), 1.34 (s, 6H), 1.85 (m, 1H), 2.18 (m, 1H), 3.67 (t, 1H), 3.78 (br, 2H), 6.98 and 7.19 (s, 1H, tautomeric forms), 7.27 (m, 1H), 7.29 (m, 2H), 7.48 (m, 2H), 7.48 and 7.68 (s, 1H, tautomeric forms), 8.23 (s, 1H), 10.49 (s, 1H), 12.95 (br, 1H), 13.12 (br, 1H)

Example B-10

N-[3-(5-Ethyl-7,7-dimethyl-6-oxo-1,5,6,7-tetrahydro-imidazo[4,5-f]indol-2-yl)-1H-pyrazol-4-yl]-2-thiophen-2-yl-acetamide N-[3-(5-Ethyl-7,7-dimethyl-6-oxo-1,5,6,7-tetrahydro-imidazo[4,5-f]indol-2-yl)-1H-pyrazol-4-yl]-2-thiophen-2-yl-acetamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-phenylbutyryl chloride (148 μl, 0.89 mmol). The title compound was obtained as yellow powder (69 mg, 18%).

MS: M=435.3 (ESI+)

$^1$H-NMR (400 MHz, D$_6$-DMSO): δ (ppm)=1.20 (m, 3H), 1.32 (s, 6H), 3.77 (m, 2H), 4.08 (s, 2H), 7.00 and 7.13 (s, 1H, tautomeric forms), 7.14 (m, 2H), 7.20 and 7.39 (s, 1H, tautomeric forms), 7.54 (s, 1H), 8.26 (s, 1H), 10.51 (d, 1H), 12.95 (d, 1H), 13.18 (d, 1H)

Example B-11

3-Cyano-N-[3-(5-ethyl-7,7-dimethyl-6-oxo-1,5,6,7-tetrahydro-imidazo[4,5-f]indol-2-yl)-1H-pyrazol-4-yl]-benzamide 3-Cyano-N-[3-(5-ethyl-7,7-dimethyl-6-oxo-1,5,6,7-tetrahydro-imidazo[4,5-f]indol-2-yl)-1H-pyrazol-4-yl]-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3-cyano-benzoyl chloride (146 mg, 0.89 mmol). The title compound was obtained as light brown powder (90 mg, 25%).

MS: M=440.3 (ESI+)

$^1$H-NMR (400 MHz, $D_6$-DMSO): δ (ppm)=1.21 (m, 3H), 1.34 (s, 6H), 3.78 (m, 2H), 7.05 and 7.32 (s, 1H, tautomeric forms), 7.48 and 7.71 (s, 1H, tautomeric forms), 7.92 (m, 1H), 8.16 (m, 1H), 8.35 (m, 2H), 8.48 (m, 1H), 11.79 (d, 1H), 13.20 (d, 1H), 13.35 (d, 2H)

Example B-12

N-[3-(5-Ethyl-7,7-dimethyl-6-oxo-1,5,6,7-tetrahydro-imidazo[4,5-f]indol-2-yl)-1H-pyrazol-4-yl]-3-trifluoromethyl-benzamide N-[3-(5-Ethyl-7,7-dimethyl-6-oxo-1,5,6,7-tetrahydro-imidazo[4,5-f]indol-2-yl)-1H-pyrazol-4-yl]-3-trifluoromethyl-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3-(trifluoromethyl)benzoyl chloride (131 μl, 0.89 mmol). The title compound was obtained as light brown powder (195 mg, 50%).

MS: M=483.4 (ESI+)

$^1$H-NMR (400 MHz, $D_6$-DMSO): δ (ppm)=1.09 (m, 3H), 1.34 (s, 6H), 3.77 (m, 2H), 7.06 and 7.24 (s, 1H, tautomeric forms), 7.14 (m, 2H), 7.50 and 7.64 (s, 1H, tautomeric forms), 7.96 (m, 1H), 8.08 (m, 1H), 8.37 (m, 3H), 11.86 (d, 1H), 13.31 (br, 2H)

Example B-13

N-[3-(5-Ethyl-7,7-dimethyl-6-oxo-1,5,6,7-tetrahydro-imidazo[4,5-f]indol-2-yl)-1H-pyrazol-4-yl]-2,6-dimethoxy-benzamide N-[3-(5-Ethyl-7,7-dimethyl-6-oxo-1,5,6,7-tetrahydro-imidazo[4,5-f]indol-2-yl)-1H-pyrazol-4-yl]-2,6-dimethoxy-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2,6-dimethoxybenzoyl chloride (178 mg, 0.87 mmol). The title compound was obtained as light brown powder (180 mg, 47%).

MS: M=475.4 (ESI+)

$^1$H-NMR (400 MHz, $D_6$-DMSO): δ (ppm)=1.17 (m, 3H), 1.28 (s, 6H), 3.73 (m, 2H), 3.78 (s, 6H), 6.82 (d, 2H), 7.00 and 7.19 (s, 1H, tautomeric forms), 7.46 (m, 2H), 8.39 (s, 1H), 10.24 (s, 1H), 13.00 (br, 1H), 13.25 (br, 2H)

Example B-14

Isoxazole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide Isoxazole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and isoxazole-5-carbonyl chloride (78 μl, 0.87 mmol). The title compound was obtained as light brown powder (76 mg, 23%).

MS: M=406.4 (ESI+)

$^1$H-NMR (400 MHz, $D_6$-DMSO): δ (ppm)=1.22 (m, 3H), 1.35 (m, 6H), 3.78 (m, 2H), 3.78 (s, 6H), 7.04 and 7.29 (s, 1H, tautomeric forms), 7.29 (s, 1H), 7.46 and 7.71 (d, 1H, tautomeric forms), 8.40 (s, 1H), 8.91 (s, 1H), 11.52 (m, 1H), 13.15 (br, 1H), 13.40 (br, 1H)

Example B-15

Furan-2-carboxylic acid[3-(5-ethyl-7,7-dimethyl-6-oxo-1,5,6,7-tetrahydro-imidazo[4,5-f]indol-2-yl)-1H-pyrazol-4-yl]-amide Furan-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-furoyl chloride (87 μl, 0.87 mmol). The title compound was obtained as brown powder (147 mg, 45%).

MS: M=405.4 (ESI+)

$^1$H-NMR (400 MHz, $D_6$-DMSO): δ (ppm)=1.22 (m, 3H), 1.35 (m, 6H), 3.78 (m, 2H), 3.78 (s, 6H), 6.78 (m, 1H), 7.03 and 7.33 (s, 1H, tautomeric forms), 7.29 (s, 1H), 7.45 and 7.73 (d, 1H, tautomeric forms), 8.07 (s, 1H), 8.34 (s, 1H), 11.27 (m, 1H), 13.11 (br, 1H), 13.30 (br, 1H)

Example B-16

3-Cyclopentyl-N-[3-(5-ethyl-7,7-dimethyl-6-oxo-1,5,6,7-tetrahydro-imidazo[4,5-f]indol-2-yl)-1H-pyrazol-4-yl]-propionamide 3-Cyclopentyl-N-[3-(5-ethyl-7,7-dimethyl-6-oxo-1,5,6,7-tetrahydro-imidazo[4,5-f]indol-2-yl)-1H-pyrazol-4-yl]-propionamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and cyclopentylpropionyl chloride (136 ml, 0.89 mmol. The title compound was obtained as brown powder (177 mg, 50%).

MS: M=435.5 (ESI+)

$^1$H-NMR (400 MHz, $D_6$-DMSO): δ (ppm)=1.19 (m, 5H), 1.32 (m, 6H), 1.49 (m, 2H), 1.60 (m, 2H), 1.71 (m, 2H), 1.81 (m, 2H), 3.78 (m, 2H), 7.03 and 7.29 (s, 1H, tautomeric forms), 7.45 and 7.68 (d, 1H, tautomeric forms), 8.23 (s, 1H), 10.35 (s, 1H), 13.10 (br, 2H)

Example B-17

N-[3-(5-Ethyl-7,7-dimethyl-6-oxo-1,5,6,7-tetrahydro-imidazo[4,5-f]indol-2-yl)-1H-pyrazol-4-yl]-3,3-dimethyl-butyramide N-[3-(5-Ethyl-7,7-dimethyl-6-oxo-1,5,6,7-tetrahydro-imidazo[4,5-f]indol-2-yl)-1H-pyrazol-4-yl]-3,3-dimethyl-butyramide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and tert-butylacetyl chloride (123 μl, 0.89 mmol). The title compound was obtained as brown powder (142 mg, 43%).

MS: M=409.5 (ESI+)

$^1$H-NMR (400 MHz, D$_6$-DMSO): δ (ppm)=1.08 (s, 9H), 1.19 (m, 5H), 1.32 (m, 6H), 3.79 (m, 2H), 7.01 and 7.29 (s, 1H, tautomeric forms), 7.41 and 7.68 (d, 1H, tautomeric forms), 8.25 (s, 1H), 10.29 (s, 1H), 12.98 (br, 2H), 13.13 (br, 1H)

Example B-18

N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-propionamide N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-propionamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and pivaloyl chloride (109 μl, 0.89 mmol). The title compound was obtained as brown powder (171 mg, 53%).

MS: M=395.5 (ESI+)

$^1$H-NMR (400 MHz, D$_6$-DMSO): δ (ppm)=1.19 (m, 3H), 1.33 (s, 15H), 3.77 (m, 2H), 7.01 and 7.23 (s, 1H, tautomeric forms), 7.42 and 7.63 (d, 1H, tautomeric forms), 10.74 (s, 1H), 13.09 (br, 2H)

Example B-19

2-Ethyl-N-[3-(5-ethyl-7,7-dimethyl-6-oxo-1,5,6,7-tetrahydro-imidazo[4,5-f]indol-2-yl)-1H-pyrazol-4-yl]-butyramide 2-Ethyl-N-[3-(5-ethyl-7,7-dimethyl-6-oxo-1,5,6,7-tetrahydro-imidazo[4,5-f]indol-2-yl)-1H-pyrazol-4-yl]-butyramide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-ethylbutyryl chloride (121 μl, 0.87 mmol). The title compound was obtained as yellow powder (230 mg, 70%).

MS: M=409.4 (ESI+)

$^1$H-NMR (400 MHz, D$_6$-DMSO): δ (ppm)=0.90 (t, 6H), 1.21 (t, 3H), 1.32 (s, 6H), 1.60 (m, 4H), 3.78 (m, 2H), 7.01 and 7.31 (s, 1H, tautomeric forms), 7.44 and 7.68 (d, 1H, tautomeric forms), 8.26 (s, 1H), 10.43 (s, 1H), 13.09 (br, 2H)

Example B-20

N-[3-(5-Ethyl-7,7-dimethyl-6-oxo-1,5,6,7-tetrahydro-imidazo[4,5-f]indol-2-yl)-1H-pyrazol-4-yl]-3-methyl-butyramide N-[3-(5-Ethyl-7,7-dimethyl-6-oxo-1,5,6,7-tetrahydro-imidazo[4,5-f]indol-2-yl)-1H-pyrazol-4-yl]-3-methyl-butyramide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and isovaleryl chloride (108 μl, 0.89 mmol). The title compound was obtained as yellow powder (240 mg, 75%).

MS: M=395.4 (ESI+)

$^1$H-NMR (400 MHz, D$_6$-DMSO): δ (ppm)=1.00 (s, 6H), 1.19 (t, 3H), 1.32 (s, 6H), 2.15 (m, 1H), 2.34 (d, 2H), 3.77 (m, 2H), 7.01 and 7.31 (s, 1H, tautomeric forms), 7.44 and 7.70 (d, 1H, tautomeric forms), 8.25 (s, 1H), 10.30 (s, 1H), 13.09 (br, 2H)

Example B-21

3-Chloro-N-[3-(5-ethyl-7,7-dimethyl-6-oxo-1,5,6,7-tetrahydro-imidazo[4,5-f]indol-2-yl)-1H-pyrazol-4-yl]-2,2-dimethyl-propionamide 3-Chloro-N-[3-(5-ethyl-7,7-dimethyl-6-oxo-1,5,6,7-tetrahydro-imidazo[4,5-f]indol-2-yl)-1H-pyrazol-4-yl]-2,2-dimethyl-propionamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3-chloropivaloyl chloride (115 μl, 0.89 mmol). The title compound was obtained as yellow powder (239 mg, 69%).

MS: M=428.2 (ESI+)

$^1$H-NMR (400 MHz, D$_6$-DMSO): ø(ppm)=1.06 (t, 3H), 1.20 (m, 6H), 1.45 (s, 6H), 3.80 (m, 4H), 7.02 and 7.25 (s, 1H, tautomeric forms), 7.44 and 7.64 (d, 1H, tautomeric forms), 8.27 (s, 1H), 10.89 (s, 1H), 13.12 (br, 2H)

Example B-22

N-[3-(5-Ethyl-7,7-dimethyl-6-oxo-1,5,6,7-tetrahydro-imidazo[4,5-f]indol-2-yl)-1H-pyrazol-4-yl]-2-methoxy-acetamide N-[3-(5-Ethyl-7,7-dimethyl-6-oxo-1,5,6,7-tetrahydro-imidazo[4,5-f]indol-2-yl)-1H-pyrazol-4-yl]-2-methoxy-acetamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and methoxyacetyl chloride (81 μl, 0.89 mmol). The title compound was obtained as light brown powder (171 mg, 55%).

MS: M=383.3 (ESI+)

$^1$H-NMR (400 MHz, D$_6$-DMSO): δ (ppm)=1.62 (t, 3H), 1.75 (s, 6H), 4.00 (s, 3H), 4.19 (m, 2H), 4.52 (s, 2H), 7.55 (br, 1H), 7.98 (br, 1H), 8.72 (s, 1H), 11.42 (s, 1H), 13.52 (br, 2H)

Example B-23

Thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide Thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and thiophene-2-carbonyl chloride (94 μl, 0.89 mmol). The title compound was obtained as yellow powder (54 mg, 15%).

MS: M=421.1 (ESI+)

$^1$H-NMR (400 MHz, D$_6$-DMSO): δ (ppm)=1.22 (m, 3H), 1.35 (m, 6H), 3.79 (m, 2H), 7.04 and 7.41 (d, 1H, tautomeric forms), 7.36 (m, 1H), 7.46 and 7.79 (d, 1H, tautomeric forms), 7.89 (s, 1H), 7.95 (m, 1H), 8.31 (m, 1H), 11.37 (d, 1H), 13.14 (d, 1H), 13.30 (d, 1H)

Example B-24

3-Chloro-N-[3-(5-ethyl-7,7-dimethyl-6-oxo-1,5,6,7-tetrahydro-imidazo[4,5-f]indol-2-yl)-1H-pyrazol-4-yl]-benzamide 3-Chloro-N-[3-(5-ethyl-7,7-dimethyl-6-oxo-1,5,6,7-tetrahydro-imidazo[4,5-f]indol-2-yl)-1H-pyrazol-4-yl]-benzamide was prepared using 2-(4-amino-1H-pyrazol-3-yl)-5-ethyl-7,7-dimethyl-5,7-dihydro-1H-imidazo[4,5-f]indol-6- one (250 mg, 0.81 mmol) and 3-chlorobenzoyl chloride (113 μl, 0.89 mmol). The title compound was obtained as light brown powder (105 mg, 29%).

MS: M=449.1 (ESI+)

$^1$H-NMR (400 MHz, D$_6$-DMSO): δ (ppm)=1.20 (m, 3H), 1.34 (s, 6H), 3.77 (m, 2H), 7.05 and 7.30 (d, 1H, tautomeric forms), 7.48 and 7.70 (d, 1H, tautomeric forms), 7.77 (m, 2H), 8.03 (m, 2H), 8.38 (s, 1H), 11.69 (d, 1H), 13.22 (m, 2H)

Example B-25

N-[3-(5-Ethyl-7,7-dimethyl-6-oxo-1,5,6,7-tetrahydro-imidazo[4,5-f]indol-2-yl)-1H-pyrazol-4-yl]-3-methyl-benzamide N-[3-(5-Ethyl-7,7-dimethyl-6-oxo-1,5,6,7-tetrahydro-imidazo[4,5-f]indol-2-yl)-1H-pyrazol-4-yl]-3-methyl-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and m-toluyl acid chloride (116 μl, 0.89 mmol). The title compound was obtained as yellow powder (112 mg, 32%).

MS: M=429.2 (ESI+)

$^1$H-NMR (400 MHz, D$_6$-DMSO): δ (ppm)=1.21 (m, 3H), 1.35 (m, 6H), 3.79 (m, 2H), 7.05 and 7.32 (d, 1H, tautomeric forms), 7.47 (m, 1H), 7.51 and 7.71 (d, 1H, tautomeric forms), 7.88 (m, 2H), 8.39 (s, 1H), 11.55 (d, 1H), 13.22 (m, 1H)

Example B-26

N-[3-(5-Ethyl-7,7-dimethyl-6-oxo-1,5,6,7-tetrahydro-imidazo[4,5-f]indol-2-yl)-1H-pyrazol-4-yl]-2-phenoxy-acetamide N-[3-(5-Ethyl-7,7-dimethyl-6-oxo-1,5,6,7-tetrahydro-imidazo[4,5-f]indol-2-yl)-1H-pyrazol-4-yl]-2-phenoxy-acetamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and phenoxy acetyl chloride (122 μl, 0.89 mmol). The title compound was obtained as yellow powder (218 mg, 61%).

MS: M=445.3 (ESI+)

$^1$H-NMR (400 MHz, D$_6$-DMSO): δ (ppm)=1.22 (m, 3H), 1.33 (s, 6H), 3.79 (m, 2H), 4.83 (s, 2H), 7.02 (m, 2H), 7.27 (m, 2H), 7.39 (m, 2H), 7.48 (br, 1H), 8.32 (s. 1H), 11.35 (d, 1H), 13.15 (br, 2H)

Example B-27

Quinoxaline-2-carboxylic acid[3-(5-ethyl-7,7-dimethyl-6-oxo-1,5,6,7-tetrahydro-imidazo[4,5-f]indol-2-yl)-1H-pyrazol-4-yl]-amide Quinoxaline-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-quinoxalinecarbonyl chloride (170 mg, 0.89 mmol). The title compound was obtained as yellow powder (158 mg, 42%).

MS: M=467.3 (ESI+)

$^1$H-NMR (400 MHz. D$_6$-DMSO): δ (ppm)=1.19 (m, 3H), 1.39 (s, 6H), 3.82 (m, 2H), 7.07 and 7.41 (d, 1H, tautomeric forms), 7.55 and 7.80 (d, 1H, tautomeric forms), 8.11 (m, 2H), 8.26 (d, 1H), 8.47 (m, 2H), 9.64 (s, 1H), 12.46 (d, 1H), 13.21 (br, 2H)

Example B-28

N-[3-(5-Ethyl-7,7-dimethyl-6-oxo-1,5,6,7-tetrahydro-imidazo[4,5-f]indol-2-yl)-1H-pyrazol-4-yl]-4-fluoro-3-methyl-benzamide N-[3-(5-Ethyl-7,7-dimethyl-6-oxo-1,5,6,7-tetrahydro-imidazo[4,5-f]indol-2-yl)-1H-pyrazol-4-yl]-4-fluoro-3-methyl-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 4-fluoro-3-methylbenzoyl chloride (125 μl, 0.89 mmol). The title compound was obtained as yellow powder (220 mg, 61%).

MS: M=447.3 (ESI+)

$^1$H-NMR (400 MHz, D$_6$-DMSO): ø(ppm)=1.20 (m, 3H), 1.35 (s, 6H), 2.41 (s, 3H), 3.79 (m, 2H), 7.04 and 7.33 (d, 1H, tautomeric forms), 7.44 and 7.72 (d, 1H, tautomeric forms), 7.49 (m, 1H), 7.93 (m, 2H), 8.37 (s, 1H), 11.52 (d, 1H), 13.21 (m, 2H)

Example B-29

N-[3-(5-Ethyl-7,7-dimethyl-6-oxo-1,5,6,7-tetrahydro-imidazo[4,5-f]indol-2-yl)-1H-pyrazol-4-yl]-3,4-difluoro-benzamide N-[3-(5-Ethyl-7,7-dimethyl-6-oxo-1,5,6,7-tetrahydro-imidazo[4,5-f]indol-2-yl)-1H-pyrazol-4-yl]-3,4-difluoro-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3,4-difluorobenzoyl chloride (111 μl, 0.89 mmol). The title compound was obtained as yellow powder (242 mg, 66%).

MS: M=451.3 (ESI+)

$^1$H-NMR (400 MHz, D$_6$-DMSO): δ (ppm)=1.19 (m, 3H), 1.34 (s, 6H), 2.41 (s, 3H), 3.79 (m, 2H), 7.04 and 7.32 (d, 1H, tautomeric forms), 7.46 and 7.72 (d, 1H, tautomeric forms), 7.79 (m, 1H), 7.92 (m, 1H), 7.99 (m, 1H), 8.37 (s, 1H), 11.52 (s, 1H), 13.25 (br, 2H)

Example B-30

2-Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide 2-Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and trans-2-phenyl cyclopropan-1-carbonyl chloride (137 μl, 0.89 mmol). The title compound was obtained as yellow powder (216 mg, 59%).

MS: M=455.4 (ESI+)

$^1$H-NMR (400 MHz, D$_6$-DMSO): δ (ppm)=1.20 (m, 3H), 1.30 (s, 6H), 1.53 (m, 2H), 2.20 (m, 1H), 2.48 (m, 1H), 3.76 (m, 2H), 7.01 and 7.20 (d, 1H, tautomeric forms), 7.26 (m, 5H), 7.42 and 7.69 (d, 1H, tautomeric forms), 8.26 (s, 1H), 10.53 (s, 1H), 13.01 (br, 2H)

Example B-31

N-[3-(5-Ethyl-7,7-dimethyl-6-oxo-1,5,6,7-tetrahydro-imidazo[4,5-f]indol-2-yl)-1H-pyrazol-4-yl]-3,4,5-trimethoxy-benzamide N-[3-(5-Ethyl-7,7-dimethyl-6-oxo-1,5,6,7-tetrahydro-imidazo[4,5-f]indol-2-yl)-1H-pyrazol-4-yl]-3,4,5-trimethoxy-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3,4,5-trimethoxybenzoyl chloride (204 mg, 0.89 mmol). The title compound was obtained as yellow powder (177 mg, 43%).

MS: M=505.3 (ESI+)

$^1$H-NMR (400 MHz, D$_6$-DMSO): δ (ppm)=1.20 (m, 3H), 1.33 (s, 6H), 3.79 (m, 5H), 3.99 (d, 6H), 7.05 and 7.17 (d, 1H, tautomeric forms), 7.32 (d, 2H), 7.47 and 7.55 (d, 1H, tautomeric forms), 8.35 (s, 1H), 11.49 (d, 1H), 13.22 (br, 2H)

Example B-32

N-[3-(5-Ethyl-7,7-dimethyl-6-oxo-1,5,6,7-tetrahydro-imidazo[4,5-f]indol-2-yl)-1H-pyrazol-4-yl]-3,5-difluoro-benzamide N-[3-(5-Ethyl-7,7-dimethyl-6-oxo-1,5,6,7-tetrahydro-imidazo[4,5-f]indol-2-yl)-1H-pyrazol-4-yl]-3,5-difluoro-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3,5-difluorobenzoyl chloride (111 ml, 0.89 mmol). The title compound was obtained as brown powder (112 mg, 31%).

MS: M=451.1 (ESI+)

$^1$H-NMR (400 MHz, D$_6$-DMSO): δ (ppm)=1.20 (m, 3H), 1.33 (s, 6H), 3.77 (m, 2H), 7.05 and 7.20 (d, 1H, tautomeric forms), 7.49 and 7.60 (d, 1H, tautomeric forms), 7.63 (m, 3H), 8.37 (s, 1H), 11.45 (d, 1H), 13.25 (br, 2H)

Example B-33

N-[3-(5-Ethyl-7,7-dimethyl-6-oxo-1,5,6,7-tetrahydro-imidazo[4,5-f]indol-2-yl)-1H-pyrazol-4-yl]-3,4,5-trifluoro-benzamide N-[3-(5-Ethyl-7,7-dimethyl-6-oxo-1,5,6,7-tetrahydro-imidazo[4,5-f]indol-2-yl)-1H-pyrazol-4-yl]-3,4,5-trifluoro-benzamide was prepared using 2-(4-amino-1H-pyrazol-3-yl)-5-ethyl-7,7-dimethyl-5,7-dihydro-1H-imidazo[4,5-f]indol-6-one (250 mg, 0.80 mmol) and 3,4,5-trifluorobenzoyl chloride (116 μl, 0.88 mmol). The title compound was obtained as white powder (86 mg, 23%).

MS: M=469.2 (ESI+)

$^1$H-NMR (400 MHz, D$_6$-DMSO): ∅(ppm)=1.20 (m, 3H), 1.33 (s, 6H), 3.78 (m, 2H), 7.10 (br, 1H), 7.59 (br, 1H), 7.89 (m, 2H), 8.34 (s, 1H), 9.41 (br, 1H), 13.24 (br, 2H)

Example B-34

Cyclopropanecarboxylic acid[3-(5-isopropyl-7,7-dimethyl-6-oxo-1,5,6,7-tetrahydro-imidazo[4,5-f]indol-2-yl)-1H-pyrazol-4-yl]-amide Cyclopropanecarboxylic acid[3-(5-isopropyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-isopropyl-7,7-dimethyl-5,7-dihydro-1H-imidazo[4,5-f]indol-6-one (325 mg, 0.90 mmol) and cyclopropanecarbonyl chloride (92 μl, 0.99 mmol). The title compound was obtained as dark green powder (85 mg, 22%).

MS: M=393.2 (ESI+)

$^1$H-NMR (400 MHz, D$_6$-DMSO): δ (ppm)=0.89 (d, 6H), 1.31 (s, 6H), 1.46 (m, 6H), 1.90 (m, 1H), 4.55 (m, 1H), 7.11 and 7.41 (d, 1H, tautomeric forms), 7.44 and 7.69 (d, 1H, tautomeric forms), 8.18 (d, 1H), 10.60 (d, 1H), 12.94 (d, 1H), 13.12 (d, 1H)

Example B-35

Furan-2-carboxylic acid[3-(5-isopropyl-7,7-dimethyl-6-oxo-1,5,6,7-tetrahydro-imidazo[4,5-f]indol-2-yl)-1H-pyrazol-4-yl]-amide Furan-2-carboxylic acid[3-(5-isopropyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-isopropyl-7,7-dimethyl-5,7-dihydro-1H-imidazo[4,5-f]indol-6-one (325 mg, 0.90 mmol) and 2-furoyl chloride (102 μl, 0.99 mmol). The title compound was obtained as dark green powder (180 mg, 44%).

MS: M=419.2 (ESI+)

$^1$H-NMR (400 MHz, D$_6$-DMSO): δ (ppm)=1.33 (m, 6H), 1.49 (m, 6H), 4.57 (m, 1H), 6.77 (s, 1H), 7.13 and 7.39 (d, 1H, tautomeric forms), 7.29 (s, 1H), 7.43 and 7.71 (d, 1H, tautomeric forms), 8.06 (d, 1H), 8.35 (s, 1H), 11.26 (s, 1H), 12.98 (d, 1H), 13.23 (d, 1H)

Example B-36

Cyclopropanecarboxylic acid[3-(5,7,7-triethyl-6-oxo-1,5,6,7-tetrahydro-imidazo[4,5-f]indol-2-yl)-1H-pyrazol-4-yl]-amide Cyclopropanecarboxylic acid[3-(5,7,7-triethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5,7,7-triethyl-5,7-dihydro-1H-imidazo[4,5-f]indol-6-one (137.7 mg, 0.407 mmol) and cyclopropanecarbonyl chloride (46.8 mg, 0.448 mmol). 57 mg (34%) of the title compound were obtained.

MS: M=407.2 (ESI+)

$^1$H-NMR (400 MHz, DMSO): δ (ppm)=0.47 (t, 6H), 0.89 (d, 4H), 1.18 (t, 3H), 1.25 (m, 1H), 1.81 (q, 4H), 3.80 (q, 2H), 7.02 and 7.31 (s, 1H, two tautomeric forms), 7.31 and 7.60 (s, 1H, two tautomeric forms), 8.19 (s, 1H), 10.60 (br, 1H), 13.00 (br, 1H), 13.10 (br, 1H)

Example B-37

Cyclopropanecarboxylic acid[3-(7,7-diethyl-5-isopropyl-6-oxo-1,5,6,7-tetrahydro-imidazo[4,5-f]indol-2-yl)-1H-pyrazol-4-yl]-amide Cyclopropanecarboxylic acid[3-(7,7-diethyl-5-isopropyl-6-oxo-1,5,6,7-tetrahydro-imidazo[4,5-f]indol-2-yl)-1H-pyrazol-4-yl]-amide was prepared using 2-(4-Amino-1H-pyrazol-3-yl)-7,7-diethyl-5-isopropyl-5,7-dihydro-1H-imidazo[4,5-f]indol-6-one (150 mg, 0.43 mmol) and cyclopropanecarbonyl chloride (45 mg, 0.43 mmol). 30 mg (17%) of the title compound were obtained.

MS: M=421.4 (ESI+)

$^1$H-NMR (400 MHz, DMSO): δ (ppm)=0.43 (t, 6H), 0.87 (m, 4H), 1.45 (d, 6H), 1.79 (m, 4H), 1.87 (m, 1H), 4.56 (m, 1H), 7.11 and 7.31 (s, 1H, two tautomeric forms), 7.44 and 7.60 (s, 1H, two tautomeric forms), 8.19 (s, 1H), 10.55 and 10.60 (br, 1H, two tautomeric forms), 12.92 and 12.99 (br, 1H, two tautomeric forms), 13.10 and 13.15 (br, 1H, two tautomeric forms)

Example C

General Procedure C

A mixture of appropriate acid (0.54 mmol), HOBt (78 mg, 0.58 mmol), EDC (111 mg, 0.58 mmol), appropriate amino pyrazole (0.48 mmol) was dissolved in DMF (6 ml) and stirred at room temperature for 15 hours. Water (50 ml) was added and the mixture was extracted three times with ethyl acetate (3×50 ml). The combined organic layers were washed with brine, dried and evaporated to afford a residue purified by High Performance Liquid Chromatography (HPLC).

The following compounds were made using general procedure C:

Example C-1

N-[3-(5-Ethyl-7,7-dimethyl-6-oxo-1,5,6,7-tetrahydro-imidazo[4,5-f]indol-2-yl)-1H-pyrazol-4-yl]-2,6-difluoro-benzamide N-[3-(5-Ethyl-7,7-dimethyl-6-oxo-1,5,6,7-tetrahydro-imidazo[4,5-f]indol-2-yl)-1H-pyrazol-4-yl]-2,6-difluoro-benzamide was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and 2,6-difluorobenzoic acid. The title compound was obtained as off-white powder (24 mg).

MS: M=450.8 (API+)

$^1$H-NMR (400 MHz, D$_6$-DMSO): δ (ppm)=1.16 (t, 3H), 1.30 (s, 6H), 3.75 (q, 2H), 7.05 (br, 1H), 7.42 (m, 3H), 7.65 (br, 1H), 7.76 (m, 1H), 7.83 (m, 1H), 9.03 (s, 1H), 11.47 (s, 1H)

Example C-2

N-[3-(5-Ethyl-7,7-dimethyl-6-oxo-1,5,6,7-tetrahydro-imidazo[4,5-f]indol-2-yl)-1H-pyrazol-4-yl]-isonicotinamide N-[3-(5-Ethyl-7,7-dimethyl-6-oxo-1,5,6,7-tetrahydro-imidazo[4,5-f]indol-2-yl)-1H-pyrazol-4-yl]-isonicotinamide was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and isonicotinic acid (66 mg, 0.54 mmol). The title compound was obtained as off-white powder (76 mg).

MS: M=416.0 (API+)

$^1$H-NMR (500 MHz, D$_6$-DMSO): δ (ppm)=1.22 (t, J=6.95 Hz, 3H), 1.35 (s, 6H), 3.80 (m, 2H), 7.05, 7.40, 7.47, 7.80 (br, 2H, tautomeric forms), 7.95 (m, 2H), 8.42 (s, 1H), 8.95 (m, 2H), 11.66 (br, 1H), 13.27 (br, 2H)

Example C-3

Pyridine-2-carboxylic acid[3-(5-ethyl-7,7-dimethyl-6-oxo-1,5,6,7-tetrahydro-imidazo[4,5-f]indol-2-yl)-1H-pyrazol-4-yl]-amide Pyridine-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f] indol-6-one (250 mg, 0.81 mmol) and picolinic acid (109 mg, 0.89 mmol). The title compound was obtained as orange powder (121 mg, 36%).

MS: M=416.4 (ESI+)

$^1$H-NMR (500 MHz, D$_6$-DMSO): δ (ppm)=1.22 (m, 3H), 1.36 (s, 6H), 3.77 (m, 2H), 7.03 and 7.33 (d, 1H, tautomeric forms), 7.45 and 7.71 (d, 1H, tautomeric forms), 7.73 (m, 1H), 8.10 (m, 1H), 8.18 (m, 1H), 8.49 (s, 1H), 8.95 (s, 1H), 12.21 (d, 1H), 13.03 (d, 2H), 13.30 (d, 1H)

Example C-4

N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-butyramide N-[3-(5-Ethyl-7,7-dimethyl-6-oxo-1,5,6,7-tetrahydro-imidazo[4,5-f]indol-2-yl)-1H-pyrazol-4-yl]-2,2-dimethyl-butyramide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2,2-dimethylbutyric acid (110 μl, 0.89 mmol). The title compound was obtained as yellow powder (186 mg, 56%).

MS: M=409.3 (ESI+)

$^1$H-NMR (500 MHz, D$_6$-DMSO): ø(ppm)=0.84 (t, 3H), 1.20 (t, 3H), 1.31 (m, 12H), 1.67 (m, 2H), 3.78 (br, 2H), 7.01 and 7.25 (d, 1H, tautomeric forms), 7.45 and 7.63 (d, 1H, tautomeric forms), 8.25 (s, 1H), 10.75 (s, 1H), 13.10 (br, 2H)

Example C-5

5-Methyl-thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide 5-Methyl-thiophene-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 5-methylthiophen-2-carboxylic acid (125 mg, 0.89 mmol). The title compound was obtained as yellow powder (166 mg, 47%).

MS: M=435.2 (ESI+)

$^1$H-NMR (500 MHz, D$_6$-DMSO): δ (ppm)=1.20 (m, 3H), 1.36 (s, 6H), 2.56 (s, 3H), 3.79 (m, 2H), 6.89 (s, 1H), 7.46 (m, 1H), 7.69 (m, 1H), 7.79 (m, 1H), 8.30 (s, 1H), 11.21 (s, 1H), 13.12 (d, 2H), 13.30 (d, 1H)

Example C-6

(E)-N-[3-(5-Ethyl-7,7-dimethyl-6-oxo-1,5,6,7-tetrahydro-imidazo[4,5-f]indol-2-yl)-1H-pyrazol-4-yl]-3-phenyl-acrylamide (E)-N-[3-(5-Ethyl-7,7-dimethyl-6-oxo-1,5,6,7-tetrahydro-imidazo[4,5-f]indol-2-yl)-1H-pyrazol-4-yl]-3-phenyl-acrylamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and cinnamoic acid (131 mg, 0.89 mmol). The title compound was obtained as yellow powder (86 mg, 24%).

MS: M=441.2 (ESI+)

$^1$H-NMR (500 MHz, D$_6$-DMSO): δ (ppm)=1.21 (m, 3H), 1.34 (s, 6H), 3.79 (m, 2H), 7.11 (d, 1H), 7.45 (m, 4H), 7.66 (d, 1H), 7.80 (m, 3H), 8.38 (s, 1H), 10.59 (s, 1H), 13.25 (br, 2H)

Example C-7

N-[3-(5-Ethyl-7,7-dimethyl-6-oxo-1,5,6,7-tetrahydro-imidazo[4,5-f]indol-2-yl)-1H-pyrazol-4-yl]-2-phenoxy-propionamide N-[3-(5-Ethyl-7,7-dimethyl-6-oxo-1,5,6,7-tetrahydro-imidazo[4,5-f]indol-2-yl)-1H-pyrazol-4-yl]-2-phenoxy-propionamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-phenoxypropionic acid (147 mg, 0.89 mmol). The title compound was obtained as white powder (15 mg, 4%).

MS: M=459.3 (ESI+)

$^1$H-NMR (500 MHz, $D_6$-DMSO): δ (ppm)=1.21 (br, 3H), 1.32 (s, 6H), 1.61 (d, 3H), 3.78 (br, 2H), 5.09 (m, 2H), 6.99 (m, 2H), 7.27 (m, 4H), 7.48 (m, 1H), 8.30 (s, 1H), 11.29 (br, 1H), 13.12 (br, 2H)

Example C-8

N-[3-(5-Ethyl-7,7-dimethyl-6-oxo-1,5,6,7-tetrahydro-imidazo[4,5-f]indol-2-yl)-1H-pyrazol-4-yl]-2-(2-methoxy-phenoxy)-acetamide N-[3-(5-Ethyl-7,7-dimethyl-6-oxo-1,5,6,7-tetrahydro-imidazo[4,5-f]indol-2-yl)-1H-pyrazol-4-yl]-2-(2-methoxy-phenoxy)-acetamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and (2-methoxyphenoxy)acetic acid (161 mg, 0.88 mmol). The title compound was obtained as yellow powder (28 mg, 7%).

MS: M=475.2 (API+)

$^1$H-NMR (500 MHz, $D_6$-DMSO): δ (ppm)=1.19 (m, 3H), 1.31 (s, 6H), 3.75 (m, 2H), 3.88 (s, 3H), 4.79 (s, 2H), 6.99 (m, 5H), 7.37 (s, 1H), 8.34 (s, 1H), 11.18 (s, 1H), 13.12 (br, 2H)

Example C-9

2-Cyclopentyl-N-[3-(5-ethyl-7,7-dimethyl-6-oxo-1,5,6,7-tetrahydro-imidazo[4,5-f]indol-2-yl)-1H-pyrazol-4-yl]-acetamide 2-Cyclopentyl-N-[3-(5-ethyl-7,7-dimethyl-6-oxo-1,5,6,7-tetrahydro-imidazo[4,5-f]indol-2-yl)-1H-pyrazol-4-yl]-acetamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and cyclopentylacetic acid (111 μl, 0.89 mmol). The title compound was obtained as yellow powder (74 mg, 22%).

MS: M=421.3 (ESI+)

$^1$H-NMR (500 MHz, $D_6$-DMSO): δ (ppm)=1.21 (m, 3H), 1.32 (m, 6H), 1.54 (m, 2H), 1.63 (m, 2H), 1.84 (m, 2H), 2.30 (m, 1H), 3.78 (m, 2H), 7.01 and 7.29 (s, 1H, tautomeric forms), 7.45 and 7.66 (d, 1H, tautomeric forms), 8.24 (s, 1H), 10.33 (s, 1H), 13.08 (br, 2H)

Example C-10

Benzo[1,3]dioxole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide Benzo[1,3]dioxole-5-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and piperonylic acid (147 mg, 0.89 mmol). The title compound was obtained as grey powder (150 mg, 40%).

MS: M=459.1 (API+)

$^1$H-NMR (500 MHz, $D_6$-DMSO): δ (ppm)=1.20 (m, 3H), 1.35 (m, 6H), 3.78 (m, 2H), 6.21 (s, 2H), 7.23 (m, 2H), 7.66 (m, 3H), 8.36 (s, 1H), 11.33 (s, 1H), 13.20 (br, 2H)

Example C-11

Pyrazine-2-carboxylic acid[3-(5-ethyl-7,7-dimethyl-6-oxo-1,5,6,7-tetrahydro-imidazo[4,5-f]indol-2-yl)-1H-pyrazol-4-yl]-amide Pyrazine-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and pyrazine-2-carboxylic acid (109 mg, 0.89 mmol). The title compound was obtained as yellow powder (19 mg, 6%).

MS: M=417.1 (API+)

$^1$H-NMR (500 MHz, $D_6$-DMSO): δ (ppm)=1.20 (m, 3H), 1.35 (m, 6H), 3.79 (m, 2H), 7.09 (br, 1H), 7.72 (br, 1H), 8.50 (s, 1H), 9.02 (m, 2H), 9.35 (s, 1H), 12.22 (s, 1H), 13.20 (br, 2H)

Example C-12

Benzofuran-2-carboxylic acid[3-(5-ethyl-7,7-dimethyl-6-oxo-1,5,6,7-tetrahydro-imidazo[4,5-f indol-2-yl)-1H-pyrazol-4-yl]-amide Benzofuran-2-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and benzofuran-2-carboxylic acid (143 mg, 0.89 mmol). The title compound was obtained as yellow powder (36 mg, 10%).

MS: M=455.1 (API+)

$^1$H-NMR (500 MHz, $D_6$-DMSO): δ (ppm)=1.22 (m, 3H), 1.40 (m, 6H), 3.80 (m, 2H), 7.05 and 7.40 (s, 1H, tautomeric forms), 7.41 (m, 1H), 7.47 (m, 1H), 7.75 (s, 1H), 7.86 (m, 2H), 8.00 (m, 1H), 8.43 (s, 1H), 11.60 (s, 1H), 13.25 (br, 2H)

Example C-13

2,3-Dihydro-benzo[1,4]dioxine-6-carboxylic acid[3-(5-ethyl-7,7-dimethyl-6-oxo-1,5,6,7-tetrahydro-imidazo[4,5-f]indol-2-yl)-1H-pyrazol-4-yl]-amide 2,3-Dihydro-benzo[1,4]dioxine-6-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2,3-dihydro-1,4-benzoxdioxine-6-carboxylic acid (159 mg, 0.89 mmol). The title compound was obtained as light yellow powder (159 mg, 41 mmol).

MS: M=473.1 (API+)

$^1$H-NMR (500 MHz, $D_6$-DMSO): δ (ppm)=1.21 (m, 3H), 1.34 (m, 6H), 3.79 (m, 2H), 4.36 (s, 4H), 7.04 and 7.30 (d, 1H, tautomeric forms), 7.19 (d, 1H), 7.46 and 7.70 (d, 1H, tautomeric forms), 7.58 (m, 2H), 8.34 (s, 1H), 11.39 (d, 1H), 13.20 (br, 2H)

Example C-14

5-Methyl-1H-pyrazole-3-carboxylic acid[3-(5-ethyl-7,7-dimethyl-6-oxo-1,5,6,7-tetrahydro-imidazo[4,5-f]indol-2-yl)-1H-pyrazol-4-yl]-amide 5-Methyl-1H-pyrazole-3-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 5-methyl-1H-pyrazole-3-carboxylic acid (111 mg, 0.89 mmol). The title compound was obtained as light brown powder (72 mg, 21%).

MS: M=419.1 (API+)

$^1$H-NMR (500 MHz, $D_6$-DMSO): δ (ppm)=1.21 (m, 3H), 1.34 (m, 6H), 2.33 (s, 3H), 3.79 (m, 2H), 6.53 (s, 1H), 7.03 and 7.18 (d, 1H, tautomeric forms), 7.45 and 7.58 (d, 1H, tautomeric forms), 8.38 (s, 1H), 11.16 (s, 1H), 13.10 (br, 2H)

Example C-15

1-Methyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide Methyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f indol-6-one (250 mg, 0.81 mmol) and 1-methylcyclopropanecarboxylic acid (88 mg, 0.89 mmol). The title compound was obtained as brown powder (60 mg, 18%).

MS: M=393.3 (ESI+)

$^1$H-NMR (500 MHz, $D_6$-DMSO): δ (ppm)=0.77 and 1.14 (s, 3H), 1.19 (m, 3H), 1.33 (m, 6H), 1.61 (s, 2H), 2.50 (s, 2H), 3.77 (m, 2H), 7.03 and 7.22 (d, 1H, tautomeric forms), 7.44 and 7.62 (d, 1H, tautomeric forms), 8.20 (s, 1H), 10.86 (s, 1H), 13.10 (br, 2H)

Example C-16

1-Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide Phenyl-cyclopropanecarboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 1-phenyl-1-cyclorpropanecarboxylic acid (143 mg, 0.89 mmol). The title compound was obtained as brown powder (61 mg, 15%).

MS: M=455.3 (ESI+)

$^1$H-NMR (500 MHz, $D_6$-DMSO): δ (ppm)=1.18 (m, 3H), 1.33 (m, 6H), 1.54 (s, 2H), 3.85 (m, 2H), 6.70 and 6.92 (d, 1H, tautomeric forms), 7.11 and 7.33 (d, 1H, tautomeric forms), 7.56 (m, 5H), 8.24 (m, 1H), 10.34 (s, 1H), 12.81 (s, 1H), 13.09 (d, 1H)

Example C-17

3,5-Diethoxy-N-[3-(5-ethyl-7,7-dimethyl-6-oxo-1,5,6,7-tetrahydro-imidazo[4,5-f]indol-2-yl)-1H-pyrazol-4-yl]-benzamide 3,5-Diethoxy-N-[3-(5-ethyl-7,7-dimethyl-6-oxo-1,5,6,7-tetrahydro-imidazo[4,5-f]indol-2-yl)-1H-pyrazol-4-yl]-benzamide was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 3,5-diethoxybenzoic acid (186 mg, 0.89 mmol). The title compound was obtained as brown powder (99 mg, 24%).

MS: M=503.3 (ESI+)

$^1$H-NMR (500 MHz, $D_6$-DMSO): δ (ppm)=1.22 (m, 3H), 1.33 (s, 6H), 1.40 (m, 6H), 3.79 (m, 2H), 4.17 (m, 4H), 6.76 (s, 1H), 7.16 (m, 3H), 7.52 (d, 1H), 8.34 (m, 1H), 11.58 (s, 1H), 13.24 (m, 1H)

Example C-18

N-[3-(5-Ethyl-7,7-dimethyl-6-oxo-1,5,6,7-tetrahydro-imidazo[4,5-f]indol-2-yl)-1H-pyrazol-4-yl]-3,5-dimethoxy-benzamide N-[3-(5-Ethyl-7,7-dimethyl-6-oxo-1,5,6,7-tetrahydro-imidazo[4,5-f]indol-2-yl)-1H-pyrazol-4-yl]-3,5-dimethoxy-benzamide was prepared using 2-(4-amino-1H-pyrazol-3-yl)-5-ethyl-7,7-dimethyl-5,7-dihydro-1H-imidazo[4,5-f]indol-6-one (250 mg, 0.80 mmol) and 3,5-dimethoxy benzoic acid (161 mg, 0.87 mmol). The title compound was obtained as powder (62 mg, 16%).

MS: M=475.3 (ESI+)

$^1$H-NMR (500 MHz, $D_6$-DMSO): δ (ppm)=1.20 (m, 3H), 1.33 (s, 6H), 3.79 (m, 2H), 3.92 (s, 6H), 6.79 (s, 1H), 7.04 (s, 1H), 7.16 (s, 1H), 7.20 (s, 1H), 7.50 (d, 1H), 8.36 (s, 1H), 11.52 (d, 1H), 13.22 (m, 2H)

Example C-19

1-Methyl-cyclopropanecarboxylic acid[3-(5-isopropyl-7,7-dimethyl-6-oxo-3,5,6,7-tetrahydro-imidazo[4,5-f]indol-2-yl)-1H-pyrazol-4-yl]-amide Methyl-cyclopropanecarboxylic acid[3-(5-isopropyl-7,7-dimethyl-6-oxo-3,5,6,7-tetrahydro-imidazo[4,5-f]indol-2-yl)-1H-pyrazol-4-yl]-amide was prepared using 2-(4-amino-1H-pyrazol-3-yl)-5-isopropyl-7,7-dimethyl-5,7-dihydro-3H-imidazo[4,5-f]indol-6-one (300 mg. 0.925 mmol) and 1-methyl-cyclopropanecarboxylic acid (101.8 mg, 1.017 mmol). 210 mg (56%) of the title compound were obtained.

MS: M=407.4 (ESI+)

$^1$H-NMR (400 MHz, DMSO): δ (ppm)=0.76 (d, 2H), 1.12 (d, 2H), 1.30 (s, 6H), 1.45 (d, 6H), 1.61 (s, 3H), 3.39 (m, 4H), 4.56 (m, 1H), 7.12 and 7.28 (s, 1H, two tautomeric forms), 7.42 and 7.61 (s, 1H, two tautomeric forms), 8.20 (s, 1H), 10.83 and 10.83 (br, 1H, two tautomeric forms), 12.95 (br, 1H), 13.10 (br, 1H)

Example C-20

1-Methyl-cyclopropanecarboxylic acid[3-(7,7-diethyl-5-isopropyl-6-oxo-1,5,6,7-tetrahydro-imidazo[4,5-f]indol-2-yl)-1H-pyrazol-4-yl]-amide Methyl-cyclopropanecarboxylic acid[3-(7,7-diethyl-5-isopropyl-6-oxo-1,5,6,7-tetrahydro-imidazo[4,5-f]indol-2- yl)-1H-pyrazol-4-yl]-amide was prepared using 2-(4-Amino-1H-pyrazol-3-yl)-7,7-diethyl-5-isopropyl-5,7-dihydro-1H-imidazo[4,5-f]indol-6-one (150 mg, 0.43 mmol) and 1-methyl-cyclopropane-carboxylic acid (51 mg, 0.43 mmol). 17 mg (9%) %) of the title compound were obtained.

MS: M=435.3 (ESI+)

$^1$H-NMR (400 MHz, DMSO): δ (ppm)=0.45 (t, 6H), 0.76 (m, 2H), 1.15 (m, 2H), 1.45 (d, 6H), 1.61 (m, 3H), 1.85 (q, 4H), 4.58 (m, 1H), 7.11 and 7.29 (s, 1H, two tautomeric forms), 7.31 and 7.51 (s, 1H, two tautomeric forms), 8.21 (s, 1H), 10.86 and 10.92 (br, 1H, two tautomeric forms), 12.95 and 13.04 (br, 1H, two tautomeric forms), 13.10 and 13.15 (br, 1H, two tautomeric forms)

Example D

General Procedure D

A solution of appropriate aminopyrazole (0.48 mmol), triethylamine (0.10 ml, 0.72 mmol) and an appropriate isocyanate (0.41 mmol) in DMF (3.0 ml) was refluxed under argon atmosphere for 3 hours. The mixture was stirred at room temperature overnight. Ethyl acetate (30 ml) and water (30 ml) were added. The aqueous layer was extracted three times with 50 ml ethyl acetate. The combined organic layers were washed with brine, dried ($Na_2SO_4$) and evaporated to afford a residue purified by flash chromatography.

Example D-1

1-Benzyl-3-[3-(5-ethyl-7,7-dimethyl-6-oxo-1,5,6,7-tetrahydro-imidazo[4,5-f]indol-2-yl)-1H-pyrazol-4-yl]-urea Benzyl-3-[3-(5-ethyl-7,7-dimethyl-6-oxo-1,5,6,7-tetrahydro-imidazo[4,5-f]indol-2-yl)-1H-pyrazol-4-yl]-urea was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and benzylisocyanate (0.05 ml, 0.41 mmol). After purification by flash chromatography (dichloromethane/methanol 94:6) the title compound was obtained as a light grey powder (26 mg).

MS: M=444.0 (API+)

$^1$H-NMR (400 MHz. D$_6$-DMSO): δ (ppm)=1.19 (t, 3H), 1.32 (s, 6H), 3.75 (m, 2H), 4.33 (m, 2H), 7.00 and 7.19 (s, 1H, tautomeric forms), 7.24 (br, 1H), 7.31 (br, 4H), 7.42 and 7.57 (s, 1H, tautomeric forms), 7.85 (s, 1H), 8.05 (s, 1H), 9.16 (m, 1H), 12.85 (br, 1H), 12.92 (br, 1H)

Example E

General Procedure E

To a solution of appropriate amino pyrazole (0.48 mmol) in THF (20 ml), appropriate chloroformate or carbamoyl chloride (0.97 mmol) and diisopropyl-ethyl-amine (DIPEA) (0.25 ml, 1.43 mmol) were slowly added at room temperature and stirred overnight. Aqueous ammonia (0.5 ml) was added to quench the reaction and the solvent was evaporated. The residue was purified either by flash chromatography (dichloromethane/methanol) or HPLC.

The following compounds were made using general procedure D:

Example E-1

Morpholine-4-carboxylic acid[3-(5-ethyl-7,7-dimethyl-6-oxo-1,5,6,7-tetrahydro-imidazo[4,5-f]indol-2-yl)-1H-pyrazol-4-yl]-amide Morpholine-4-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (100 mg, 0.32 mmol) and morpholine 4-carbonyl chloride. The title compound was obtained as light yellow powder (51 mg).

MS: M=424.0 (API+)

$^1$H-NMR (400 MHz, D$_6$-DMSO): δ (ppm)=1.19 (t, 3H), 1.32 (s, 6H), 3.51 (m, 4H), 3.72 (m, 4H), 3.75 (m, 2H), 7.00 and 7.28 (s, 1H, tautomeric forms), 7.42 and 7.67 (s, 1H, tautomeric forms), 8.04 (s, 1H), 9.98 (s, 1H), 13.00 (br, 2H)

Example E-2

Piperidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide Piperidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and 1-piperidinecarbonyl chloride. The title compound was obtained as light brown powder (101 mg).

MS: M=422.1 (API+)

$^1$H-NMR (400 MHz. D$_6$-DMSO): δ (ppm)=1.18 (t, 3H), 1.32 (s, 6H), 1.61 (m, 6H), 3.52 (m, 4H), 3.77 (m, 2H), 7.00 and 7.22 (s, 1H, tautomeric forms), 7.41 and 7.62 (s, 1H, tautomeric forms), 8.01 (s, 1H), 9.95 (m, 1H), 13.00 (m, 2H)

Example E-3

4-Methyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide 4-Methyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]indol-6-one (150 mg, 0.48 mmol) and 4-methyl-1-piperazinecarbonyl chloride. The title compound was obtained as light yellow powder (50 mg).

MS: M=437.1 (API+)

$^1$H-NMR (400 MHz, D$_6$-DMSO): δ (ppm)=1.19 (t, 3H), 1.33 (s, 6H), 2.24 (s, 3H), 2.42 (br, 4H), 3.53 (br, 4H), 3.77 (q, 2H), 7.05 (br, 1H), 7.60 (br, 1H), 8.01 (s, 1H), 10.01 (s, 1H), 13.10 (br, 2H)

Example E-4

3-(7,7-Dimethyl-6-oxo-1,5,6,7-tetrahydro-imidazo[4,5-f]indol-2-yl)-1H-pyrazol-4-yl]-carbamic acid benzyl ester 3-(7,7-Dimethyl-6-oxo-1,5,6,7-tetrahydro-imidazo[4,5-f]indol-2-yl)-1H-pyrazol-4-yl]-carbamic acid benzyl ester was prepared using 2-(4-amino-1H-pyrazol-3-yl)-7,7-dimethyl- 5,7-dihydro-1H-imidazo[4,5-f]indol-6-one (100 mg, 0.35 mmol) and benzyl chloroformate.

The title compound was obtained as white powder (71 mg).

MS: M=417.1 (API+)

$^1$H-NMR (400 MHz, D$_6$-DMSO): δ (ppm)=1.29 (s, 6H), 5.22 (s, 2H), 6.91 and 7.05 (br, 1H), 7.36-7.47 (m, 5H), 7.64 (s, 1H), 8.02 (s, 1H), 9.63 (s, 1H), 10.31 (s, 1H), 12.70 and 13.10 (br, 2H)

Example E-5

[3-(5-Ethyl-7,7-dimethyl-6-oxo-1,5,6,7-tetrahydro-imidazo[4,5-f]indol-2-yl)-1H-pyrazol-4-yl]-carbamic acid benzyl ester

[3-(5-Ethyl-7,7-dimethyl-6-oxo-1,5,6,7-tetrahydro-imidazo[4,5-f]indol-2-yl)-1H-pyrazol-4-yl]-carbamic acid benzyl ester was prepared using 2-(4-amino-1H-pyrazol-3-yl)-5-ethyl-7,7-dimethyl-5,7-dihydro-1H-imidazo[4,5-f]indol-6-one (300 mg, 0.96 mmol) and benzyl chloroformate (414 μl, 2.90 mmol). The title compound was obtained as yellow powder (8 mg, 2%).

MS: M=445.4 (ESI+)

$^1$H-NMR (400 MHz, D$_6$-DMSO): δ (ppm)=1.59 (m, 3H), 1.72 (s, 6H), 4.17 (m, 2H), 5.64 (s, 2H), 7.84 (m, 7H), 8.46 (s, 1H), 10.06 (s, 1H), 13.50 (br, 2H)

Example E-6

[3-(5-Ethyl-7,7-dimethyl-6-oxo-1,5,6,7-tetrahydro-imidazo[4,5-f]indol-2-yl)-1H-pyrazol-4-yl]-carbamic acid methyl ester

[3-(5-Ethyl-7,7-dimethyl-6-oxo-1,5,6,7-tetrahydro-imidazo[4,5-f]indol-2-yl)-1H-pyrazol-4-yl]-carbamic acid methyl ester was prepared using 2-(4-amino-1H-pyrazol-3-yl)-5-ethyl-7,7-dimethyl-5,7-dihydro-1H-imidazo[4,5-f]indol-6-one (300 mg, 0.96 mmol) and methylchloroformate (89 μl, 1.16 mmol). The title compound was obtained as white powder (200 mg, 56%).

MS: M=369.2 (ESI+)

$^1$H-NMR (400 MHz, D$_6$-DMSO): δ (ppm)=1.91 (m, 3H), 1.31 (s, 6H), 3.75 (m, 5H), 7.51 (br, 2H), 8.01 (s, 1H), 9.66 (s, 1H), 13.09 (br, 1H)

Example E-7

[3-(5-Ethyl-7,7-dimethyl-6-oxo-1,5,6,7-tetrahydro-imidazo[4,5-f]indol-2-yl)-1H-pyrazol-4-yl]-carbamic acid phenyl ester

[3-(5-Ethyl-7,7-dimethyl-6-oxo-1,5,6,7-tetrahydro-imidazo[4,5-f]indol-2-yl)-1H-pyrazol-4-yl]-carbamic acid phenyl ester was prepared using 2-(4-amino-1H-pyrazol-3-yl)-5-ethyl-7,7-dimethyl-5,7-dihydro-1H-imidazo[4,5-f]indol-6-one (300 mg, 0.96 mmol) and phenylchloroformate (146 μl, 1.16 mmol). The title compound was obtained as brown powder (55 mg, 13%).

MS: M=431.3 (ESI+)

$^1$H-NMR (400 MHz, D$_6$-DMSO): δ (ppm)=1.26 (m, 3H), 1.37 (s, 6H), 3.83 (m, 2H), 6.77 (m, 3H), 7.16 (m, 2H), 7.43 and 7.80 (d, 1H, tautomeric forms), 7.73 (s, 1H), 7.97 and 8.32 (d, 1H, tautomeric forms), 9.10 (s, 1H), 11.57 (br, 1H), 13.81 (br, 1H)

Example E-8

1,1-Diethyl-3-[3-(5-ethyl-7,7-dimethyl-6-oxo-1,5,6,7-tetrahydro-imidazo[4,5-f]indol-2-yl)-1H-pyrazol-4-yl]-urea 1,1-Diethyl-3-[3-(5-ethyl-7,7-dimethyl-6-oxo-1,5,6,7-tetrahydro-imidazo[4,5-f]indol-2-yl)-1H-pyrazol-4-yl was prepared using 2-(4-amino-1H-pyrazol-3-yl)-5-ethyl-7,7-dimethyl-5,7-dihydro-1H-imidazo[4,5-f]indol-6-one (300 mg, 0.97 mmol) and diethylcarbamoyl chloride (134 μl, 1.06 mmol). The title compound was obtained as yellow powder (85 mg, 21%).

MS: M=410.3 (ESI+)

$^1$H-NMR (400 MHz D$_6$-DMSO): δ (ppm)=1.21 (m, 9H), 1.32 (m, 6H), 3.44 (m, 4H), 3.76 (m, 2H), 7.01 and 7.16 (d, 1H, tautomeric forms), 7.41 and 7.56 (d, 1H, tautomeric forms), 8.00 (s, 1H), 9.87 (d, 1H), 12.96 (s, 2H)

Example E-9

[3-(5-Ethyl-7,7-dimethyl-6-oxo-1,5,6,7-tetrahydro-imidazo[4,5-f]indol-2-yl)-1H-pyrazol-4-yl]-carbamic acid ethyl ester

[3-(5-Ethyl-7,7-dimethyl-6-oxo-1,5,6,7-tetrahydro-imidazo[4,5-f]indol-2-yl)-1H-pyrazol-4-yl]-carbamic acid ethyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and ethyl chloroformate (84 μl, 0.89 mmol). The title compound was obtained as brown powder (100 mg, 32%).

MS: M=383.4 (ESI+)

$^1$H-NMR (400 MHz, D$_6$-DMSO): δ (ppm)=1.21 (m, 3H), 1.32 (m, 9H), 3.77 (m, 2H), 4.19 (m, 2H), 7.00 and 7.38 (d, 1H, tautomeric forms), 7.41 and 7.74 (d, 1H, tautomeric forms), 8.01 (s, 1H), 9.57 (s, 1H), 13.00 (d, 1H), 13.17 (d, 1H)

Example E-10

3-[3-(5-Ethyl-7,7-dimethyl-6-oxo-1,5,6,7-tetrahydro-imidazo[4,5-f]indol-2-yl)-1H-pyrazol-4-yl]-1,1-dimethyl-urea 3-[3-(5-Ethyl-7,7-dimethyl-6-oxo-1,5,6,7-tetrahydro-imidazo[4,5-f]indol-2-yl)-1H-pyrazol-4-yl]-1,1-dimethyl-urea was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and N,N-dimethylcarbamoyl chloride (81 μl, 0.88 mmol). The title compound was obtained as brown powder (39 mg, 12%).

MS: M=382.3 (ESI+)

$^1$H-NMR (400 MHz, D$_6$-DMSO): δ (ppm)=1.19 (m, 3H), 1.31 (s, 6H), 3.06 (s, 6H), 3.75 (m, 2H), 7.00 and 7.25 (d, 1H, tautomeric forms), 7.41 and 7.63 (d, 1H, tautomeric forms), 8.01 (s, 1H), 9.84 (s, 1H), 12.96 (br, 2H)

Example E-11

Pyrrolidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide Pyrrolidine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-5-ethyl-7,7-dimethyl-5,7-dihydro-1H-imidazo[4,5-f]

indol-6-one (140 mg, 0.45 mmol) and 1-pyrolidine carbonyl chloride (154 µl, 1.40 mmol). The title compound was obtained as light grey powder (50 mg, 275).

MS: M=408.2 (ESI+)

$^1$H-NMR (400 MHz, D$_6$-DMSO): δ (ppm)=1.21 (m, 3H), 1.25 (m, 6H), 1.32 (s, 6H), 1.96 (s, 4H), 3.46 (s, 4H), 3.75 (m, 2H), 7.00 and 7.24 (d, 1H, tautomeric forms), 7.41 and 7.63 (d, 1H, tautomeric forms), 8.01 (s, 1H), 9.54 (s, 1H), 12.96 (br, 2H)

Example E-12

[3-(5-Ethyl-7,7-dimethyl-6-oxo-1,5,6,7-tetrahydro-imidazo[4,5-f]indol-2-yl)-1H-pyrazol-4-yl]-carbamic acid 2,2-dimethyl-propyl ester

[3-(5-Ethyl-7,7-dimethyl-6-oxo-1,5,6,7-tetrahydro-imidazo[4,5-f]indol-2-yl)-1H-pyrazol-4-yl]-carbamic acid 2,2-dimethyl-propyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2,2-dimethylpropyl chloroformate (131 µl, 0.89 mmol). The title compound was obtained as yellow powder (245 mg, 71%).

MS: M=425.2 (ESI+)

$^1$H-NMR (400 MHz, D$_6$-DMSO): δ (ppm)=1.04 (s, 9H), 1.19 (m, 3H), 1.32 (s, 6H), 3.78 (m, 2H), 3.90 (s, 2H), 7.00 and 7.37 (d, 1H, tautomeric forms), 7.44 and 7.72 (d, 1H, tautomeric forms), 8.02 (s, 1H), 9.50 (s, 1H), 13.08 (br, 2H)

Example E-13

[3-(5-Ethyl-7,7-dimethyl-6-oxo-1,5,6,7-tetrahydro-imidazo[4,5-f]indol-2-yl)-1H-pyrazol-4-yl]-carbamic acid 2-chloro-benzyl ester

[3-(5-Ethyl-7,7-dimethyl-6-oxo-1,5,6,7-tetrahydro-imidazo[4,5-f]indol-2-yl)-1H-pyrazol-4-yl]-carbamic acid 2-chloro-benzyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-chlorobenzyl chloroformate (135 µl, 0.89 mmol). The title compound was obtained as yellow powder (227 mg, 58%).

MS: M=479.3 (ESI+)

$^1$H-NMR (400 MHz D$_6$-DMSO): δ (ppm)=1.17 (m, 3H), 1.30 (s, 6H), 3.74 (m, 2H), 5.32 (s, 2H), 7.00 and 7.36 (d, 1H, tautomeric forms), 7.43 (m, 4H), 7.53 (m, 1H), 7.61 and 7.73 (d, 1H, tautomeric forms), 8.04 (s, 1H), 9.66 (s, 1H), 13.00 (br, 1H), 13.19 (br, 1H)

Example E-14

[3-(5-Ethyl-7,7-dimethyl-6-oxo-1,5,6,7-tetrahydro-imidazo[4,5-f]indol-2-yl)-1H-pyrazol-4-yl]-carbamic acid isobutyl ester

[3-(5-Ethyl-7,7-dimethyl-6-oxo-1,5,6,7-tetrahydro-imidazo[4,5-f]indol-2-yl)-1H-pyrazol-4-yl]-carbamic acid isobutyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and isobutyl chloroformate (115 µl, 0.89 mmol). The title compound was obtained as brown solid (85 mg, 25%).

MS: M=411.3 (ESI+)

$^1$H-NMR (400 MHz, D$_6$-DMSO): δ (ppm)=0.95 (d, 6H), 1.19 (m, 3H), 1.32 (s, 6H), 1.99 (m, 1H), 3.78 (m, 2H), 3.95 (m, 2H), 7.02 and 7.41 (d, 1H, tautomeric forms), 7.45 and 7.72 (d, 1H, tautomeric forms), 8.02 (s, 1H), 9.52 (s, 1H), 13.08 (br, 2H)

Example E-15

[3-(5-Ethyl-7,7-dimethyl-6-oxo-1,5,6,7-tetrahydro-imidazo[4,5-f]indol-2-yl)-1H-pyrazol-4-yl]-carbamic acid 2-methoxy-ethyl ester

[3-(5-Ethyl-7,7-dimethyl-6-oxo-1,5,6,7-tetrahydro-imidazo[4,5-f]indol-2-yl)-1H-pyrazol-4-yl]-carbamic acid 2-methoxy-ethyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and 2-methoxy-ethyl chloroformate (103 µl, 0.89 mmol). The title compound was obtained as yellow powder (196 mg, 59%).

MS: M=413.3 (ESI+)

$^1$H-NMR (400 MHz, D$_6$-DMSO): δ (ppm)=1.19 (m, 3H), 1.31 (s, 6H), 3.33 (s, 3H), 3.61 (m, 2H), 3.76 (m, 2H), 4.28 (m, 2H), 7.00 and 7.41 (d, 1H, tautomeric forms), 7.43 and 7.78 (d, 1H, tautomeric forms), 8.02 (s, 1H), 9.59 (s, 1H), 13.08 (br, 2H)

Example E-16

[3-(5-Ethyl-7,7-dimethyl-6-oxo-1,5,6,7-tetrahydro-imidazo[4,5-f]indol-2-yl)-1H-pyrazol-4-yl]-carbamic acid cyclopentyl ester

[3-(5-Ethyl-7,7-dimethyl-6-oxo-1,5,6,7-tetrahydro-imidazo[4,5-f]indol-2-yl)-1H-pyrazol-4-yl]-carbamic acid cyclopentyl ester was prepared using 2-(4-amino-1H-pyrazol-3-yl)-5-ethyl-7,7-dimethyl-5,7-dihydro-1H-imidazo[4,5-f]indol-6-one (250 mg, 0.81 mmol) and cyclopentyl chloroformate (126 µl, 0.97 mmol). The title compound was obtained as yellow powder (116 mg, 34%).

MS: M=423.2 (API+)

$^1$H-NMR (400 MHz, D$_6$-DMSO): δ (ppm)=1.17 (m, 3H), 1.32 (s, 6H), 1.60 (m, 2H), 1.74 (m, 2H), 1.91 (m, 2H), 3.74 (m, 2H), 5.15 (s, 1H), 7.00 and 7.41 (d, 1H, tautomeric forms), 7.43 and 7.78 (d, 1H, tautomeric forms), 8.02 (s, 1H), 9.40 (s, 1H), 13.07 (br, 2H)

Example E-17

3-[3-(5-Ethyl-7,7-dimethyl-6-oxo-1,5,6,7-tetrahydro-imidazo[4,5-f]indol-2-yl)-1H-pyrazol-4-yl]-1,1-di-isopropyl-urea 3-[3-(5-Ethyl-7,7-dimethyl-6-oxo-1,5,6,7-tetrahydro-imidazo[4,5-f]indol-2-yl)-1H-pyrazol-4-yl]-1,1-diisopropyl-urea was prepared using 2-(4-amino-1H-pyrazol-3-yl)-5-ethyl-7,7-dimethyl-5,7-dihydro-1H-imidazo[4,5-f]indol-6-one (300 mg, 0.97 mmol) and diisopropyl carbamyl chloride (158 mg, 0.97 mmol). The title compound was obtained as yellow powder (55 mg, 12%).

MS: M=438.4 (ESI+)

$^1$H-NMR (400 MHz, D$_6$-DMSO): δ (ppm)=1.21 (m, 3H), 1.32 (s, 6H), 1.38 (m, 12H), 3.77 (m, 2H), 4.08 (m, 2H), 7.05 (d, 1H), 7.49 (d, 1H), 8.03 (s, 1H), 9.63 (d, 1H), 12.93 (br, 2H)

Example E-18

[3-(5-Isopropyl-7,7-dimethyl-6-oxo-1,5,6,7-tetrahydro-imidazo[4,5-f]indol-2-yl)-1H-pyrazol-4-yl]-carbamic acid methyl ester

[3-(5-Isopropyl-7,7-dimethyl-6-oxo-1,5,6,7-tetrahydro-imidazo[4,5-f]indol-2-yl)-1H-pyrazol-4-yl]-carbamic acid methyl ester was prepared using 2-(4-amino-1H-pyrazol-3-yl)-5-isopropyl-7,7-dimethyl-5,7-dihydro-1H-imidazo[4,5-f]indol-6-one (325 mg, 0.90 mmol) and methyl chloroformiate (78 µl, 0.99 mmol). The title compound was obtained as light yellow powder (88 mg, 24%).

MS: M=383.1 (ESI+)

$^1$H-NMR (400 MHz, D$_6$-DMSO): δ (ppm)=1.29 (s, 6H), 1.45 (s, 6H), 3.74 (s, 3H), 4.57 (m, 1H), 7.09 and 7.39 (d, 1H, tautomeric forms), 7.43 and 7.71 (d, 1H, tautomeric forms), 8.00 (s, 1H), 9.62 (s, 1H), 12.93 (d, 1H), 13.15 (d, 1H)

Example E-19

Piperidine-1-carboxylic acid[3-(5-isopropyl-7,7-dimethyl-6-oxo-3,5,6,7-tetrahydro-imidazo[4,5-f]indol-2-yl)-1H-pyrazol-4-yl]-amide Piperidine-1-carboxylic acid[3-(5-isopropyl-7,7-dimethyl-6-oxo-3,5,6,7-tetrahydro-imidazo[4,5-f]indol-2-yl)-1H-pyrazol-4-yl]-amide was prepared using 2-(4-amino-1H-pyrazol-3-yl)-5-isopropyl-7,7-dimethyl-5,7-dihydro-3H-imidazo[4,5-f]indol-6-one (200 mg, 0.247 mmol) and piperidine-1-carbonyl chloride (40.0 mg, 0.271 mmol). 40 mg (37%) % of the title compound were obtained.

MS: M=436.4 (ESI+)

$^1$H-NMR (400 MHz, DMSO): δ (ppm)=1.30 (d, 6H), 1.46 (s, 6H), 1.60 (m, 6H), 3.39 (m, 4H), 4.56 (m, 1H), 7.10 and 7.28 (s, 1H, two tautomeric forms), 7.40 and 7.60 (s, 1H, two tautomeric forms), 8.01 (s, 1H), 9.93 and 9.99 (br, 1H, two tautomeric forms), 12.85 (br, 1H), 12.95 and 13.00 (br, 1H two tautomeric forms)

Example E-20

Piperidine-1-carboxylic acid[3-(7,7-diethyl-5-isopropyl-6-oxo-1,5,6,7-tetrahydro-imidazo[4,5-f]indol-2-yl)-1H-pyrazol-4-yl]-amide Piperidine-1-carboxylic acid[3-(7,7-diethyl-5-isopropyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-7,7-diethyl-5-isopropyl-5,7-dihydro-1H-imidazo[4,5-f]indol-6-one (150 mg, 0.43 mmol) and piperidine-1-carbonyl chloride (63 mg, 0.43 mmol). 30 mg (15%) of the title compound were obtained.

MS: M=464.4 (ESI+)

$^1$H-NMR (400 MHz, DMSO): δ (ppm)=0.45 (t, 6H), 1.45 (d, 6H), 1.61 (m, 6H), 1.78 (m, 4H), 3.52 (m, 4H), 4.56 (m, 1H), 7.09 and 7.28 (s, 1H, two tautomeric forms), 7.29 and 7.51 (s, 1H, two tautomeric forms), 8.01 (s, 1H), 9.92 and 10.00 (br, 1H, two tautomeric forms), 12.88 (br, 1H), 12.95 and 13.00 (br, 1H, two tautomeric forms)

Example E-21

3-[3-(7,7-Diethyl-5-isopropyl-6-oxo-1,5,6,7-tetrahydro-imidazo[4,5-f]indol-2-yl)-1H-pyrazol-4-yl]-1,1-diethyl-urea 3-[3-(7,7-Diethyl-5-isopropyl-6-oxo-1,5,6,7-tetrahydro-imidazo[4,5-f]indol-2-yl)-1H-pyrazol-4-yl]-1,1-diethyl-urea was prepared using 2-(4-amino-1H-pyrazol-3-yl)-7,7-diethyl-5-isopropyl-5,7-dihydro-1H-imidazo[4,5-f]indol-6-one (150 mg, 0.43 mmol) and diethylcarbamoyl chloride (58 mg, 0.43 mmol). 12 mg (6%) % of the title compound were obtained.

MS: M=452.3 (ESI+)

$^1$H-NMR (400 MHz, DMSO): δ (ppm)=0.46 (t, 6H), 1.25 (m, 6H), 1.46 (d, 6H), 1.81 (m, 4H), 3.44 (m, 4H), 4.56 (m, 1H), 7.11 and 7.23 (s, 1H, two tautomeric forms), 7.30 and 7.45 (s, 1H, two tautomeric forms), 8.01 (s, 1H), 9.86 and 9.96 (br, 1H, two tautomeric forms), 12.87 and 12.94 (br, 1H, two tautomeric forms), 12.94 and 12.98 (br, 1H, two tautomeric forms)

Example E-22

[3-(5-Ethyl-7,7-dimethyl-6-oxo-1,5,6,7-tetrahydro-imidazo[4,5-f]indol-2-yl)-1H-pyrazol-4-yl]-carbamic acid isopropyl ester

[3-(5-Ethyl-7,7-dimethyl-6-oxo-1,5,6,7-tetrahydro-imidazo[4,5-f]indol-2-yl)-1H-pyrazol-4-yl]-carbamic acid isopropyl ester was prepared using 2-(4-amino-1H-pyrazol-3-yl)-5-ethyl-7,7-dimethyl-5,7-dihydro-1H-imidazo[4,5-f]indol-6-one (250 mg, 0.805 mmol) and isopropyl chloroformate (886 mg, 0.886 mmol). 136 mg (43%) of the title compound were obtained.

MS: M=397.3 (ESI+)

$^1$H-NMR (400 MHz, DMSO): δ (ppm)=1.06 (t, 3H), 1.30 (m, 12H), 3.77 (q, 2H), 4.95 (m, 1H), 7.00 and 7.37 (s, 1H, two tautomeric forms), 7.40 and 7.75 (s, 1H, two tautomeric forms), 8.02 (s, 1H), 9.45 (br, 1H), 13.00 (br, 1H), 13.15 (br, 1H)

Example F

General Procedure F

A solution of appropriate aminopyrazole (0.32 mmol), 1,1'-carbonyl-diimidazole (CDI) (250 mg, 1.55 mmol) was refluxed in THF (10 ml) under argon atmosphere for 20 hours. The mixture was cooled to room temperature and a solution of appropriate amine or alcohol (1.61 mmol) in THF (1.5 ml) was slowly added. The mixture was refluxed overnight. It was cooled to ambient temperature and ethyl acetate (30 ml) and water (30 ml) were added. The aqueous layer was extracted three times with 50 ml ethyl acetate. The combined organic layers were washed with brine, dried (Na$_2$SO$_4$) and evaporated to afford a residue purified either by flash chromatography or by high performance liquid chromatography (HPLC).

Example F-1

4-Acetyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide 4-Acetyl-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-Amino-1H-pyrazol-3-yl)-5-ethyl-7,7-dimethyl-5,7-dihydro-1H-imidazo[4,5-f]indol-6-one (100 mg, 0.32 mmol) and 1-acetyl-piperazine (206 mg, 1.61 mmol). After purification by flash chromatography (dichloromethane/methanol 95:5) followed by preparative high performance liquid chromatography (HPLC) the title compound was obtained as a white powder (36 mg).

MS: M=463.0 (API−)

¹H-NMR (400 MHz, D₆-DMSO): δ (ppm)=1.20 (t, 3H), 1.33 (s, 6H), 2.07 (s, 3H), 3.44 (m, 2H), 3.52-3.62 (m, 6H), 3.78 (m, 2H), 7.04 and 7.30 (s, 1H, tautomeric forms), 7.40 and 7.80 (s, 1H, tautomeric forms), 8.03 (s, 1H), 10.00 (m, 1H), 13.00 (br, 2H)

Example F-2

3-Oxo-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide 3-Oxo-piperazine-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-Amino-1H-pyrazol-3-yl)-5-ethyl-7,7-dimethyl-5,7-dihydro-1H-imidazo[4,5-f]indol-6-one (300 mg, 0.96 mmol) and piperazin-2-one (193 mg, 1.93 mmol). The title compound was obtained as light yellow powder (52 mg, 12%).

MS: M=437.3 (ESI+)

¹H-NMR (500 MHz, D₆-DMSO): δ (ppm)=1.20 (m, 3H), 1.32 (s, 6H), 3.70 (m, 2H), 3.74 (m, 2H), 4.08 (s, 2H), 6.92 and 7.10 (d, 1H, tautomeric forms), 7.12 and 7.60 (d, 1H, tautomeric forms), 8.02 (s, 1H), 8.18 (s, 1H), 9.95 (s, 1H), 13.03 (br, 2H)

Example F-3

1-Benzyl-3-[3-(5-ethyl-7,7-dimethyl-6-oxo-1,5,6,7-tetrahydro-imidazo[4,5-f]indol-2-yl)-1H-pyrazol-4-yl]-1-isopropyl-urea Benzyl-3-[3-(5-ethyl-7,7-dimethyl-6-oxo-1,5,6,7-tetrahydro-imidazo[4,5-f]indol-2-yl)-1H-pyrazol-4-yl]-1-isopropyl-urea was prepared using 2-(4-Amino-1H-pyrazol-3-yl)-5-ethyl-7,7-dimethyl-5,7-dihydro-1H-imidazo[4,5-f]indol-6-one (400 mg, 1.29 mmol) and N-benzylisopropylamine (385 mg, 2,58 mmol). The title compound was obtained as off-white powder (13 mg, 2%).

MS: M=486.3 (API+)

¹H-NMR (500 MHz, D₆-DMSO): δ (ppm)=1.29 (m, 15H), 3.71 (m, 1H), 6.46 and 6.69 (d, 1H, tautomeric forms), 6.91 and 7.11 (d, 1H, tautomeric forms), 7.33 (m, 6H), 8.26 (br, 1H), 10.04 (br, 1H), 11.09 (br, 1H)

Example F-4

1-(2-Dimethylamino-ethyl)-1-ethyl-3-[3-(5-ethyl-7,7-dimethyl-6-oxo-1,5,6,7-tetrahydro-imidazo[4,5-f]indol-2-yl)-1H-pyrazol-4-yl]-urea 1-(2-Dimethylamino-ethyl)-1-ethyl-3-[3-(5-ethyl-7,7-dimethyl-6-oxo-1,5,6,7-tetrahydro-imidazo[4,5-f]indol-2-yl)-1H-pyrazol-4-yl]-urea was prepared using 2-(4-Amino-1H-pyrazol-3-yl)-5-ethyl-7,7-dimethyl-5,7-dihydro-1H-imidazo[4,5-f]indol-6-one (400 mg, 1.29 mmol) and N,N-dimethyl-N'-ethylethylendiamin (300 mg, 2.58 mmol). The title compound was obtained as off-white powder (65 mg, 11%).

MS: M=453.2 (API+)

¹H-NMR (500 MHz D₆-DMSO): δ (ppm)=1.19 (m, 3H), 1.21 (m, 3H), 1.32 (s, 6H), 1.90 (s, 2H), 2.22 (s, 6H), 3.47 (m, 4H), 3.77 (m, 2H), 7.01 and 7.18 (d, 1H, tautomeric forms), 7.42 and 7.56 (d, 1H, tautomeric forms), 8.01 (s, 1H), 9.93 (d, 1H), 12.99 (br, 2H)

Example F-5

Azepane-1-carboxylic acid[3-(5-ethyl-7,7-dimethyl-6-oxo-1,5,6,7-tetrahydro-imidazo[4,5-f]indol-2-yl)-1H-pyrazol-4-yl]-amide Azepane-1-carboxylic acid[3-(5-ethyl-7,7-dimethyl-6-oxo-1,5,6,7-tetrahydro-imidazo[4,5-f]indol-2-yl)-1H-pyrazol-4-yl]-amide was prepared using 2-(4-Amino-1H-pyrazol-3-yl)-5-ethyl-7,7-dimethyl-5,7-dihydro-1H-imidazo[4,5-f]indol-6-one (400 mg, 1.29 mmol) and hexamethylenimin (256 mg, 2.58 mmol). The title compound was obtained as off-white powder (110 mg, 20%).

MS: M=436.3 (ESI+)

¹H-NMR (500 MHz, D₆-DMSO): δ (ppm)=1.19 (m, 3H), 1.32 (s, 6H), 1.54 (m, 4H), 1.81 (m, 4H), 3.56 (br, 4H), 3.77 (m, 2H), 7.08 (s, 1H), 7.53 (s, 1H), 8.01 (s, 1H), 9.80 (s, 1H), 12.99 (br, 2H)

Example F-6

4-Methoxy-piperidine-1-carboxylic acid[3-(7,7-dimethyl-6-oxo-1,5,6,7-tetrahydro-imidazo[4,5-f]indol-2-yl)-1H-pyrazol-4-yl]-amide 4-Methoxy-piperidine-1-carboxylic acid[3-(7,7-dimethyl-6-oxo-1,5,6,7-tetrahydro-imidazo[4,5-f]indol-2-yl)-1H-pyrazol-4-yl]-amide was prepared using 2-(4-Amino-1H-pyrazol-3-yl)-5-ethyl-7,7-dimethyl-5,7-dihydro-1H-imidazo[4,5-f]indol-6-one (400 mg, 1.29 mmol) and 4-methoxypiperidin (297 mg, 2.58 mmol). The title compound was obtained as off-white powder (170 mg, 29%).

MS: M=452.2 (API+)

¹H-NMR (500 MHz, D₆-DMSO): δ (ppm)=1.20 (m, 3H), 1.32 (m, 6H), 1.48 (m, 2H), 1.94 (m, 2H), 3.30 (m, 5H), 3.44 (m, 1H), 3.78 (m, 4H), 7.01 and 7.26 (d, 1H, tautomeric forms), 7.42 and 7.65 (d, 1H, tautomeric forms), 8.02 (s, 1H), 10.01 (s, 1H), 12.98 (m, 2H)

Example F-7

1-(2-Diethylamino-ethyl)-3-[3-(5-ethyl-7,7-dimethyl-6-oxo-1,5,6,7-tetrahydro-imidazo[4,5-f]indol-2-yl)-1H-pyrazol-4-yl]-1-methyl-urea 1-(2-Diethylamino-ethyl)-3-[3-(5-ethyl-7,7-dimethyl-6-oxo-1,5,6,7-tetrahydro-imidazo[4,5-f]indol-2-yl)-1H-pyrazol-4-yl]-1-methyl-urea was prepared using 2-(4-Amino-1H-pyrazol-3-yl)-5-ethyl-7,7-dimethyl-5,7-dihydro-1H-imidazo[4,5-f]indol-6-one (400 mg, 1.29 mmol) and N,N-diethyl-N'-methylethylendiamin (336 mg, 2.58 mmol). The title compound was obtained as off-white powder (90 mg, 15%).

MS: M=467.3 (API+)

¹H-NMR (500 MHz, D₆-DMSO): δ (ppm)=1.20 (m, 9H), 1.35 (s, 6H), 2.10 (s, 2H), 3.01 (m, 6H), 3.21 (s, 3H), 3.73 (m, 2H), 6.86 (s, 1H), 7.26 (s, 1H), 7.30 (s, 1H), 8.12 (s, 1H), 9.94 (s, 1H)

Example F-8

1,1-Diethyl-3-[3-(5-isopropyl-7,7-dimethyl-6-oxo-1,5,6,7-tetrahydro-imidazo[4,5-f]indol-2-yl)-1H-pyrazol-4-yl]-urea 1,1-Diethyl-3-[3-(5-isopropyl-7,7-dimethyl-6-oxo-1,5,6,7-tetrahydro-imidazo[4,5-f]indol-2-yl)-1H-pyrazol-4-yl]- urea was prepared using 2-(4-Amino-1H-pyrazol-3-yl)-5-isopropyl-7,7-dimethyl-5,7-dihydro-1H-imidazo[4,5-f]indol-6-one (360 mg, 1.00 mmol) and diethylamine (205 µl, 2.00 mmol). The title compound was obtained as purple powder (100 mg, 22%).

MS: M=424.2 (ESI+)

$^1$H-NMR (500 MHz, D$_6$-DMSO): δ (ppm)=1.24 (s, 6H), 1.31 (m, 6H), 1.46 (m, 6H), 3.45 (m, 4H), 4.55 (m, 1H), 7.10 and 7.22 (d, 1H, tautomeric forms), 7.40 and 7.55 (d, 1H, tautomeric forms), 8.00 (s, 1H), 9.90 (d, 1H), 12.85 (s, 1H), 12.97 (d, 1H)

Example F-9

Azepane-1-carboxylic acid[3-(5-isopropyl-7,7-dimethyl-6-oxo-3,5,6,7-tetrahydro-imidazo[4,5-f indol-2-yl)-1H-pyrazol-4-yl]-amide Azepane-1-carboxylic acid[3-(5-isopropyl-7,7-dimethyl-6-oxo-3,5,6,7-tetrahydro-imidazo[4,5-f]indol-2-yl)-1H-pyrazol-4-yl]-amide was prepared using 2-(4-amino-1H-pyrazol-3-yl)-5-isopropyl-7,7-dimethyl-5,7-dihydro-3H-imidazo[4,5-f]indol-6-one (400 mg, 1.233 mmol) and azepane (245 mg, 2.466 mmol). 93 mg (17%) of the title compound were obtained.

MS: M=450.3 (ESI+)

$^1$H-NMR (400 MHz, DMSO): δ (ppm)=1.30 (s, 6H), 1.45 (d, 6H), 1.54 (m, 4H), 1.82 (m, 4H), 3.56 (m, 4H), 4.56 (m, 1H), 7.10 and 7.26 (s, 1H, two tautomeric forms), 7.40 and 7.56 (s, 1H, two tautomeric forms), 8.00 (s, 1H), 9.87 and 9.95 (br, 1H, two tautomeric forms), 12.83 (br, 1H), 12.95 and 13.00 (br, 1H, two tautomeric forms)

Example F-10

Azepane-1-carboxylic acid[3-(7,7-diethyl-5-isopropyl-6-oxo-1,5,6,7-tetrahydro-imidazo[4,5-f]indol-2-yl)-1H-pyrazol-4-yl]-amide Azepane-1-carboxylic acid[3-(7,7-diethyl-5-isopropyl-6-oxo-1,5,6,7-tetrahydro-imidazo[4,5-f]indol-2-yl)-1H-pyrazol-4-yl]-amide was prepared using 2-(4-amino-1H-pyrazol-3-yl)-7,7-diethyl-5-isopropyl-5,7-dihydro-1H-imidazo[4,5-f]indol-6-one (150 mg, 0.43 mmol) and azepane (84 mg, 0.85 mmol). 9 mg (4%) % of the title compound were obtained.

MS: M=476.3 (ESI−)

$^1$H-NMR (400 MHz, DMSO): δ (ppm)=0.45 (t, 6H), 1.45 (d, 6H), 1.55 (m, 4H), 1.81 (m, 8H), 3.57 (m, 4H), 4.56 (m, 1H), 7.09 and 7.22 (s, 1H, two tautomeric forms), 7.29 and 7.46 (s, 1H, two tautomeric forms), 8.01 (s, 1H), 9.85 and 9.96 (br, 1H, two tautomeric forms), 12.85 and 12.95 (br, 1H, two tautomeric forms), 12.95 and 12.98 (br, 1H, two tautomeric forms)

Example G

General Procedure G

To a solution of appropriate amino pyrazole (0.32 mmol), acetic acid (0.050 ml, 0.88 mmol) and sodium triacetoxy borohydride (102 mg, 0.48 mmol) in DMF (2 ml), an appropriate carbonyl compound (30 µl, 0.53 mmol) was added at room temperature. The mixture was stirred overnight at this temperature. The solvent was evaporated. Aqueous sodium hydroxide (2M, 10 ml) and ethyl acetate (10 ml) were added. The layers were separated and the aqueous layer was extracted three times with ethyl acetate (AcOEt) (3×20 ml). The combined organic layers were dried and evaporated to afford a residue purified by HPLC.

Example G-1

5-Ethyl-2-(4-ethylamino-1H-pyrazol-3-yl)-7,7-dimethyl-5,7-dihydro-1H-imidazo[4,5-f]indol-6-one 5-Ethyl-2-(4-ethylamino-1H-pyrazol-3-yl)-7,7-dimethyl-5,7-dihydro-1H-imidazo[4,5-f]indol-6-one was prepared using 2-(4-amino-1H-pyrazol-3-yl)-5-ethyl-7,7-dimethyl-5,7-dihydro-1H-imidazo[4,5-f]indol-6-one (100 mg, 0.32 mmol) and acetaldehyde (30 µl, 0.53 mmol). The title compound was obtained as light grey powder (23 mg).

MS: M=339.1 (API+)

$^1$H-NMR (400 MHz, D$_6$-DMSO): δ (ppm)=1.20 (m, 6H), 1.30 (s, 6H), 2.24 (s, 3H), 3.05 (q, 2H), 3.75 (m, 2H), 4.95 and 5.30 (s, 1H, tautomeric forms), 6.96 and 7.20 (s, 1H, tautomeric forms), 7.29 (s, 1H), 7.35 and 7.62 (s, 1H, tautomeric forms), 12.55 (br, 2H)

Example G-2

2-(4-Benzylamino-5-methyl-1H-pyrazol-3-yl)-5-ethyl-7,7-dimethyl-5,7-dihydro-1H-imidazo[4,5-f] indol-6-one 2-(4-Benzylamino-5-methyl-1H-pyrazol-3-yl)-5-ethyl-7,7-dimethyl-5,7-dihydro-1H-imidazo[4,5-f]indol-6-one was prepared using 2-(4-Amino-1H-pyrazol-3-yl)-5-ethyl-7,7-dimethyl-5,7-dihydro-1H-imidazo[4,5-f]indol-6-one (150 mg, 0.46 mmol) and benzaldehyde (70 µl, 0.69 mmol). The title compound was obtained as white powder (34 mg, 17%).

MS: M=415.3 (ESI+)

$^1$H-NMR (400 MHz, D$_6$-DMSO): δ (ppm)=1.18 (m, 3H), 1.30 (s, 6H), 2.22 (s, 3H), 3.74 (m, 2H), 4.33 (s, 2H), 5.95 (br, 1H), 7.27 (m, 7H), 12.55 (m, 2H)

Example H

General Procedure H

To a solution of appropriate amino pyrazole (0.53 mmol) in tetrahydrofuran (THF) (10 ml), appropriate sulfonyl chloride (1.59 mmol) and N,N-diisopropyl-ethylamine (DIPEA) (0.40 ml, 2.25 mmol) were slowly added at 0° C. under argon atmosphere and stirred overnight at room temperature. The solvent was evaporated and the residue was dissolved in methanol (3 ml). After addition of aqueous ammonia (1.5 ml), the mixture was refluxed for 20 hours. The solvent was evaporated and the residue was purified either by flash chromatography or HPLC.

Example H-1

N-[3-(7,7-Dimethyl-6-oxo-1,5,6,7-tetrahydro-imidazo[4,5-f]indol-2-yl)-1H-pyrazol-4-yl]-benzenesulfonamide N-[3-(7,7-Dimethyl-6-oxo-1,5,6,7-tetrahydro-imidazo[4,5-f]indol-2-yl)-1H-pyrazol-4-yl]-benzenesulfonamide was prepared using 2-(4-amino-1H-pyrazol-3-yl)-7,7-dimethyl-5,7-dihydro-1H-imidazo[4,5-f]indol-6-one (150 mg, 0.53 mmol) and phenylsulfonylchloride. The title compound was obtained as white powder (66 mg).

MS: M=423.0 (API+)

$^1$H-NMR (400 MHz, D$_6$-DMSO): δ (ppm)=1.31 (s, 6H), 6.90 (br, 1H), 7.41-7.53 (m, 5H), 7.78 (m, 3H), 10.30 (s, 1H), 12.00 and 12.75 (br, 1H), 13.25 (br, 1H)

Example H-2

N-[3-(5-Ethyl-7,7-dimethyl-6-oxo-3,5,6,7-tetrahydro-imidazo[4,5-f]indol-2-yl)-1H-pyrazol-4-yl]-methanesulfonamide N-[3-(5-Ethyl-7,7-dimethyl-6-oxo-3,5,6,7-tetrahydro-imidazo[4,5-f]indol-2-yl)-1H-pyrazol-4-yl]-methanesulfonamide was prepared using 2-(4-Amino-1H-pyrazol-3-yl)-5-ethyl-7,7-dimethyl-5,7-dihydro-1H-imidazo[4,5-f]indol-6-one (100 mg, 0.32 mmol) and Methansulfonylchloride (30 µl, 0.39 mmol). The title compound was obtained as off-white powder (30 mg, 24%).

MS: M=389.3 (ESI+)

$^1$H-NMR (400 MHz, D$_6$-DMSO): δ (ppm)=1.20 (m, 3H), 1.31 (m, 6H), 3.02 (s, 3H), 3.76 (m, 2H), 7.03 and 7.34 (d, 1H, tautomeric forms), 7.36 and 7.69 (d, 1H, tautomeric forms), 7.89 (s, 1H), 9.26 (br, 1H), 13.01 (br, 1H), 13.31 (br, 1H)

Example I

General Procedure I

The following compound are prepared using either the general procedures described in Example E or Example F and starting from the appropriate starting materials. Or, alternatively, the following compound are prepared reacting 3-oxetanyloxycarbonyloxysuccinimide (see WO 93/19059 and WO 93/23373) with the appropriate amino pyrazole and, if necessary, performing the reaction in the presence of a base like triethylamine, diisopropyl-ethyl-amine, sodium hydride and the like, and in an inert solvents like dichloromethane, N,N-dimethylformamide, tetrahydrofurane and the like, at temperatures between room temperature and 100° C.:

Example I-1

[3-(5-Isopropyl-7,7-dimethyl-6-oxo-1,5,6,7-tetrahydro-imidazo[4,5-f]indol-2-yl)-1H-pyrazol-4-yl]-carbamic acid oxetan-3-yl ester

Example I-2

[3-(5-Isopropyl-7,7-ethyl-6-oxo-1,5,6,7-tetrahydro-imidazo[4,5-f]indol-2-yl)-1H-pyrazol-4-yl]-carbamic acid oxetan-3-yl ester

Example I-3

[3-(5,7,7-triethyl-6-oxo-1,5,6,7-tetrahydro-imidazo[4,5-f]indol-2-yl)-1H-pyrazol-4-yl]-carbamic acid oxetan-3-yl ester

Example I

General Procedure I

Using the general procedures described above, especially from Examples A, B or C, and starting from the appropriate starting materials or, alternatively using the methods and/or starting materials or methods to prepare such starting materials, described in WO 00/38680, WO 93/19059, DE 1 907 117 or DE 3 618 135 the following compounds are prepared:

Example I-1

Oxetane-3-carboxylic acid[3-(5-isopropyl-7,7-dimethyl-6-oxo-1,5,6,7-tetrahydro-imidazo[4,5-f]indol-2-yl)-1H-pyrazol-4-yl]-amide

Example I-2

Oxetane-3-carboxylic acid[3-(5-isopropyl-7,7-ethyl-6-oxo-1,5,6,7-tetrahydro-imidazo[4,5-f]indol-2-yl)-1H-pyrazol-4-yl]-amide

Example I-3

Oxetane-3-carboxylic acid[3-(5,7,7-triethyl-6-oxo-1,5,6,7-tetrahydro-imidazo[4,5-f]indol-2-yl)-1H-pyrazol-4-yl]-amide Unless stated to the contrary, all compounds in the examples were prepared and characterized as described. All ranges recited herein encompass all combinations and subcombinations included within that range limit. All patents and publications cited herein are hereby incorporated by reference in their entirety for any purpose.

The invention claimed is:

1. A compound according to formula I,

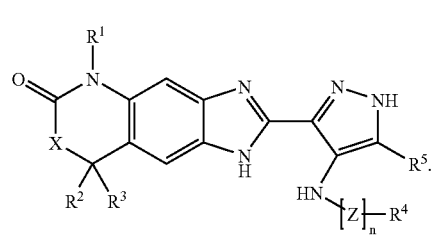

formula I wherein:
R$^1$ is selected from the group consisting of hydrogen and alkyl;
R$^2$ is alkyl;
R$^3$ is alkyl;
Z is selected from the group consisting of:
—C(O)—,
—C(O)NR$^7$—,
—C(O)O—, and
—S(O)$_2$—;
n is 0 or 1;
R$^7$ is hydrogen or alkyl;
R$^4$ is selected from the group consisting of:
hydrogen;
alkyl, which is optionally substituted one or more times by halogen, alkoxy, or dialkylamino;
aryl-V—, wherein the aryl is optionally substituted one or more times by halogen, cyano 2,4-dioxa-pentan-1,5-diyl, 2,5-dioxa-hexan-1,6-diyl, hydroxy, (C$_1$-C$_4$)alkyl, (C$_1$-C$_4$)alkoxy, or halogenated (C$_1$-C$_4$)alkyl;
heteroaryl-V—, wherein the heteroaryl is optionally substituted one or more times by alkyl;
cycloalkyl-V—; and
heterocyclyl-V—;
with the proviso that R$^4$ is not hydrogen, if n is 1 and Z is —C(O)O—;
V is selected from the group consisting of:
a single bond, alkylene,
—O-alkylene,
cycloalkylene, and
alkenylene;
$R^5$ is selected from the group consisting of hydrogen and alkyl; and
X is a single bond;
or a pharmaceutically-acceptable salt or ester thereof.

2. A compound according to claim 1, wherein n is 1.

3. A compound according to claim 1, wherein Z is —C(O)— and n is 1.

4. A compound according to claim 1, wherein:
$R^1$ is alkyl;
Z is —C(O)—;
n is 1; and
$R^4$ is selected from the group consisting of:
  alkyl, which is optionally substituted one or more times by halogen or alkoxy;
  aryl-V—, wherein the aryl is optionally substituted one or more times by halogen, cyano, 2,4-dioxa-pentan-1,5-diyl, 2,5-dioxa-hexan-1,6-diyl, $(C_1-C_4)$alkyl, $(C_1-C_4)$alkoxy, or halogenated $(C_1-C_4)$alkyl;
  heteroaryl-V—, wherein the heteroaryl is optionally substituted one or more times by alkyl;
  cycloalkyl-V—; and
  heterocyclyl-V—.

5. A compound according to claim 1, wherein:
(a) $R^1$ is alkyl;
Z is —C(O)—;
n is 1; and
$R^4$ is alkyl, which is optionally substituted one or more times by halogen or alkoxy.

6. A compound according to claim 1, wherein:
$R^1$ is alkyl;
Z is —C(O)—;
n is 1;
$R^4$ is heteroaryl-V—, wherein the heteroaryl is optionally substituted one or more times by alkyl;
V is a single bond or alkylene; and
$R^5$ is hydrogen.

7. A compound according to claim 1, wherein:
$R^1$ is alkyl;
Z is —C(O)—;
n is 1;
$R^4$ is cycloalkyl-V—;
V is a single bond or alkylene; and
$R^5$ is hydrogen.

8. A compound according to claim 1, wherein:
$R^1$ is alkyl;
Z is —C(O)—;
n is 1;
$R^4$ is heterocyclyl-V—;
V is a single bond; and
$R^5$ is hydrogen.

9. A compound according to claim 1, wherein Z is —C(O)NR$^7$— and n is 1.

10. A compound according to claim 1, wherein:
$R^1$ is alkyl;
Z is —C(O)NR$^7$—;
n is 1;
$R^4$ is alkyl, which is optionally substituted one or more times by dialkylamino or aryl-V—;
V is alkylene; and
$R^5$ is hydrogen.

11. A compound according to claim 1, wherein Z is —C(O)O— and n is 1.

12. A compound according to claim 1, wherein:
Z is —C(O)O—;
$R^4$ is selected from the group consisting of:
  alkyl, which is optionally substituted one or more times by alkoxy;
  aryl-V—, wherein the aryl is optionally substituted one or more times by halogen; and
  cycloalkyl-V—;
V is a single bond or alkylene; and
$R^5$ is hydrogen.

13. A compound according to claim 1, selected from the group consisting of:
3-(7,7-Dimethyl-6-oxo-1,5,6,7-tetrahydro-imidazo[4,5-f]indol-2-yl)-1H-pyrazol-4-yl]-carbamic acid benzyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid methyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid phenyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid ethyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid 2,2-dimethyl-propyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid 2-chloro-benzyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid isobutyl ester;
[3-(5-Ethyl-7,7-dimethyl-6-oxo-1,5,6,7-tetrahydro-imidazo[4,5-f]indol-2-yl)-1H-pyrazol-4-yl]-carbamic acid 2-methoxy-ethyl ester; and
[3-(5-Ethyl-7,7-dimethyl-6-oxo-1,5,6,7-tetrahydro-imidazo[4,5-f]indol-2-yl)-1H-pyrazol-4-yl]-carbamic acid isopropyl ester.

14. A compound according to claim 1, wherein Z is —S(O)$_2$— and n is 1.

15. A compound according to claim 1, wherein:
Z is —S(O)$_2$—;
n is 1;
$R^4$ is alkyl or aryl-V—;
V is a single bond; and
$R^5$ is hydrogen.

16. A compound according to claim 1, wherein:
n is 0;
$R^4$ is hydrogen, alkyl or aryl-V—; and
V is a single bond.

17. A pharmaceutical composition comprising amount a compound of claim 1 and a pharmaceutically acceptable carrier.

* * * * *